United States Patent
Miyamoto et al.

(10) Patent No.: US 7,670,787 B2
(45) Date of Patent: Mar. 2, 2010

(54) PROTEIN FORMING COMPLEX WITH C-FOS PROTEIN, NUCLEIC ACID ENCODING THE SAME AND METHOD OF USING THE SAME

(75) Inventors: Etsuko Miyamoto, Yokohama (JP); Masamichi Ishizaka, Yokohama (JP); Hiroshi Yanagawa, Yokohama (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 11/976,827

(22) Filed: Oct. 29, 2007

(65) Prior Publication Data

US 2008/0177030 A1 Jul. 24, 2008

Related U.S. Application Data

(62) Division of application No. 10/538,410, filed as application No. PCT/JP03/14749 on Nov. 19, 2003, now abandoned.

(30) Foreign Application Priority Data

Dec. 11, 2002 (JP) ............................. 2002-360046

(51) Int. Cl.
*G01N 33/53* (2006.01)
(52) U.S. Cl. ...................................... 435/7.1; 435/7.21
(58) Field of Classification Search ................. 435/7.1, 435/7.21
See application file for complete search history.

(56) References Cited

U.S. PATENT DOCUMENTS 6,228,994 B1 5/2001 Yanagawa et al.
6,310,048 B1 10/2001 Kumar

FOREIGN PATENT DOCUMENTS

EP 1 350 845 10/2003
WO 02/48347 6/2002

OTHER PUBLICATIONS

S. Saburi et al., "The Trophinin Gene Encodes a Novel Group of MAGE Proteins, Magphinins, and Regulates Cell Proliferation during Gametogenesis in the Mouse", The Journal of Biological Chemistry, vol. 276, No. 52, pp. 49378-49389, Dec. 28, 2001.
S. Saburi et al., The DDBJ/EMBL/GenBank Databases (online) Submitted Sep. 17, 1999, Accession No. AB032477.
Y. Chinenov et al., "Close Encounters of Many Kinds: Fos-Jun Interactions that Mediate Transcription Regulatory Specificity", Oncogene, vol. 20, No. 19, pp. 2438-2452, Apr. 30, 2001.

*Primary Examiner*—Tekchand Saidha
(74) *Attorney, Agent, or Firm*—Wenderoth, Lind & Ponack, L.L.P.

(57) ABSTRACT

Proteins that interact with c-Fos, nucleic acids encoding them and inhibitors utilizing them as well as methods for detecting an interaction and screening methods utilizing a protein that interacts with c-Fos are provided. Comprehensive analysis of transcription control factor complexes in a mouse brain cDNA library with c-Fos as a bait by using the cotranslation selection and screening of in vitro virus (IVV) and the C-terminal labeling method are conducted, thereby to analyze proteins unknown so far, proteins known so far, but unknown to form a complex with the c-Fos protein, and so forth.

5 Claims, 13 Drawing Sheets

| Amino acid SEQ ID NO. | Name of protein/gene, accession No. | leu zipper | Nucleic acid SEQ ID NO. | Number of clones | Alternate Symbols & Ailas |
|---|---|---|---|---|---|
| 1~14 | Mus musculus fip-cx | O | 23(1), 24(2-1), 25(2-2), 26(2-3), 27(3), 28(4), 29(5), 30(6), 31(7), 32(8), 33(9), 34(10), 35(11), 36(12), 37(13), 38(14) | 29 | Frame shift (mage-d3, mRNA, AF319977. melanoma antigen, family D, 3-like, AK047777. trophinin, NM_019548. Trol, Maged3, Maged3l magphinin-alpha, mRNA, AF241245. magphinin mRNA AB032477. magphinin-beta2 mRNA, AF288605. magphinin-gamma mRNA, AF288606. trophinin-2 mRNA) |
| 15~19 | Mus musculus eukaryotic translation elongation factor 1 delta (guanine nucleotide exchange protein) (Eef1d), mRNA, NM_023240. | O | 39(15), 40(16), 41(17), 42(18), 43(19) | 5 | 5730529A16Rik |
| 20~22 | Mus musculus schwannomin interacting protein 1 (Schip1), mRNA, NM_013928. | O | 44(20), 45(21), 46(22) | 3 | Nf2ip, SCHIP-1 |
| 47~56 | Mus musculus fip-cx.1 | O | 104(47), 105(48), 106(49), 107(50-1), 108(50-2), 109(50-3), 110(50-4), 111(50-5), 112(51-1), 113(51-2), 114(52), 115(53), 116(54), 117(55), 118(56) | 15 | Frame shift (mage-d3, mRNA, AF319977. melanoma antigen, family D, 3-like, AK047777. trophinin, NM_019548. Trol, Maged3, Maged3l) |
| 57~76 | Mus musculus fip-cx.2 | O | 119(57), 120(58), 121(59), 122(60), 123(61), 124(62-1), 125(62-2), 126(63), 127(64), 128(65), 129(66), 130(67), 131(68), 132(69), 133(70), 134(71), 135(72), 136(73), 137(74-1), 138(74-2), 139(75), 140(76) | 31 | Frame shift (magphinin-alpha, mRNA, AF241245. magphinin mRNA AB032477. magphinin-beta2 mRNA, AF288605. magphinin-gamma mRNA, AF288606. trophinin-2 mRNA) |

Fig. 1A

| Amino acid SEQ ID NO. | Name of protein/gene, accession No. | Leu zipper | Nucleic acid SEQ ID NO. | Number of clones | Alternate Symbols & Ailas |
|---|---|---|---|---|---|
| 77~81 | Mus musculus optineurin (Optn), NM_181848 | O | 141(77), 142(78), 143(79), 144(80), 145(81) | 6 | NRP, FIP2, HYPL, 4930441O07Rik, TFIIIA-INTP |
| 82~84 | Mus musculus similar to small nuclear RNA activating complex, polypeptide 5, 19kDa; small nuclear RNA activating complex, polypeptide 5, XM_284503.1 | O | 146(82), 147(83), 148(84) | 2 | Snapc5, 2010103A03Rik |
| 85~86 | Mus musculus C130020M04Rik, BC026483 | O | 149(85), 150(86) | 1 | MGC31554 |
| 87~89 | Rattus norvegicus similar to hypothetical protein FLJ32000, XM_342896.1 | O | 151(87), 152(88), 153(89) | 2 | |
| 90~91 | Mus musculus Ras-like without CAAX 2 (Rit2), NM_009065.2 | x | 154(90), 155(91) | 1 | Rit2 |
| 92~93 | Mus musculus isolate 1 cytochrome b gene, partial . mitocondorial gene, AF540912.1 | O | 156(92), 157(93) | 1 | |
| 94~95 | Mus musculus apolipoprotein E, NM_009696.2 | x | 158(94), 159(95) | 1 | Apoe |
| 96~97 | Mus musculus amyloid beta (A4) precursor protein, BC005490.1 | x | 160(96), 161(97) | 1 | Adap, Cvap, Abeta, appican, betaAPP, protease nexin II |
| 98~99 | Mus musculus DnaJ homolog, subfamily A, member 2, BC003420 | x | 162(98), 163(99) | 1 | Hsp40 homolog, subfamily A, member 2, DNAJ, DNJ3, mDj3, Dnaj3, HIRIP4, PRO3015, DNA J protein |
| 100~101 | MUs musculus fip-c10, XM_136911 | x | 164(100), 165(101) | 1 | Mus musculus similar to KIAA1209 protein |
| 102 | Mus musculus fip-c4 | x | 166(102) | 1 | Genome (Mouse DNA sequence from clone RP23-185C16 on chromosome 4) |
| 103 | Mus musculus fip-c18 | x | 167(103) | 1 | Genome (Mus musculus chromosome 18, clone RP24-572G3, AC102422.10) |

Fig. 1B

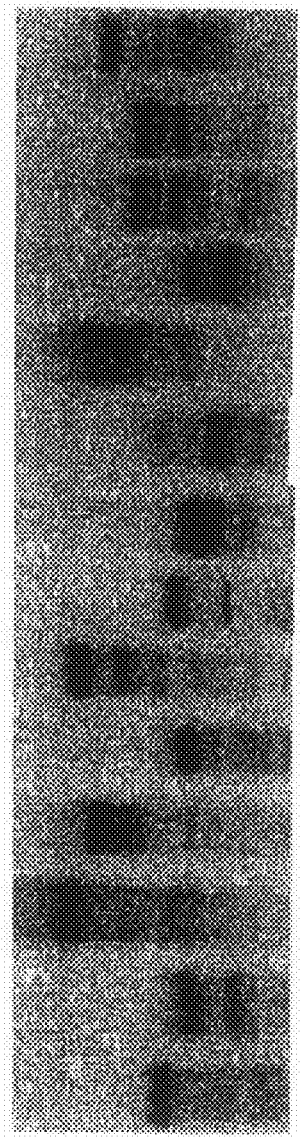
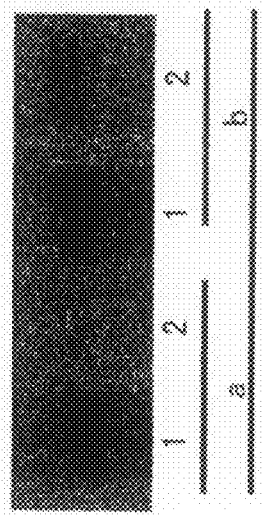
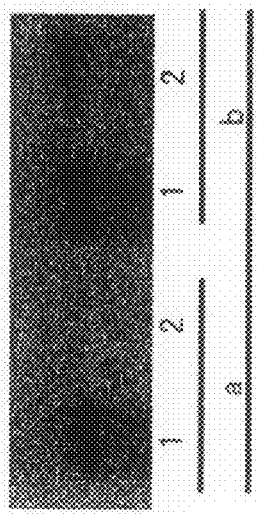
Fig. 5

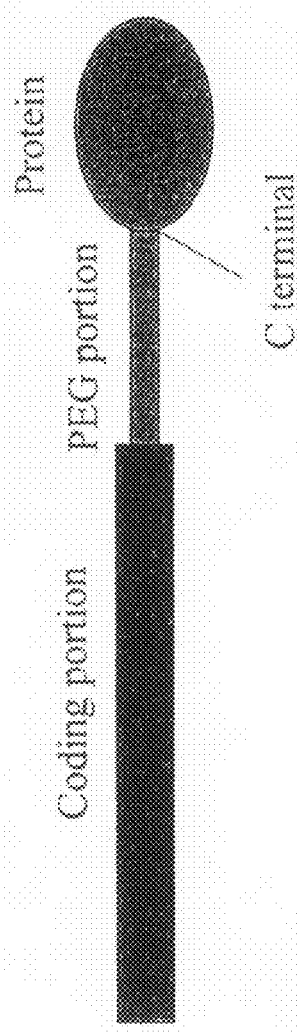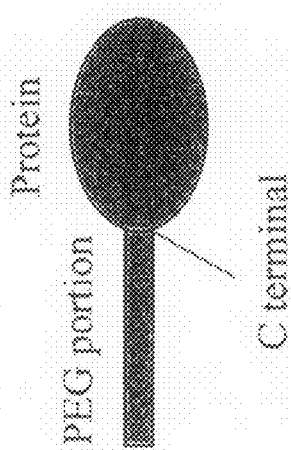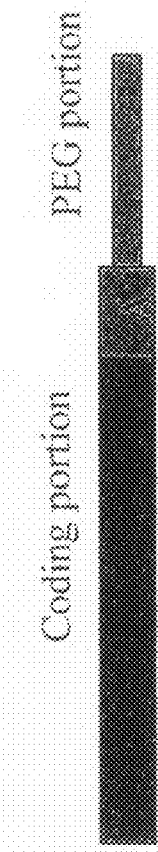
A Protein of which C terminal is modified with translation template
B Translation template
C Protein of which C terminal is modified with PEG portion
Fig. 9

PROTEIN FORMING COMPLEX WITH C-FOS PROTEIN, NUCLEIC ACID ENCODING THE SAME AND METHOD OF USING THE SAME

This application is a divisional of application Ser. No. 10/538,410, filed Feb. 15, 2006, now abandoned, which is a U.S. national stage of International Application No. PCT/JP2003/014749 filed Nov. 19, 2003. The teachings of the above referenced applications are hereby incorporated by reference.

TECHNICAL FIELD

The present invention relates to proteins that interact with c-Fos, nucleic acids encoding them and inhibitors utilizing them as well as methods for detecting an interaction and screening methods utilizing a protein that interacts with c-Fos.

At present, genomic nucleotide sequences of various organisms are going to be elucidated. In researches of genomic sequences, there are expected, as post-sequencing researches of the second act, researches of analyzing meanings of the elucidated genomic information, i.e., structural and functional analyses of genes and proteins (Non-patent documents 1 and 2), analyses of protein/protein and protein/nucleic acid interactions (Non-patent documents 3 and 4) and so forth.

On the basis of analyses of networks of interactions between protein and protein, protein and nucleic acid and so forth in post-sequencing genomic functional analyses utilizing such techniques as described above, it is expected to create drugs and so forth standing on discoveries of novel functions of known proteins or important biological enzymes such as novel proteins that have been unknown so far.

As methods for detecting interactions between proteins, the immunoprecipitation (Non-patent document 5), pull-down assay based on a GST fusion protein (Non-patent document 6), TAP method (Non-patent document 7), yeast two-hybrid method (Non-patent document 8) and so forth are known so far. Further, as methods for comprehensive analysis of interactions between proteins in the post-sequencing genomic functional analyses utilizing the "assignment of gene (genotype) and protein (phenotype)" born as a tool of the evolutionary molecular engineering, there are the in vitro virus method (Non-patent documents 9 and 10, Patent documents 1 and 2), STABLE method (Non-patent document 11), phage display method (Non-patent document 12), ribosome display method (Non-patent document 13, Patent document 3), mRNA-peptide fusion method (mRNA display method, Non-patent document 14), and so forth.

Furthermore, the surface plasmon resonance method, fluorescence resonance energy transfer method, fluorescence depolarization method, evanescent-field imaging method, fluorescence correlation spectroscopy, fluorescent imaging method, enzyme linked immunosorbent assay and so forth are also known. Moreover, methods of modifying C-terminals of proteins in a translation system utilizing a nucleic acid derivatives such as puromycin have been previously proposed (Patent documents 4 and 5). These methods have advantages that functions of proteins are more unlikely to be damaged compared with the conventional chemical modification methods and the fluorescent protein fusion methods.

In the field of life science, sequence analysis of the human genome was completed, and genome researches rush into functional analyses of genes of the post-genome age. Thus, innovative drug creation based on comprehensive genomic functional analyses and so forth are expected. There is desired a technique that enables comprehensive analysis of genes and proteins, which have been independently studied so far, for example, a technique of analyzing various cofactors of transcription control factors as target proteins of drug creation at once and so forth. As a transcription control factor, the c-Fos protein is known well.

The v-fos gene was isolated as an oncogene of an FBJ murine osteosarcoma virus (Non-patent document 15). c-fos is a transcription control factor detected in many cell species as a typical immediate early gene in connection with a proliferation stimulus. fra-1 and fra-2 were cloned from the Fos-related antigens (Fra), and fosB was also found as a gene having homology to c-fos in the nucleotide sequence. These constitute the fos family genes together with c-fos. It is known that a chimeric mouse and transgenic mouse expressing c-fos at a high level form chondroma and bone sarcoma, respectively (Non-patent document 16).

Various genes such as c-jun, junB and junD, which are jun family genes, are known so far as genes of proteins that interact with c-fos (Non-patent document 17), and it was recently found by the two-hybrid method that the transcription control factor Fos/Jun (AP-1) forms a complex with BAF60a of SWI/SNF to induce remodeling of chromatin. Further, it was found that AP-1 binds to NFAT, which is a protein of the cerebral nerve system, to control expression of the IL2 gene. The former is involved in oncogenesis and canceration, and the latter consists of two proteins that are involved in autoimmune diseases and Alzheimer's disease and induce completely different diseases. Thus, comprehensive analyses of various complexes of transcription control factors are very interesting as a new treasury of target proteins for drug creation. However, such a thorough 1:1 molecule analysis technique as the two-hybrid method takes enormous time and labor.

<Non-patent document 1>
Saegusa A., Nature, 401, 6751 (1999)

<Non-patent document 2>
Dalton R, Abbott A., Nature, 402, 6763 (1999)

<Non-patent document 3>
Etsuko Miyamoto, Hiroshi Yanagawa, Series Genome Science of Post-sequencing 3, Proteomics, pp. 136-145 (2000)

<Non-patent document 4>
Etsuko Miyamoto, Hiroshi Yanagawa, PROTEIN, NUCLEIC ACID AND ENZYME, 46(2), pp. 138-147 (2001)

<Non-patent document 5>
Xiong et al., Nature, 366, 701-704 (1993)

<Non-patent document 6>
Kaelin, et al., Cell, 64, 521-532 (1991)

<Non-patent document 7>
Guillaume Rigaut, et al., Nature Biotechnology, 17, 1030 (1999)

<Non-patent document 8>
Fields S., Song O., Nature, 340, 245 (1989)

<Non-patent document 9>
Miyamoto-Sato E., et al., Viva Origino, 25, 35 (1997)

<Non-patent document 10>
Nemoto N., et al., FEBS Lett., 414, 405 (1997)

<Patent document 1>
International Publication WO98/16636

<Patent document 2>
International Publication WO02/46395

<Non-patent document 11>
Doi N., Yanagawa H., FEBS Lett., 457, 227 (1999)

<Non-patent document 12>
Smith G. P., Science, 228, 1315 (1985)

<Non-patent document 13>
Mattheakis, L. C. et al., Proc. Natl. Acad. Sci. USA, 91, 9022-9026 (1994)

<Patent document 3>
International Publication WO95/11922

<Non-patent document 14>
Roberts R. W. and Szostak J. W., Proc. Natl. Acad. Sci. USA, 94, 12297 (1997)

<Patent document 4>
U.S. Pat. No. 6,228,994

<Patent document 5>
International Publication WO02/48347

<Non-patent document 15>
Curran, T. et al., J. Viol., 44:674-682 (1982)

<Non-patent document 16>
Agamemunon, E. G. et al., Trends Genet., 11:436-441 (1995)

<Non-patent document 17>
Yurii Chinenovl and Tom K Kerppola, Oncogene, 20, 2438-2452 (2001)

DISCLOSURE OF THE INVENTION

An object of the present invention is to provide a complex that interacts with the c-Fos protein, which is well known as a transcription control factor, as a target protein.

The inventors of the present invention conducted comprehensive analysis of transcription control factor complexes in a mouse brain cDNA library with c-Fos as a bait by using two of techniques, the cotranslation selection and screening of in vitro virus (IVV) and the C-terminal labeling method (U.S. Pat. No. 6,228,994, WO02/48347) named puromycin technologies, which have been researched on the basis of the aforementioned in vitro virus method as a method for comprehensive analysis as a one-to-multiple molecule-analysis method replacing the method, and thereby attempted to analyze proteins unknown so far, proteins known so far, but unknown to form a complex with the c-Fos protein, and so forth. The expression of "a protein that form a complex" used herein refers to a protein that directly or indirectly interacts with the c-Fos protein.

Further objects of the present invention is to provide a protein that interacts with c-Fos and an inhibitor utilizing it, as well as a method for detecting an interaction and method for screening utilizing a protein that interacts with c-Fos.

The inventors of the present invention found novel proteins that interact with c-Fos by the cotranslation screening, also found that certain known proteins interacted with c-Fos, and accomplished the present invention. The present invention thus provides the followings.

1. A protein of the following (a) or (b):
(a) a protein comprising any one of the amino acid sequences of SEQ ID NOS: 1 to 14,
(b) a protein that comprises any one of the amino acid sequences of SEQ ID NOS: 1 to 14 including deletion, substitution or addition of one or several amino acid residues and interacts with a c-Fos protein.

2. A protein according to 1, which comprises any one of the amino acid sequences of SEQ ID NOS: 1 to 14.

3. A nucleic acid encoding the protein according to 1 or 2.

4. A nucleic acid of the following (a) or (b):
(a) a nucleic acid comprising any one of the nucleotide sequences of SEQ ID NOS: 23 to 38,
(b) a nucleic acid that hybridizes with a nucleic acid comprising any one of the nucleotide sequences of SEQ ID NOS: 23 to 38 under a stringent condition and encodes a protein that interacts with a c-Fos protein.

5. A nucleic acid according to 4, which comprises any one of the nucleotide sequences of SEQ ID NOS: 23 to 38.

6. An inhibitor for an interaction between a protein that interacts with a c-Fos protein and the c-Fos protein, which comprises the protein according to 1 or 2 or a protein translated from the nucleic acid according to any one of 3 to 5 as an active ingredient.

7. A method for detecting an interaction between a bait and a prey, which comprises bringing the bait and the prey into contact and detecting a complex formed by the contact, wherein the bait is the protein according to 1 or 2 or a protein translated from the nucleic acid according to any one of 3 to 5.

8. A method for screening for a prey that interacts with a bait, which comprises the step of detecting an interaction between the bait and a prey by the method according to 7 and the step of selecting a prey for which an interaction was detected.

9. An inhibitor for an interaction between a protein that interacts with a c-Fos protein and the c-Fos protein, which comprises a protein of the following (a) or (b) as an active ingredient:
(a) a protein comprising any one of the amino acid sequences of SEQ ID NOS: 15 to 19,
(b) a protein that comprises any one of the amino acid sequences of SEQ ID NOS: 15 to 19 including deletion, substitution or addition of one or several amino acid residues and interacts with a c-Fos protein.

10. The inhibitor according to 9, wherein the protein as the active ingredient comprises any one of the amino acid sequences of SEQ ID NOS: 15 to 19.

11. The inhibitor according to 9, wherein the protein is a protein translated from a nucleic acid of the following (a) or (b):
(a) a nucleic acid comprising any one of the nucleotide sequences of SEQ ID NOS: 39 to 43,
(b) a nucleic acid that hybridizes with a nucleic acid comprising any one of the nucleotide sequences of SEQ ID NOS: 39 to 43 under a stringent condition and encodes a protein that interacts with the c-Fos protein.

12. The inhibitor according to 11, wherein the nucleic acid comprises any one of the nucleotide sequences of SEQ ID NOS: 39 to 43.

13. A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising any one of the amino acid sequences of SEQ ID NOS: 15 to 19,
(b) a protein that comprises any one of the amino acid sequences of SEQ ID NOS: 15 to 19 including deletion, substitution or addition of one or several amino acid residues and interacts with a c-Fos protein,
(a') a nucleic acid comprising any one of the nucleotide sequences of SEQ ID NOS: 39 to 43, (b') a nucleic acid that hybridizes with a nucleic acid comprising any one of the nucleotide sequences of SEQ ID NOS: 39 to 43 under a stringent condition and encodes a protein that interacts with a c-Fos protein.

14. The method according to 13, wherein the protein comprises any one of the amino acid sequences of SEQ ID NOS: 15 to 19.

15. The method according to 13, wherein the nucleic acid comprises any one of the nucleotide sequences of SEQ ID NOS: 39 to 43.

16. A method for screening for a prey that interacts with a bait, which comprises the step of detecting an interaction between the bait and a prey by the method according to any one of 13 to 15 and the step of selecting a prey for which an interaction is detected.

17. An inhibitor for an interaction between a protein that interacts with a c-Fos protein and the c-Fos protein, which comprises a protein of the following (a) or (b) as an active ingredient:
(a) a protein comprising any one of the amino acid sequences of SEQ ID NOS: 20 to 22,
(b) a protein that comprises any one of the amino acid sequences of SEQ ID NOS: 20 to 22 including deletion, substitution or addition of one or several amino acid residues and interacts with the c-Fos protein.

18. The inhibitor according to 17, wherein the protein as the active ingredient comprises any one of the amino acid sequences of SEQ ID NOS: 20 to 22.

19. The inhibitor according to 17, wherein the protein is a protein translated from a nucleic acid of the following (a) or (b):
(a) a nucleic acid comprising any one of the nucleotide sequences of SEQ ID NOS: 44 to 46,
(b) a nucleic acid that hybridizes with a nucleic acid comprising any one of the nucleotide sequences of SEQ ID NOS: 44 to 46 under a stringent condition and encodes a protein that interacts with the c-Fos protein.

20. The inhibitor according to 19, wherein the nucleic acid comprises any one of the nucleotide sequences of SEQ ID NOS: 44 to 46.

21. A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising any one of the amino acid sequences of SEQ ID NOS: 20 to 22,
(b) a protein that comprises any one of the amino acid sequences of SEQ ID NOS: 20 to 22 including deletion, substitution or addition of one or several amino acid residues and interacts with a c-Fos protein,
(a') a nucleic acid comprising any one of the nucleotide sequences of SEQ ID NOS: 44 to 46,
(b') a nucleic acid that hybridizes with a nucleic acid comprising any one of the nucleotide sequences of SEQ ID NOS: 44 to 46 under a stringent condition and encodes a protein that interacts with a c-Fos protein.

22. The method according to 21, wherein the protein comprises any one of the amino acid sequences of SEQ ID NOS: 20 to 22.

23. The method according to 21, wherein the nucleic acid comprises any one of the nucleotide sequences of SEQ ID NOS: 44 to 46.

24. A method for screening for a prey that interacts with a bait, which comprises the step of detecting an interaction between the bait and a prey by the method according to any one of 21 to 23 and the step of selecting a prey for which an interaction is detected.

25. A protein of the following (a) or (b):
(a) a protein comprising any one of the amino acid sequences of SEQ ID NOS: 47 to 56,
(b) a protein that comprises any one of the amino acid sequences of SEQ ID NOS: 47 to 56 including deletion, substitution or addition of one or several amino acid residues and interacts with a c-Fos protein.

26. A protein according to 25, which comprises any one of the amino acid sequences of SEQ ID NOS: 47 to 56.

27. A nucleic acid encoding the protein according to 25 or 26.

28. A nucleic acid of the following (a) or (b):
(a) a nucleic acid comprising any one of the nucleotide sequences of SEQ ID NOS: 104 to 118,
(b) a nucleic acid that hybridizes with a nucleic acid comprising any one of the nucleotide sequences of SEQ ID NOS: 104 to 118 under a stringent condition and encodes a protein that interacts with a c-Fos protein.

29. A nucleic acid according to 28, which comprises any one of the nucleotide sequences of SEQ ID NOS: 104 to 118.

30. An inhibitor for an interaction between a protein that interacts with a c-Fos protein and the c-Fos protein, which comprises the protein according to 25 or 26 or a protein translated from the nucleic acid according to any one of 27 to 29 as an active ingredient.

31. A method for detecting an interaction between a bait and a prey, which comprises bringing the bait and the prey into contact and detecting a complex formed by the contact, wherein the bait is the protein according to 25 or 26 or a protein translated from the nucleic acid according to any one of 27 to 29 as an active ingredient.

32. A method for screening for a prey that interacts with a bait, which comprises the step of detecting an interaction between the bait and a prey by the method according to 31 and the step of selecting a prey for which an interaction was detected.

33. A protein of the following (a) or (b):
(a) a protein comprising any one of the amino acid sequences of SEQ ID NOS: 57 to 76,
(b) a protein that comprises any one of the amino acid sequences of SEQ ID NOS: 57 to 76 including deletion, substitution or addition of one or several amino acid residues and interacts with a c-Fos protein.

34. A protein according to 33, which comprises any one of the amino acid sequences of SEQ ID NOS: 57 to 76.

35. A nucleic acid encoding the protein according to 33 or 34.

36. A nucleic acid of the following (a) or (b):
(a) a nucleic acid comprising any one of the nucleotide sequences of SEQ ID NOS: 119 to 140,
(b) a nucleic acid that hybridizes with a nucleic acid comprising any one of the nucleotide sequences of SEQ ID NOS: 119 to 140 under a stringent condition and encodes a protein that interacts with a c-Fos protein.

37. A nucleic acid according to 36, which comprises any one of the nucleotide sequences of SEQ ID NOS: 119 to 140.

38. An inhibitor for an interaction between a protein that interacts with a c-Fos protein and the c-Fos protein, which comprises the protein according to 33 or 34 or a protein translated from the nucleic acid according to any one of 35 to 37 as an active ingredient.

39. A method for detecting an interaction between a bait and a prey, which comprises bringing the bait and the prey into contact and detecting a complex formed by the contact, wherein the bait is the protein according to 33 or 34 or a protein translated from the nucleic acid according to any one of 35 to 37 as an active ingredient.

40. A method for screening for a prey that interacts with a bait, which comprises the step of detecting an interaction between the bait and a prey by the method according to 39 and the step of selecting a prey for which an interaction was detected.

41. An inhibitor for an interaction between a protein that interacts with a c-Fos protein and the c-Fos protein, which comprises a protein of the following (a) or (b) as an active ingredient:
(a) a protein comprising any one of the amino acid sequences of SEQ ID NOS: 77 to 81,
(b) a protein that comprises any one of the amino acid sequences of SEQ ID NOS: 77 to 81 including deletion, substitution or addition of one or several amino acid residues and interacts with the c-Fos protein.

42. The inhibitor according to 41, wherein the protein as the active ingredient comprises any one of the amino acid sequences of SEQ ID NOS: 77 to 81.

43. The inhibitor according to 41, wherein the protein is a protein translated from a nucleic acid of the following (a) or (b):
(a) a nucleic acid comprising any one of the nucleotide sequences of SEQ ID NOS: 141 to 145,
(b) a nucleic acid that hybridizes with a nucleic acid comprising any one of the nucleotide sequences of SEQ ID NOS: 141 to 145 under a stringent condition and encodes a protein that interacts with the c-Fos protein.

44. The inhibitor according to 43, wherein the nucleic acid comprises any one of the nucleotide sequences of SEQ ID NOS: 141 to 145.

45. A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising any one of the amino acid sequences of SEQ ID NOS: 77 to 81,
(b) a protein that comprises any one of the amino acid sequences of SEQ ID NOS: 77 to 81 including deletion, substitution or addition of one or several amino acid residues and interacts with a c-Fos protein,
(a') a nucleic acid comprising any one of the nucleotide sequences of SEQ ID NOS: 141 to 145,
(b') a nucleic acid that hybridizes with a nucleic acid comprising any one of the nucleotide sequences of SEQ ID NOS: 141 to 145 under a stringent condition and encodes a protein that interacts with a c-Fos protein.

46. The method according to 45, wherein the protein comprises any one of the amino acid sequences of SEQ ID NOS: 77 to 81.

47. The method according to 45, wherein the nucleic acid comprises any one of the nucleotide sequences of SEQ ID NOS: 141 to 145.

48. A method for screening for a prey that interacts with a bait, which comprises the step of detecting an interaction between the bait and a prey by the method according to any one of 45 to 47 and the step of selecting a prey for which an interaction is detected.

49. An inhibitor for an interaction between a protein that interacts with a c-Fos protein and the c-Fos protein, which comprises a protein of the following (a) or (b) as an active ingredient:
(a) a protein comprising any one of the amino acid sequences of SEQ ID NOS: 82 to 84,
(b) a protein that comprises any one of the amino acid sequences of SEQ ID NOS: 82 to 84 including deletion, substitution or addition of one or several amino acid residues and interacts with the c-Fos protein.

50. The inhibitor according to 49, wherein the protein as the active ingredient comprises any one of the amino acid sequences of SEQ ID NOS: 82 to 84.

51. The inhibitor according to 49, wherein the protein is a protein translated from a nucleic acid of the following (a) or (b):
(a) a nucleic acid comprising any one of the nucleotide sequences of SEQ ID NOS: 146 to 148,
(b) a nucleic acid that hybridizes with a nucleic acid comprising any one of the nucleotide sequences of SEQ ID NOS: 146 to 148 under a stringent condition and encodes a protein that interacts with the c-Fos protein.

52. The inhibitor according to 51, wherein the nucleic acid comprises any one of the nucleotide sequences of SEQ ID NOS: 146 to 148.

53. A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising any one of the amino acid sequences of SEQ ID NOS: 82 to 84,
(b) a protein that comprises any one of the amino acid sequences of SEQ ID NOS: 82 to 84 including deletion, substitution or addition of one or several amino acid residues and interacts with a c-Fos protein,
(a') a nucleic acid comprising any one of the nucleotide sequences of SEQ ID NOS: 146 to 148,
(b') a nucleic acid that hybridizes with a nucleic acid comprising any one of the nucleotide sequences of SEQ ID NOS: 146 to 148 under a stringent condition and encodes a protein that interacts with a c-Fos protein.

54. The method according to 53, wherein the protein comprises any one of the amino acid sequences of SEQ ID NOS: 82 to 84.

55. The method according to 53, wherein the nucleic acid comprises any one of the nucleotide sequences of SEQ ID NOS: 146 to 148.

56. A method for screening for a prey that interacts with a bait, which comprises the step of detecting an interaction between the bait and a prey by the method according to any one of 53 to 55 and the step of selecting a prey for which an interaction is detected.

57. An inhibitor for an interaction between a protein that interacts with a c-Fos protein and the c-Fos protein, which comprises a protein of the following (a) or (b) as an active ingredient:
(a) a protein comprising the amino acid sequence of SEQ ID NO: 85 or 86,
(b) a protein that comprises the amino acid sequence of SEQ ID NO: 85 or 86 including deletion, substitution or addition of one or several amino acid residues and interacts with the c-Fos protein.

58. The inhibitor according to 57, wherein the protein as the active ingredient comprises the amino acid sequence of SEQ ID NO: 85 or 86.

59. The inhibitor according to 57, wherein the protein is a protein translated from a nucleic acid of the following (a) or (b):

(a) a nucleic acid comprising the nucleotide sequence of SEQ ID NO: 149 or 150, (b) a nucleic acid that hybridizes with a nucleic acid comprising the nucleotide sequence of SEQ ID NO: 149 or 150 under a stringent condition and encodes a protein that interacts with the c-Fos protein.

60. The inhibitor according to 59, wherein the nucleic acid comprises the nucleotide sequence of SEQ ID NO: 149 or 150.

61. A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):

(a) a protein comprising the amino acid sequence of SEQ ID NO: 85 or 86, (b) a protein that comprises the amino acid sequence of SEQ ID NO: 85 or 86 including deletion, substitution or addition of one or several amino acid residues and interacts with a c-Fos protein, (a') a nucleic acid comprising the nucleotide sequence of SEQ ID NO: 149 or 150, (b') a nucleic acid that hybridizes with a nucleic acid comprising the nucleotide sequence of SEQ ID NO: 149 or 150 under a stringent condition and encodes a protein that interacts with a c-Fos protein.

62. The method according to 61, wherein the protein comprises the amino acid sequence of SEQ ID NO: 85 or 86.

63. The method according to 61, wherein the nucleic acid comprises the nucleotide sequence of SEQ ID NO: 149 or 150.

64. A method for screening for a prey that interacts with a bait, which comprises the step of detecting an interaction between the bait and a prey by the method according to any one of 61 to 63 and the step of selecting a prey for which an interaction is detected.

65. An inhibitor for an interaction between a protein that interacts with a c-Fos protein and the c-Fos protein, which comprises a protein of the following (a) or (b) as an active ingredient:

(a) a protein comprising any one of the amino acid sequences of SEQ ID NOS: 87 to 89, (b) a protein that comprises any one of the amino acid sequences of SEQ ID NOS: 87 to 89 including deletion, substitution or addition of one or several amino acid residues and interacts with the c-Fos protein.

66. The inhibitor according to 65, wherein the protein as the active ingredient comprises any one of the amino acid sequences of SEQ ID NOS: 87 to 89.

67. The inhibitor according to 65, wherein the protein is a protein translated from a nucleic acid of the following (a) or (b):

(a) a nucleic acid comprising any one of the nucleotide sequences of SEQ ID NOS: 151 to 153, (b) a nucleic acid that hybridizes with a nucleic acid comprising any one of the nucleotide sequences of SEQ ID NOS: 151 to 153 under a stringent condition and encodes a protein that interacts with the c-Fos protein.

68. The inhibitor according to 67, wherein the nucleic acid comprises any one of the nucleotide sequences of SEQ ID NOS: 151 to 153.

69. A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):

(a) a protein comprising any one of the amino acid sequences of SEQ ID NOS: 87 to 89, (b) a protein that comprises any one of the amino acid sequences of SEQ ID NOS: 87 to 89 including deletion, substitution or addition of one or several amino acid residues and interacts with a c-Fos protein, (a') a nucleic acid comprising any one of the nucleotide sequences of SEQ ID NOS: 151 to 153, (b') a nucleic acid that hybridizes with a nucleic acid comprising any one of the nucleotide sequences of SEQ ID NOS: 151 to 153 under a stringent condition and encodes a protein that interacts with a c-Fos protein.

70. The method according to 69, wherein the protein comprises any one of the amino acid sequences of SEQ ID NOS: 87 to 89.

71. The method according to 70, wherein the nucleic acid comprises any one of the nucleotide sequences of SEQ ID NOS: 151 to 153.

72. A method for screening for a prey that interacts with a bait, which comprises the step of detecting an interaction between the bait and a prey by the method according to any one of 69 to 71 and the step of selecting a prey for which an interaction is detected.

73. An inhibitor for an interaction between a protein that interacts with a c-Fos protein and the c-Fos protein, which comprises a protein of the following (a) or (b) as an active ingredient:

(a) a protein comprising the amino acid sequence of SEQ ID NO: 90 or 91, (b) a protein that comprises the amino acid sequence of SEQ ID NO: 90 or 91 including deletion, substitution or addition of one or several amino acid residues and interacts with the c-Fos protein.

74. The inhibitor according to 73, wherein the protein as the active ingredient comprises the amino acid sequence of SEQ ID NO: 90 or 91.

75. The inhibitor according to 73, wherein the protein is a protein translated from a nucleic acid of the following (a) or (b):

(a) a nucleic acid comprising the nucleotide sequence of SEQ ID NO: 154 or 155, (b) a nucleic acid that hybridizes with a nucleic acid comprising the nucleotide sequence of SEQ ID NO: 154 or 155 under a stringent condition and encodes a protein that interacts with the c-Fos protein.

76. The inhibitor according to 75, wherein the nucleic acid comprises the nucleotide sequence of SEQ ID NO: 154 or 155.

77. A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):

(a) a protein comprising the amino acid sequence of SEQ ID NO: 90 or 91, (b) a protein that comprises the amino acid sequence of SEQ ID NO: 90 or 91 including deletion, substitution or addition of one or several amino acid residues and interacts with a c-Fos protein, (a') a nucleic acid comprising the nucleotide sequence of SEQ ID NO: 154 or 155, (b') a nucleic acid that hybridizes with a nucleic acid comprising the nucleotide sequence of SEQ ID NO: 154 or 155 under a stringent condition and encodes a protein that interacts with a c-Fos protein.

78. The method according to 69, wherein the protein comprises the amino acid sequence of SEQ ID NO: 90 or 91.

79. The method according to 70, wherein the nucleic acid comprises the nucleotide sequence of SEQ ID NO: 154 or 155.

80. A method for screening for a prey that interacts with a bait, which comprises the step of detecting an interaction between the bait and a prey by the method according to any one of 77 to 79 and the step of selecting a prey for which an interaction is detected.

81. An inhibitor for an interaction between a protein that interacts with a c-Fos protein and the c-Fos protein, which comprises a protein of the following (a) or (b) as an active ingredient:
(a) a protein comprising the amino acid sequence of SEQ ID NO: 92 or 93,
(b) a protein that comprises the amino acid sequence of SEQ ID NO: 92 or 93 including deletion, substitution or addition of one or several amino acid residues and interacts with the c-Fos protein.

82. The inhibitor according to 81, wherein the protein as the active ingredient comprises the amino acid sequence of SEQ ID NO: 92 or 93.

83. The inhibitor according to 81, wherein the protein is a protein translated from a nucleic acid of the following (a) or (b):
(a) a nucleic acid comprising the nucleotide sequence of SEQ ID NO: 156 or 157,
(b) a nucleic acid that hybridizes with a nucleic acid comprising the nucleotide sequence of SEQ ID NO: 156 or 157 under a stringent condition and encodes a protein that interacts with the c-Fos protein.

84. The inhibitor according to 83, wherein the nucleic acid comprises the nucleotide sequence of SEQ ID NO: 156 or 157.

85. A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising the amino acid sequence of SEQ ID NO: 92 or 93,
(b) a protein that comprises the amino acid sequence of SEQ ID NO: 92 or 93 including deletion, substitution or addition of one or several amino acid residues and interacts with a c-Fos protein,
(a') a nucleic acid comprising the nucleotide sequence of SEQ ID NO: 156 or 157,
(b') a nucleic acid that hybridizes with a nucleic acid comprising the nucleotide sequence of SEQ ID NO: 156 or 157 under a stringent condition and encodes a protein that interacts with a c-Fos protein.

86. The method according to 85, wherein the protein comprises the amino acid sequence of SEQ ID NO: 92 or 93.

87. The method according to 85, wherein the nucleic acid comprises the nucleotide sequence of SEQ ID NO: 156 or 157.

88. A method for screening for a prey that interacts with a bait, which comprises the step of detecting an interaction between the bait and a prey by the method according to any one of 85 to 87 and the step of selecting a prey for which an interaction is detected.

89. An inhibitor for an interaction between a protein that interacts with a c-Fos protein and the c-Fos protein, which comprises a protein of the following (a) or (b) as an active ingredient:
(a) a protein comprising the amino acid sequence of SEQ ID NO: 94 or 95,
(b) a protein that comprises the amino acid sequence of SEQ ID NO: 94 or 95 including deletion, substitution or addition of one or several amino acid residues and interacts with the c-Fos protein.

90. The inhibitor according to 89, wherein the protein as the active ingredient comprises the amino acid sequence of SEQ ID NO: 94 or 95.

91. The inhibitor according to 89, wherein the protein is a protein translated from a nucleic acid of the following (a) or (b):
(a) a nucleic acid comprising the nucleotide sequence of SEQ ID NO: 158 or 159,
(b) a nucleic acid that hybridizes with a nucleic acid comprising the nucleotide sequence of SEQ ID NO: 158 or 159 under a stringent condition and encodes a protein that interacts with the c-Fos protein.

92. The inhibitor according to 91, wherein the nucleic acid comprises the nucleotide sequence of SEQ ID NO: 158 or 159.

93. A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising the amino acid sequence of SEQ ID NO: 94 or 95,
(b) a protein that comprises the amino acid sequence of SEQ ID NO: 94 or 95 including deletion, substitution or addition of one or several amino acid residues and interacts with a c-Fos protein,
(a') a nucleic acid comprising the nucleotide sequence of SEQ ID NO: 158 or 159,
(b') a nucleic acid that hybridizes with a nucleic acid comprising the nucleotide sequence of SEQ ID NO: 158 or 159 under a stringent condition and encodes a protein that interacts with a c-Fos protein.

94. The method according to 93, wherein the protein comprises the amino acid sequence of SEQ ID NO: 94 or 95.

95. The method according to 93, wherein the nucleic acid comprises the nucleotide sequence of SEQ ID NO: 158 or 159.

96. A method for screening for a prey that interacts with a bait, which comprises the step of detecting an interaction between the bait and a prey by the method according to any one of 93 to 95 and the step of selecting a prey for which an interaction is detected.

97. An inhibitor for an interaction between a protein that interacts with a c-Fos protein and the c-Fos protein, which comprises a protein of the following (a) or (b) as an active ingredient:
(a) a protein comprising the amino acid sequence of SEQ ID NO: 96 or 97,
(b) a protein that comprises the amino acid sequence of SEQ ID NO: 96 or 97 including deletion, substitution or addition of one or several amino acid residues and interacts with the c-Fos protein.

98. The inhibitor according to 97, wherein the protein as the active ingredient comprises the amino acid sequence of SEQ ID NO: 96 or 97.

99. The inhibitor according to 97, wherein the protein is a protein translated from a nucleic acid of the following (a) or (b):
(a) a nucleic acid comprising the nucleotide sequence of SEQ ID NO: 160 or 161,
(b) a nucleic acid that hybridizes with a nucleic acid comprising the nucleotide sequence of SEQ ID NO: 160 or 161 under a stringent condition and encodes a protein that interacts with the c-Fos protein.

100. The inhibitor according to 99, wherein the nucleic acid comprises the nucleotide sequence of SEQ ID NO: 160 or 161.

101. A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising the amino acid sequence of SEQ ID NO: 96 or 97,
(b) a protein that comprises the amino acid sequence of SEQ ID NO: 96 or 97 including deletion, substitution or addition of one or several amino acid residues and interacts with a c-Fos protein,
(a') a nucleic acid comprising the nucleotide sequence of SEQ ID NO: 160 or 161,
(b') a nucleic acid that hybridizes with a nucleic acid comprising the nucleotide sequence of SEQ ID NO: 160 or 161 under a stringent condition and encodes a protein that interacts with a c-Fos protein.

102. The method according to 101, wherein the protein comprises the amino acid sequence of SEQ ID NO: 96 or 97.

103. The method according to 101, wherein the nucleic acid comprises the nucleotide sequence of SEQ ID NO: 160 or 161.

104. A method for screening for a prey that interacts with a bait, which comprises the step of detecting an interaction between the bait and a prey by the method according to any one of 101 to 103 and the step of selecting a prey for which an interaction is detected.

105. An inhibitor for an interaction between a protein that interacts with a c-Fos protein and the c-Fos protein, which comprises a protein of the following (a) or (b) as an active ingredient:
(a) a protein comprising the amino acid sequence of SEQ ID NO: 98 or 99,
(b) a protein that comprises the amino acid sequence of SEQ ID NO: 98 or 99 including deletion, substitution or addition of one or several amino acid residues and interacts with the c-Fos protein.

106. The inhibitor according to 105, wherein the protein as the active ingredient comprises the amino acid sequence of SEQ ID NO: 98 or 99.

107. The inhibitor according to 106, wherein the protein is a protein translated from a nucleic acid of the following (a) or (b):
(a) a nucleic acid comprising the nucleotide sequence of SEQ ID NO: 162 or 163,
(b) a nucleic acid that hybridizes with a nucleic acid comprising the nucleotide sequence of SEQ ID NO: 162 or 163 under a stringent condition and encodes a protein that interacts with the c-Fos protein.

108. The inhibitor according to 107, wherein the nucleic acid comprises the nucleotide sequence of SEQ ID NO: 162 or 163.

109. A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising the amino acid sequence of SEQ ID NO: 98 or 99,
(b) a protein that comprises the amino acid sequence of SEQ ID NO: 98 or 99 including deletion, substitution or addition of one or several amino acid residues and interacts with a c-Fos protein,
(a') a nucleic acid comprising the nucleotide sequence of SEQ ID NO: 162 or 163,
(b') a nucleic acid that hybridizes with a nucleic acid comprising the nucleotide sequence of SEQ ID NO: 162 or 163 under a stringent condition and encodes a protein that interacts with a c-Fos protein.

110. The method according to 109, wherein the protein comprises the amino acid sequence of SEQ ID NO: 98 or 99.

111. The method according to 109, wherein the nucleic acid comprises the nucleotide sequence of SEQ ID NO: 162 or 163.

112. A method for screening for a prey that interacts with a bait, which comprises the step of detecting an interaction between the bait and a prey by the method according to any one of 109 to 111 and the step of selecting a prey for which an interaction is detected.

113. An inhibitor for an interaction between a protein that interacts with a c-Fos protein and the c-Fos protein, which comprises a protein of the following (a) or (b) as an active ingredient:
(a) a protein comprising the amino acid sequence of SEQ ID NO: 100 or 101,
(b) a protein that comprises the amino acid sequence of SEQ ID NO: 100 or 101 including deletion, substitution or addition of one or several amino acid residues and interacts with the c-Fos protein.

114. The inhibitor according to 113, wherein the protein as the active ingredient comprises the amino acid sequence of SEQ ID NO: 100 or 101.

115. The inhibitor according to 113, wherein the protein is a protein translated from a nucleic acid of the following (a) or (b):
(a) a nucleic acid comprising the nucleotide sequence of SEQ ID NO: 164 or 165,
(b) a nucleic acid that hybridizes with a nucleic acid comprising the nucleotide sequence of SEQ ID NO: 164 or 165 under a stringent condition and encodes a protein that interacts with the c-Fos protein.

116. The inhibitor according to 115, wherein the nucleic acid comprises the nucleotide sequence of SEQ ID NO: 164 or 165.

117. A method for detecting an interaction between a bait and a prey, which comprises bringing the bait and the prey into contact and detecting a complex formed by the contact, wherein the bait is a protein of the following (a) or (b) or a protein translated from a nucleic acid of the following (a') or (b'):
(a) a protein comprising the amino acid sequence of SEQ ID NO: 100 or 101,
(b) a protein that comprises the amino acid sequence of SEQ ID NO: 100 or 101 including deletion, substitution or addition of one or several amino acid residues and interacts with a c-Fos protein,
(a') a nucleic acid comprising the nucleotide sequence of SEQ ID NO: 164 or 165,
(b') a nucleic acid that hybridizes with a nucleic acid comprising the nucleotide sequence of SEQ ID NO: 164 or 165 under a stringent condition and encodes a protein that interacts with a c-Fos protein.

118. The method according to 117, wherein the protein comprises the amino acid sequence of SEQ ID NO: 100 or 101.

119. The method according to 117, wherein the nucleic acid comprises the nucleotide sequence of SEQ ID NO: 164 or 165.

120. A method for screening for a prey that interacts with a bait, which comprises the step of detecting an interaction between the bait and a prey by the method according to any one of 117 to 119 and the step of selecting a prey for which an interaction is detected.

121. A protein of the following (a) or (b):
(a) a protein comprising the amino acid sequence of SEQ ID NO: 102,
(b) a protein that comprises the amino acid sequence of SEQ ID NO: 102 including deletion, substitution or addition of one or several amino acid residues and interacts with a c-Fos protein.

122. A nucleic acid encoding the protein according to 102.

123. A nucleic acid of the following (a) or (b):
(a) a nucleic acid comprising the nucleotide sequence of SEQ ID NO: 166,
(b) a nucleic acid that hybridizes with a nucleic acid comprising the nucleotide sequence of SEQ ID NO: 166 under a stringent condition and encodes a protein that interacts with a c-Fos protein.

124. An inhibitor for an interaction between a protein that interacts with a c-Fos protein and the c-Fos protein, which comprises the protein according to 121 or a protein translated from the nucleic acid according to 122 or 123 as an active ingredient.

125. A method for detecting an interaction between a bait and a prey, which comprises bringing the bait and the prey into contact and detecting a complex formed by the contact, wherein the bait is the protein according to 121 or a protein translated from the nucleic acid according to 122 or 123 as an active ingredient.

126. A method for screening for a prey that interacts with a bait, which comprises the step of detecting an interaction between the bait and a prey by the method according to 125 and the step of selecting a prey for which an interaction was detected.

127. A protein of the following (a) or (b):
(a) a protein comprising the amino acid sequence of SEQ ID NO: 103,
(b) a protein that comprises the amino acid sequence of SEQ ID NO: 103 including deletion, substitution or addition of one or several amino acid residues and interacts with a c-Fos protein.

128. A nucleic acid encoding the protein according to 127.

129. A nucleic acid of the following (a) or (b):
(a) a nucleic acid comprising the nucleotide sequence of SEQ ID NO: 167,
(b) a nucleic acid that hybridizes with a nucleic acid comprising the nucleotide sequence of SEQ ID NO: 167 under a stringent condition and encodes a protein that interacts with a c-Fos protein.

130. An inhibitor for an interaction between a protein that interacts with a c-Fos protein and the c-Fos protein, which comprises the protein according to 127 or a protein translated from the nucleic acid according to 128 or 129 as an active ingredient.

131. A method for detecting an interaction between a bait and a prey, which comprises bringing the bait and the prey into contact and detecting a complex formed by the contact, wherein the bait is the protein according to 127 or a protein translated from the nucleic acid according to 128 or 129 as an active ingredient.

132. A method for screening for a prey that interacts with a bait, which comprises the step of detecting an interaction between the bait and a prey by the method according to 131 and the step of selecting a prey for which an interaction was detected.

BRIEF EXPLANATION OF THE DRAWINGS

FIGS. 1A and 1B collectively show information of amino acid sequence, gene sequence and so forth of the protein of the present invention. Each of numerals within the parentheses after the DNA sequence numbers indicates the number of amino acid sequence encoded by it. A number having a sub-number means that the DNA encodes the same amino acid sequence, but has a different nucleotide sequence. SEQ ID NOS: 1 to 22 in FIG. 1A: Example 1, SEQ ID NOS: 47 to 76 in FIG. 1A and SEQ ID NOS: 77 to 103 in FIG. 1B: Example 2.

FIG. 5 (electrophoretic photographs) shows the result 2 of the verification of the interactions of the proteins and genes of the present invention and the nucleotide sequences thereof.
A: It was confirmed by the C-terminal labeling method in a wheat cell-free translation system that the proteins of SEQ ID NOS: 48 (Fip-cx.1), 75 (Fip-cx.2), 78 (Optn), 84 (Snapc5), 86 (C130020M04Rik), 88 (FLJ32000), 91 (Rit2), 93 (cytochrome b), 95 (Apoe), 97 (betaAPP), 99 (Hsp40), 101 (Fip-c10), 102 (Fip-c4) and 103 (Fip-c18) (FIGS. 1A and 1B) were expressed form the nucleic acid sequences of SEQ ID NOS: 105, 139, 142, 148, 150, 152, 155, 157, 159, 161, 163, 165, 166 and 167. Lanes 1 to 14: proteins of SEQ ID NOS: 48 (Fip-cx.1), 75 (Fip-cx.2), 78 (Optn), 84 (Snapc5), 86 (C130020M04Rik), 88 (FLJ32000), 91 (Rit2), 93 (cytochrome b), 95 (Apoe), 97 (betaAPP), 99 (Hsp40), 101 (Fip-c10), 102 (Fip-c4) and 103 (Fip-c18).
B: As a verification experiment of the interactions of the obtained proteins and c-Fos, direct interactions with c-Fos were confirmed by pull-down using C-terminal labeled proteins having the amino acid sequences of the proteins of SEQ ID NOS: 48 (Fip-cx.1) and 75 (Fip-cx.2) based on the nucleic acid sequences of SEQ ID NOS: 105 and 139. Lane 1: SEQ ID NO: 48 (Fip-cx.1), Lane 2: SEQ ID NO: 75 (Fip-cx.2), a and b: with and without bait c-Fos (Lanes 1 and 2: translation product and eluted fraction).

FIG. 9 shows configurations of a protein modified at the C-terminal (C-terminal labeled protein) (A), translation template of the present invention (B) and modification agent (C).

Figure 2:
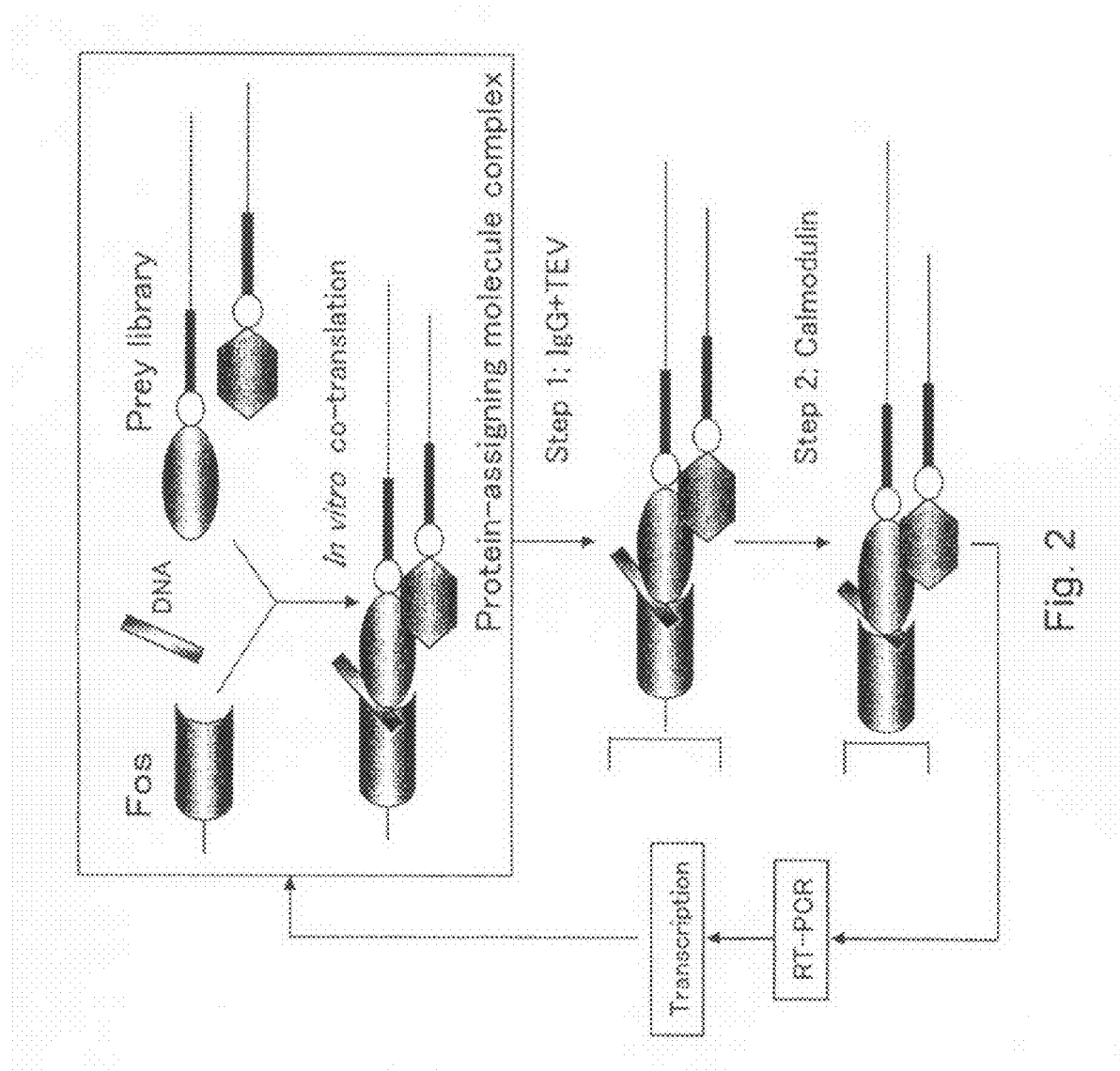
FIG. 2 shows the outline of the cotranslation screening method using an IVV random library, which is a method for detecting the proteins and genes of the present invention and the nucleotide sequences thereof. An IVV random library of mouse brain and c-Fos as a bait were used to carry out cell-free cotranslation screening, and the library after the screening was amplified by RT-PCR and then subjected to the cell-free cotranslation screening again with the bait. This procedure was repeated 3 times to detect the proteins and genes of the present invention and the nucleotide sequences thereof.

Both of bait as a part constituting the complexed bait and prey are translated in a cell-free translation system and interact to form a complex in the cell-free translation system. The prey may exist in a single number (I) or multiple number (II), and it may be a polypeptide itself obtainable by the translation in the cell-free translation system, or an assigning molecule (bound substance). Further, the complexed bait is not limited to the combination of a polypeptide translated in a cell-free translation system and DNA bait shown in the drawing, and it may be, for example, a combination of multiple or single polypeptide translated in a cell-free translation system and multiple or single bait coexisting in the cell-free translation system (e.g., DNA bait etc.), or the like.

Figure 12:
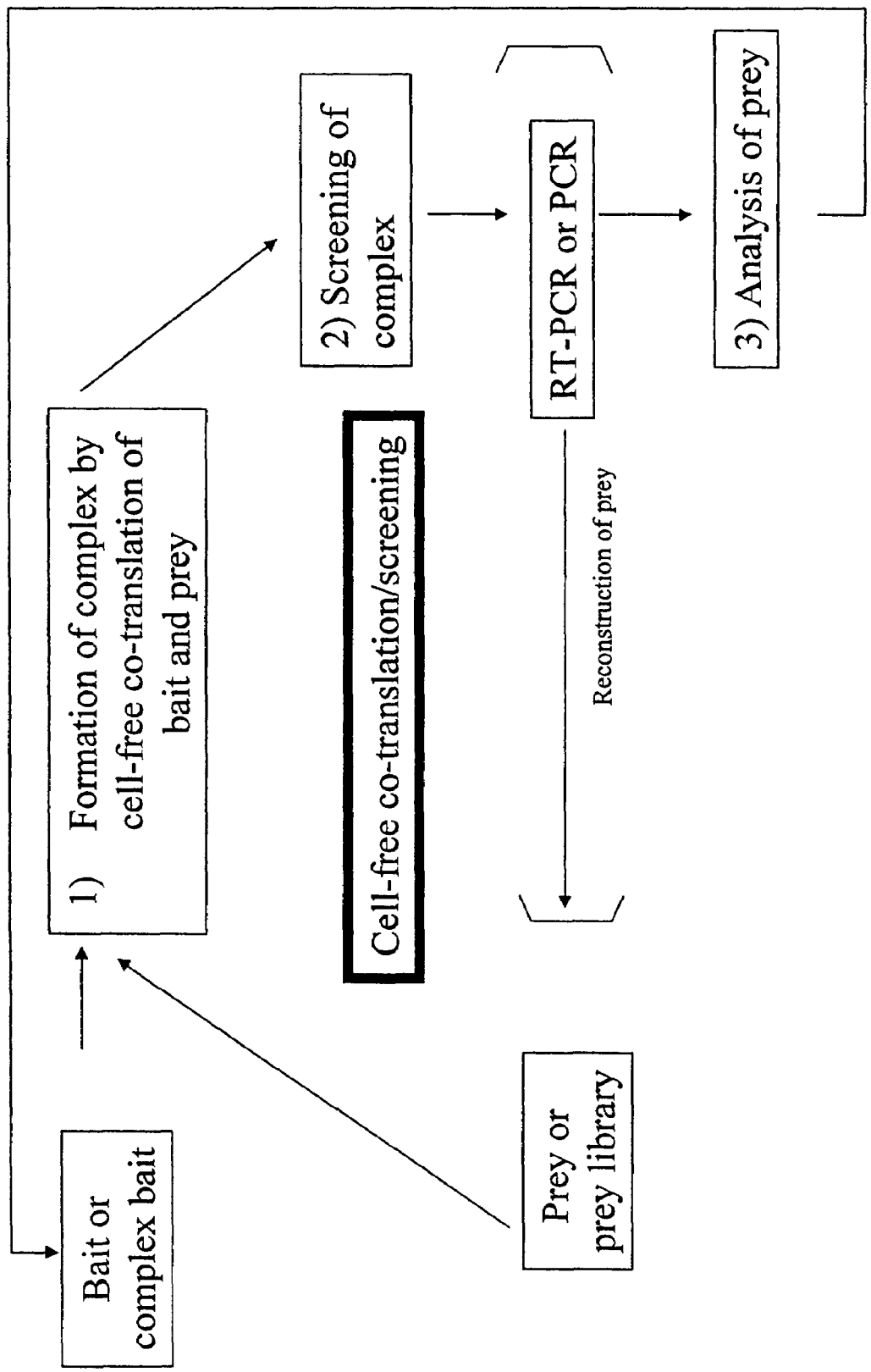

FIG. 12 shows outline of the method of screening for a complex based on cell-free cotranslation.

Figure 10:
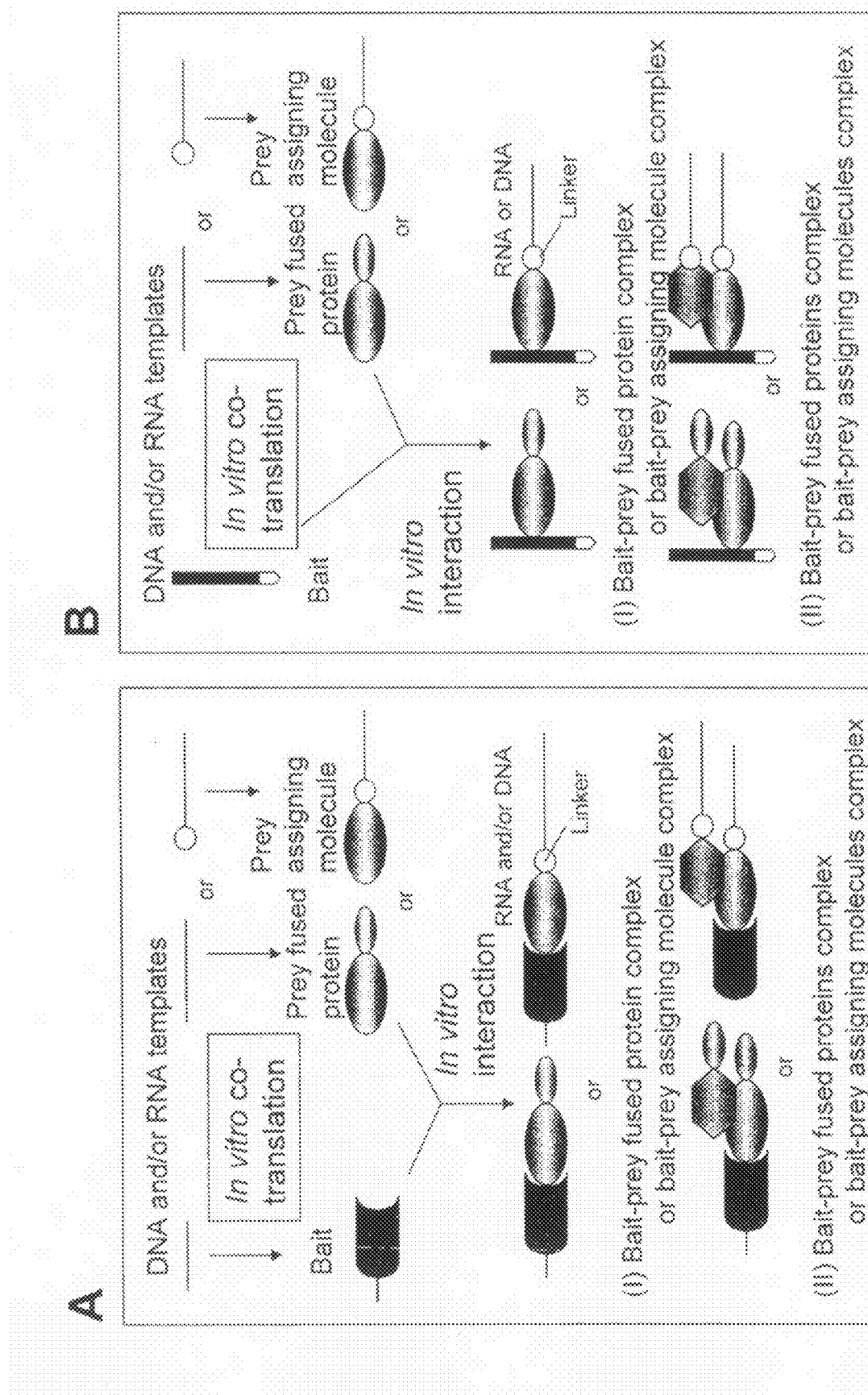
FIG. 10 shows outline of formation of a complex by cell-free cotranslation.
A: Both of bait and prey are translated in a cell-free translation system to interact with each other to form a complex in the cell-free translation system. The prey may exist in a single number (I) or multiple number (II), and it may be a polypeptide itself obtainable by the translation in the cell-free translation system, or an assigning molecule (bound substance).
B: In the presence of the bait, the prey is translated in a cell-free translation system to interact with the bait and thereby form a complex in the cell-free translation system. The prey may exist in a single number (I) or multiple number (II), and it may be a polypeptide itself obtainable by the translation in the cell-free translation system, or an assigning molecule (bound substance).
Figure 11:
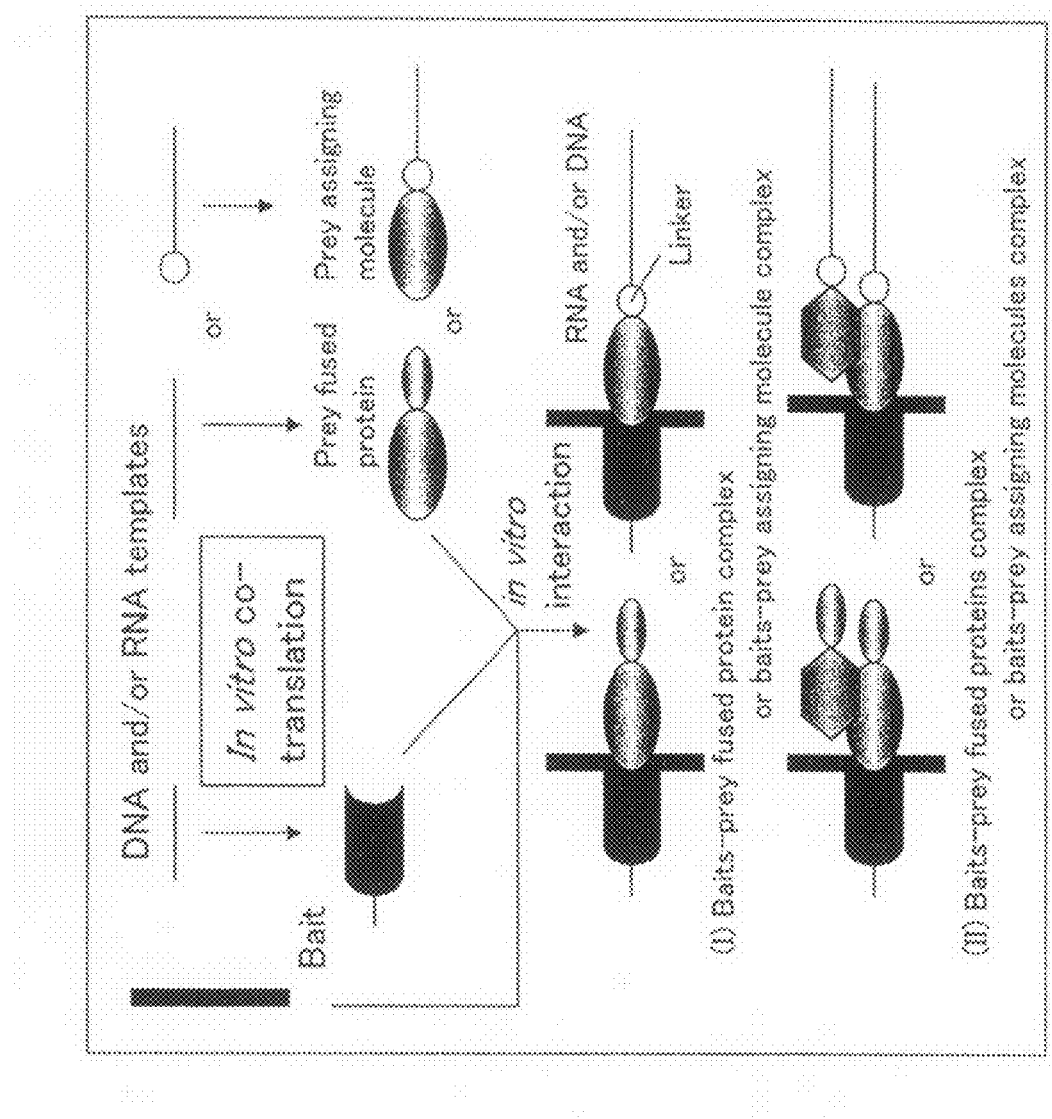
FIG. 11 shows outline of formation of a complex by cell-free cotranslation using a complexed bait.

By the step of forming a complex on the basis of cell-free cotranslation as shown in FIGS. 10 and 11 (1), the step of screening the prey of the complex (2), and the step of analyzing the prey (3), the cell-free cotranslation and screening can be realized totally in vitro. If the prey is an assigning molecule, and it exists in a multiple number, the screening can be repeated again from the step (1) by reconstructing mRNA or DNA encoding the prey by RT-PCR or PCR. Further, after analyzing the obtained prey, screening can be newly repeated from the step of (1) using the prey as a bait.

BEST MODE FOR CARRYING OUT THE INVENTION

<1> Proteins of the Present Invention

In this specification, proteins found to interact with c-Fos, including novel proteins, are called "the proteins of the present invention" for convenience of explanation.

The first group of the proteins of the present invention (SEQ ID NOS: 1 to 14 in FIG. 1A) consists of proteins both of which function of forming a complex with c-Fos and amino acid sequences are novel (Fos interacting protein chromosome X, Fip-cx). These proteins are proteins characterized by showing homology to the nucleotide sequence (275-829 bp)

formed by frame shift (+1) of the MAGE-necdin/trophinin complexes gene (AB032477) of the MAGE/necdin homologous region contained in the existing genome sequence WGS supercontig MmX (NW_042637) at nucleotide sequence level and the amino acid sequence thereof (184aa), and they are different from any of the proteins known so far to form a complex with c-Fos (Yurii Chinenov1 and Tom K Kerppola, Oncogene, 20, 2438-2452 (2001)). Further, the MAGE-necdin/trophinin complex is known to be a tumor-related gene existing in the X chromosome discovered as MAGE (melanoma-associated antigen) (Sakura S, et al., J. Biol. Chem., 276, 49378-49389 (2001)). However, as for the present protein Fip-cx, the frame shifts by +1 with respect to the gene sequence of MAGE-necdin/trophinin complex, and any frame shift in the MAGE-necdin/trophinin complex gene is not known. Therefore, the present protein Fip-cx is a protein novel for both of the amino acid sequence and function of interacting with c-Fos. It was confirmed that the amino acid sequence of the present protein Fip-cx contains a leucine zipper and directly interacts with c-Fos (FIG. 2).

The second group of the proteins of the present invention (SEQ ID NOS: 15 to 19 in FIG. 1A) consists of proteins of which function of interacting with c-Fos is novel. These proteins are proteins characterized by showing homology to the gene sequence of the existing eukaryotic translation elongation factor-1 delta (Eef1d, TEF-1; NM_023240) gene at gene sequence level and the amino acid sequence thereof, and they are different from any of the proteins that are known so far to form a complex with c-Fos. The function of forming a complex with c-Fos of the present protein Eef1d was detected by the present invention for the first time. Although Eef1d is known as a protein that controls translation extension, it has recently been shown that it is also a cancer- or tumor-related gene, and it is reported that with increase of the expression amount of Fos, the expression amount of Eef1d also increases as relationship of the translation factor Eef1d and tumor transformation (Joseph P, et al., J. Biol. Chem., 277, 6131-6136 (2002)). The amino acid sequences of these proteins contain a leucine zipper.

The third group of the proteins of the present invention (SEQ ID NOS: 20 to 22 in FIG. 1A) consists of proteins of which function of interacting with c-Fos is novel. These protein are proteins characterized by showing homology to the existing schwannomin interacting protein 1 (Schip1, NM_013928) gene sequence at gene sequence level and amino acid sequence thereof, and they are different from any of the proteins that are known so far to form a complex with c-Fos. Although it is known that Schip1 is a cancer- or tumor-related gene (Gouthebroze L, et al., Mol. Cell. Biol., 20, 1699-1712 (2000)), the function of forming a complex with c-Fos was detected for the first time by the present invention. These proteins bind with schwannomin, which is a regulator gene upstream from AP-1 and inhibits AP-1 activity. Further, the amino acid sequences of these proteins contain a leucine zipper.

The fourth group of the protein of the present invention (SEQ ID NOS: 47 to 56 in FIG. 1A) are proteins both of which function of forming a complex with c-Fos and amino acid sequences are novel (Fos interacting protein chromosome X.1, Fip-cx.1). These proteins are derived from (+1) frame-shifted gene of the Mage-d3 gene (NM_019548) of the Mage family. The amino acid sequences of these proteins contain a leucine zipper.

The fifth group of the proteins of the present invention (SEQ ID NOS: 57 to 76 in FIG. 1A) consists of proteins both of which function of forming a complex with c-Fos and amino acid sequences are novel (Fos interacting protein chromosome X.2, Fip-cx.2). These proteins are derived from (+1) frame-shifted gene of the Magphinin gene (AB032477) of the Mage family. The amino acid sequences of these proteins contain a leucine zipper.

The sixth group of the proteins of the present invention (SEQ ID NOS: 77 to 81 of FIG. 1B) consists of proteins of which function of interacting with c-Fos is novel. These proteins are proteins characterized by showing homology to the existing Optineurin gene sequence (Optn, NM_181848) at gene level and the amino acid sequence thereof, and they are different from any of the proteins that are known so far to form a complex with c-Fos. It is said that Optn is a causative gene of visual disturbance called adult-onset primary open-angle glaucoma (Tayebeh Rezaie, et al., Science, 295, 1077-1079 (2002)). The amino acid sequences of these proteins contain a leucine zipper.

The seventh group (SEQ ID NOS: 82 to 84 of FIG. 1B) of the proteins of the present invention consists of proteins of which function of interacting with c-Fos is novel. These proteins are proteins characterized by showing homology to the existing Snapc5 (Snpap19, XM_284503.1) gene sequence at gene sequence level and the amino acid sequence thereof, and they are different from any of the proteins that are known so far to form a complex with c-Fos. Snapc5 is one of the subunits of the SNAP complex that binds to PSE, which is a promoter of snRNA transcribed by pol II and pol III, to regulate transcription (Henry, R. W., Mittal, V., Ma, B., Kobayashi, R., Hernandez, N., Genes Dev. 12:2664-2672 (1998), PubMed ID: 9732265). The amino acid sequences of these proteins contain a leucine zipper.

The eighth group of the proteins of the present invention (SEQ ID NOS: 85 to 86 in FIG. 1B) consists of proteins of which function of interacting with c-Fos is novel. These proteins are proteins characterized by showing homology to the existing C130020M04Rik (BC026483) gene sequence at gene sequence level and the amino acid sequence thereof, and they are different from any of the proteins that are known so far to form a complex with c-Fos. C130020M04Rik is a gene of which protein frame is expected, but function is unknown. The annotation thereof is transcription regulatory factor. The amino acid sequences of these proteins contain a leucine zipper.

The ninth group of the proteins of the present invention (SEQ ID NOS: 87 to 89 in FIG. 1B) consists of proteins of which function of interacting with c-Fos is novel. These proteins are proteins characterized by showing homology to the existing FLJ3200 (XM_342896.1) gene sequence at gene sequence level and the amino acid sequence thereof, and they are different from any of the proteins that are known so far to form a complex with c-Fos. FLJ3200 is a gene of which protein frame is expected, but function is unknown. They are proteins having a sequence similar to that of *Rattus norvegicus*. The amino acid sequences of these proteins contain a leucine zipper.

The tenth group of the proteins of the present invention (SEQ ID NOS: 90 and 91 in FIG. 1B) consists of proteins of which function of interacting with c-Fos is novel. These proteins are proteins characterized by showing homology to the existing Rit2 (NM_009065.2) gene sequence at gene sequence level and the amino acid sequence thereof, and they are different from any of the proteins that are known so far to form a complex with c-Fos. Although Rit2 is an Ras-like protein, and it is a protein of the Ras family, it does not have a typical CAAX box existing at the C-terminal, which is known as a platform for the Ras protein on a membrane. It is known that Ras activates the promoter of the App gene (Ruiz-Leon, Y. and Pascual, A., 2, 278-285 (2001)). Furthermore, it is reported that Ras is involved in the control of the secretion process of the App protein together with Rho (Maillet, M et al., Nat. Cell Biol., 5, 633-639 (2003)). It has been reported that the Rho family consists of small GTP binding proteins and involved in cytoskeleton, transcription, development, transformation and so forth, and the Rho gene may stimulate the activity of AP1 to regulate a transcription factor involved in the activation of T cells (JIN-HONG CHANG, et al., Mil. Cell Biol., 18, 4986-4993 (1998)). The amino acid sequences of these proteins do not contain a leucine zipper.

The eleventh group of the proteins of the present invention (SEQ ID NOS: 92 to 93 in FIG. 1B) consists of proteins of which function of interacting with c-Fos is novel. These proteins are proteins characterized by showing homology to the existing cytochrome b (AF540912.1) gene sequence at gene sequence level and the amino acid sequence thereof, and they are different from any of the proteins that are known so far to form a complex with c-Fos. The registered cytochrome b gene is not cloned in the full length. The amino acid sequences of these proteins contain a leucine zipper.

The twelfth group of the proteins of the present invention (SEQ ID NOS: 94 and 95 in FIG. 1B) consists of proteins of which function of interacting with c-Fos is novel. These proteins are proteins characterized by showing homology to the existing apolipoprotein E (Apoe; NM_009696.2) gene sequence at gene sequence level and the amino acid sequence thereof, and they are different from any of the proteins that are known so far to form a complex with c-Fos. Apoe is known as a risk factor gene of Alzheimer's disease, and interacts with APP (David M. Holtzman, et al., PNAS, 97, 2892-97 (2000)). The Apoe gene has an AP1 site and is a gene existing downstream from AP1. The amino acid sequences of these proteins do not contain a leucine zipper.

The thirteenth group of the proteins of the present invention (SEQ ID NOS: 96 and 97 in FIG. 1B) consists of proteins of which function of interacting with c-Fos is novel. These proteins are proteins characterized by showing homology to the existing amyloid beta (A4) precursor protein (App; BC005499.1) gene sequence at gene sequence level and the amino acid sequence thereof, and they are different from any of the proteins that are known so far to form a complex with c-Fos. App is known as a risk factor gene of Alzheimer's disease, and interacts with Apoe (David M. Holtzman, et al., PNAS, 97, 2892-97 (2000)). Like the Apoe gene, the App gene has an AP1 site and is a gene existing downstream from AP1. In fact, it has been reported that the first cascade of the series of reactions at the time of formation of memory is expression of Fos/Jun, and App/Apoe is subsequently expressed at an early stage of memory formation (Steven P. R. Rose, Learning & Memory, 7, 1-17 (2000)). Furthermore, it has recently reported that App is folded during translation by cotranslation by means of the chaperon function of Apoe (cotranslational folding, Silke Hab and et al., J. Biol. Chem., 273, 13892-13897 (1998)). It can be said that this is an example of detection of the App/Apoe complex formed during cotranslation of IVV that further forms a complex with a bait Fos. The amino acid sequences of these proteins do not contain a leucine zipper.

The fourteenth group of the proteins of the present invention (SEQ ID NOS: 98 and 99 in FIG. 1B) consists of proteins of which function of interacting with c-Fos is novel. These proteins are proteins characterized by showing homology to the existing Dnaja2 (HSP40; BC003420) gene sequence at gene sequence level and the amino acid sequence thereof, and they are different from any of the proteins that are known so far to form a complex with c-Fos. Dnaja2 is a heat shock protein, and it is known that the expression amount thereof increases with increase of those of Fos and Jun when a heat shock is given (Kato N, et. al., Cancer Science, 97, 644-649 (2000)). The amino acid sequences of these proteins do not contain a leucine zipper.

The fifteenth group of the proteins of the present invention (SEQ ID NOS: 100 and 101 in FIG. 1B) consists of proteins of which function of interacting with c-Fos is novel. These proteins are proteins characterized by showing homology to the existing Fip-c10 (KIAA1209, XM_136911) gene sequence at gene sequence level and the amino acid sequence thereof, and they are different from any of the proteins that are known so far to form a complex with c-Fos. Fip-c10 is a gene of which protein frame is expected, but function is unknown. The amino acid sequences of these proteins do not contain a leucine zipper.

The sixteenth group of the proteins of the present invention (SEQ ID NO: 102 in FIG. 1B) consists of a protein both of which function of forming a complex with c-Fos and amino acid sequence are novel (Fos interacting protein chromosome 4.1, Fip-c4). This protein is encoded by a region in a genome sequence for which protein frame has not been expected at all so far. The amino acid sequence of this protein does not contain a leucine zipper.

The seventeenth group of the protein of the present invention (SEQ ID NO: 103 in FIG. 1B) is a protein both of which function of forming a complex with c-Fos and amino acid sequence are novel (Fos interacting protein chromosome 18, Fip-c18). This protein is encoded by a region in a genome sequence for which protein frame has not been expected at all so far. The amino acid sequence of this protein does not contain a leucine zipper.

Hereafter, the proteins of the present invention will be further explained.

Among the proteins of the present invention, the proteins having any one of the amino acid sequences of SEQ ID NOS: 1 to 22 and 47 to 103 are proteins for which it has been found that they interact with the c-Fos protein, i.e., form a complex, as described in the examples mentioned below. For proteins, existence of a mutant having the same function is generally expected. Further, by suitably modifying an amino acid sequence of a protein, a mutant having the same function can be obtained. Therefore, proteins that have any one of the amino acid sequences of SEQ ID NOS: 1 to 22 and 47 to 103 including deletion, substitution or addition of one or several amino acid residues and interact with the c-Fos protein also fall within the scope of the proteins of the present invention. Further, proteins that show a homology of 15% or more to any one of the amino acid sequences of SEQ ID NOS: 1 to 22 and 47 to 103 and interact with the c-Fos protein also fall within the scope of the protein of the present invention. Examples of such proteins of which amino acid residues are modified include, for example, proteins having any one of the amino acid sequences of SEQ ID NOS: 2 to 14 for the protein having the amino acid sequence of SEQ ID NO: 1, proteins having any one of the amino acid sequences of SEQ ID NOS: 16 to 19 for the protein having the amino acid sequence of SEQ ID NO: 15, and proteins having any one of the amino acid sequences of SEQ ID NOS: 21 and 22 for the protein having the amino acid sequence of SEQ ID NO: 20.

An amino acid sequence of a protein can be modified by modifying a nucleotide sequence of DNA encoding the protein using a well-known means such as site-directed mutagenesis and expressing DNA of which nucleotide sequence is modified. Among such modified proteins, those that interact with the c-Fos protein fall within the scope of the protein of the present invention. The interaction with the c-Fos protein can be measured by a known method for measuring an interaction, and examples include the method of detecting formation of a complex mentioned in the examples described later.

The proteins of the present invention may be fused with another protein and thus provided as a fusion protein.

The nucleic acids of the present invention are nucleic acids encoding the proteins of the present invention. The nucleic acids are usually RNA or DNA. Examples of the nucleic acids of the present invention include nucleic acids having any one of the nucleotide sequences of SEQ ID NOS: 23 to 40 and 104 to 167. These nucleic acids are nucleic acids of which nucleotide sequences were determined in the examples mentioned below. For a gene, existence of a gene encoding the same product, but having a different nucleotide sequence, or a gene encoding a mutant having the same function is expected. Further, by suitably modifying a nucleotide sequence, a gene encoding the same product or a mutant having the same function can be obtained. Therefore, nucleic acids having a nucleotide sequence similar to any one of the nucleotide sequences of SEQ ID NOS: 23 to 40 and 104 to 167 and encoding a protein that interacts with the c-Fos protein also fall within the scope of the nucleic acids of the present invention. Examples of such nucleic acids having a similar nucleotide sequence include nucleic acids that hybridize with a nucleic acid having a nucleotide sequence complementary to any one of the nucleotide sequences of SEQ ID NOS: 23 to 40 and 104 to 167 under a stringent condition, and nucleic acids having a nucleotide sequence showing a homology of 16% or more to any one of the nucleotide sequences of SEQ ID NOS: 23 to 40 and 104 to 167.

The stringent condition referred to here corresponds to, for example, that of hybridization using DIG Easy Hyb (Roche Diagnostics) at 42° C. followed by washing in 0.1×SSC/0.1% SDS for 15 minutes at 60° C. Homology of nucleotide sequences is obtained as a rate of number of nucleotides matching in alignment of the nucleotide sequences to be compared to the nucleotide number of the chain length of the nucleotide sequences. Further, homology of amino acid sequences is obtained as a rate of number of amino acid residues matching in alignment of the amino acid sequences to be compared to the amino acid number of the chain length of the amino acid sequences.

Whether a DNA encodes a protein that interacts with the c-Fos protein can be easily confirmed by expressing a protein from that DNA and confirming whether the expressed protein interacts with the c-Fos protein using the aforementioned method.

The nucleic acids of the present invention can be obtained by a conventional method on the basis of the elucidated nucleotide sequences. For example, it may be synthesized by a chemical synthesis method, or it may be obtained by RT-PCR using suitably designed primers from a mRNA prepared from cells or tissue expressing a protein that interacts with the c-Fos protein.

<2> Use of the Proteins of the Present Inventions and Others.

The proteins and genes of the present invention can be applied as an inhibitor that blocks transcription function, gene replication function and so forth as for c-Fos in gene therapy etc. by utilizing the novel function obtained by the nucleic acid sequences (function enabling binding with c-Fos in this case). The basis for this originates in the fact that the genes of the proteins of the present invention are detected after undergoing competitive process of screening repeated multiple times. Genes detected by this method exhibit a certain number distribution, and a gene having higher competitive power will be detected in a larger number. This means that a gene of which clones are detected by this method in a larger number should have a higher competitive power, and it more effectively functions as a blocking agent or inhibitor.

As for use of the proteins of the present invention and genes encoding them, as in vitro applications, they can be applied in, for example, evolutionary molecular engineering using a cell-free protein synthesis system or genomic function analysis by utilizing the novel function provided by the proteins, genes or nucleic acid sequences according to the present invention. In this case, analysis utilizing cotranslation screening and selection of assigning molecules is extremely effective. This is because the cotranslation screening/selection method makes it possible to comprehensively detect proteins that directly or indirectly interact with a bait protein. Furthermore, in analysis of interactions between IVVs, IVV and C-terminal labeled protein etc., they can also be use as a "target molecule (bait protein)". Examples of general methods for analyzing an interaction include, for example, microarray method, fluorescence correlation spectroscopy (FCS/FCCS), fluorescence imaging analysis, fluorescence resonance energy transfer method, evanescent-field molecular imaging method, fluorescence depolarization method, surface plasmon resonance method, enzyme linked immunosorbent assay and so forth. Specific examples of the cell-free protein synthesis system include wheat germ extract, rabbit reticulocyte lysate, *Escherichia coli* S30 extract and so forth. By adding a protein, gene or nucleic acid sequence as a translation template according to the present invention to any of these cell-free protein synthesis systems, simultaneously adding 1 to 100 μM of modification agent in the case of C-terminal labeling, and maintaining the system at 25 to 37° C. for 1 to several hours, a C-terminal modified protein is synthesized. In the case of assigning, only by adding a protein, gene or nucleic acid sequence as a translation template according to the present invention to the cell-free protein synthesis system and maintaining the system at 25 to 37° C. for 1 to several hours, an assigning molecule is synthesized.

Further, as for in vivo applications, by utilizing the novel function provided by the proteins, genes or nucleic acid sequences according to the present invention, for example, a protein modified for separation and labeled for detection (double modified protein) synthesized in a cell-free protein synthesis system can be used as it is for a subsequent purification process, detection process, or direct introduction into cells. Specific examples of cell expression system include any kind of cells of from bacteria such as *Escherichia coli, Bacillus subtilis* and thermophilic bacteria, yeast to cultured cells of insects, mammals and so forth, cells of threadworm, drosophila, zebra fish, mouse and so forth. By directly introducing the aforementioned C-terminal labeled or assigned double modified protein into these cells, an objective protein can be blocked. Alternatively, it is also possible to introduce the aforementioned gene or nucleic acid of the present invention and utilize the gene or nucleic acid as it is as an antisense sequence or RNAi sequence to block expression of an objective nucleic acid, or they can be expressed in a cell and utilized as a protein or assigning molecule to block a protein having an interacting action. When a protein is used in the C-terminal labeling method, by simultaneously introducing 1 to 100 μM modification agent for C-terminal labeling into cells using electroporation, microinjection or the like and maintaining the cells at the optimum growth temperature of the cells for several hours, a modified protein is synthesized. In the case of assigning, by introducing a template of an assigning molecule having the aforementioned gene or nucleic acid sequence of the protein of the present invention into cells and maintaining the cells at the optimum growth temperature of the cells for several hours, an assigning molecule is synthesized. The synthesized double modified protein can be collected by disrupting the cells and used for the subsequent purification process or detection process. Further, it can be used as it is in the cells for the detection process.

Hereafter, the use of the proteins of the present invention and others will be further explained.

The detection method of the present invention is a method of utilizing the proteins of the present invention as a bait in detection of interaction between the bait and a prey.

Preferably, the method is mainly characterized in that the bait and prey are modified for separation and labeled for detection in a specific manner, and the prey is produced by translation in a cell-free translation system in the presence of the bait to contact the bait and prey. In this specification, contacting a bait and a prey by producing the prey by translation in a cell-free translation system in the presence of the bait is also referred to as "cell-free cotranslation".

In this specification, the terms of "bait" and "prey" have the meanings usually used in the technical field of analysis of interaction between substances. That is, a protein, nucleic acid or the like as a known substance is called "bait", and a protein, nucleic acid or the like as a substance that interacts with the bait is called "prey". In the present invention, the prey is preferably a protein.

The bait used herein may be the protein of the present invention, or a complex constituted by arbitrary components including protein (including peptide), nucleic acid, or ligand such as antibody and hormone, metal and so forth, so long as it contains the protein of the present invention, and it may be a natural substance or artificial substance. The bait is not particularly limited as for the molecular weight and so forth. Examples include, for example, in the case of protein, a functional domain, a full-length protein containing a functional domain and so forth. If a prey library is used, use of full-length proteins enables comprehensive detection.

Further, as the prey, a protein is preferably used. The prey is not particularly limited as for the molecular weight and so forth.

Preferably, the detection method of the present invention is mainly characterized in that, in the detection of an interaction of the bait and prey, the bait and prey are modified for separation and labeled for detection in a specific manner, and cell-free cotranslation is performed as described above. Therefore, a preferred configuration of the detection method of the present invention may be the same as that of a usual method for detecting an interaction between a bait and a prey comprising contacting the bait and prey and detecting a complex formed by the contact, except that the bait and prey are modified for separation and labeled for detection in a specific manner, and cell-free cotranslation is performed.

Although the modification for separation and labeling for detection of the bait and prey are arbitrarily performed so that they are suitable for the detection of the complex, they should be performed so that both of the bait and prey should not be labeled with a label for detection or modified for separation. Therefore, the prey is used as a fusion protein with a protein that can be used as a label for detection or an assigning molecule, and the bait correspondingly has a modification for separation.

When the prey is used as a fusion protein, the bait should have a modification for separation. When the bait is a protein, the bait is preferably produced in a cell-free translation system by translation of mRNA encoding a fusion protein containing the bait as a fusion protein with a protein that can be used as a modification for separation in the cell-free translation system.

Examples of the modification for separation in the case where the bait is a protein include formation of a fusion protein with the GST protein, CBP used for the TAP method etc. (this can be separated by using affinity with calmodulin beads), protein A (this can be separated by using IgG-protein A affinity) as a protein, or any of various antibody tags etc. as an affinity tag. When the bait itself has a property that it can be used as a modification for separation, the bait can be used as it is as a bait having a modification for separation. Examples of the modification for detection of the prey include formation of a fusion protein with a fluorescent protein such as GFP (green fluorescent protein).

Preparation of mRNA encoding such a fusion protein mentioned above and translation of this mRNA in a cell-free translation system can be performed by usual methods. The mRNA may be mRNA produced by transcription of DNA in a cell-free transcription and translation system.

When the prey is an assigning molecule, arbitrary modification for separation can be added to the bait. When the bait is a protein, the aforementioned examples of the modification for separation can be used. In addition, when the bait is a nucleic acid, drug or the like, examples of the modification for separation include use of biotin etc. that interact with streptavidin or avidin. When the bait itself has a property that it can be used as modification for separation, the bait can be used it is as a bait having modification for separation.

An assigning molecule means a molecule assigning a phenotype and a genotype. The assigning molecule is usually a molecule comprising a genotype molecule containing a nucleic acid having a nucleotide sequence reflecting a genotype and a phenotype molecule containing a protein relating to expression of phenotype, which are bound to each other. By using a prey as this protein, the prey can be used as an assigning molecule. Such an assigning molecule can be formed by performing translation of mRNA encoding a prey in a cell-free translation system so that the translated prey should associate with the mRNA, or performing transcription and translation of DNA encoding a prey in a cell-free transcription and translation system so that the translated prey should associate with the DNA. Therefore, by allowing a bait to exist during the production, cell-free cotranslation can be attained. That is, the cell-free cotranslation can be performed by the following scheme (1) or (2).

(1) By performing translation of mRNA encoding the prey in the presence of the bait in a cell-free translation system so that the translated prey should associate with the mRNA, the prey is produced in the cell-free translation system, and thereby the bait and prey are brought into contact with each other.

(2) By performing transcription and translation of DNA encoding the prey in the presence of the bait in a cell-free transcription and translation system so that the translated prey should associate with the DNA, the prey is produced in the cell-free translation system, and thereby the bait and prey are brought into contact with each other.

Hereafter, the embodiments of (1) and (2) mentioned above will be explained.

In the embodiment of (1), the translated prey preferably associates with the mRNA, because the mRNA has a spacer region bound to the 3' end and a peptide acceptor region bound to the spacer region and containing a group that can bind to a peptide by transpeptidation reaction. Examples of the method for detecting an interaction using such an assigning molecule include the in vitro virus method.

The mRNA is preferably a nucleic acid containing a 5' untranslation region including a transcription promoter and a translation enhancer, an ORF region encoding a prey and binding to the 3' end side of the 5' untranslation region, and a 3' end region including a poly-A sequence and binding to 3' end side of the ORF region. Preferably, an expression amplification sequence containing an SNNS (S is G or C) sequence on the 5' end side of the poly-A sequence (for example, a sequence recognizable by the restriction enzyme XhoI) is further included. The mRNA may or may not have a Cap structure at the 5' end.

The poly-A sequence is a poly-A continuous chain of at least 2 or more residues comprising dA and/or rA as single kind of residues or mixture of two kinds, and the poly-A chain consists of, preferably 3 or more residues, more preferably 6 or more residues, still more preferably 8 or more residues.

One of the factors affecting the translation efficiency is a combination of the 5' UTR comprising a transcription promoter and a translation enhancer and the 3' end region including a poly-A sequence. The effect of the poly-A sequence of the 3' end region is usually exerted with a length of ten or less residues. As the transcription promoter of the 5' UTR, T7/T3, SP6, and so forth can be used, and no particular limitation is imposed. SP6 is preferred, and it is particularly preferable to use SP6, especially when a sequence containing an omega sequence or a part of omega sequence is used as the translation enhancer sequence. The translation enhancer is preferably a part of the omega sequence, and as the part of the omega sequence, one containing a part of the omega sequence of TMV (O29, refer to Gallie D. R., Walbot V., Nucleic Acids Res., vol. 20, 4631-4638 (1992), and WO02/48347, FIG. 3) is preferred.

Further, for the translation efficiency, the combination of the XhoI sequence and a poly-A sequence is preferred in the 3' end region. Furthermore, a combination of the downstream portion of the ORF region, i.e., the upstream region of the XhoI sequence having an affinity tag, and a poly-A sequence is preferred. The affinity tag sequence may be any sequence for utilizing a means that can detect a protein such as an antigen-antibody reaction, and no limitation is imposed. The affinity tag is preferably the Flag-tag sequence or His-tag sequence, which is a tag for affinity separation analysis based on an antigen-antibody reaction. As for the effect of the poly-A sequence, an affinity tag such as the Flag-tag attached with the XhoI sequence and further attached with a poly-A sequence increases the translation efficiency. As for the His-tag, even a His-tag having a configuration not containing the XhoI sequence also exhibits sufficient translation efficiency, and thus is effective.

Such a configuration effective for improvement of translation efficiency is also effective for assignment efficiency.

If SP6+O29 and Flag+XhoI+$A_n$ (n=8) or His+$A_n$ (n=8), for example, are used as the 5' UTR and the 3' end region, respectively, the 5' UTR and the 3' end region would have lengths of about 49 bp and about 38 or 26 bp, respectively, and thus they have such a length that they can be incorporated into primers for PCR as an adaptor region. Therefore, a coding region having such a 5' UTR and 3' end region can be easily produced by PCR from any of vectors, plasmids and cDNA libraries. In the coding region, translation may occur beyond the ORF region. That is, there may not be a stop codon at the end of the ORF region.

The peptide acceptor region is not particularly limited, so long as it can bind to the C-terminal of a peptide. For example, puromycin and 3'-N-aminoacylpuromycin aminonucleosides (PANS-amino acids) including PANS-amino acids corresponding to all amino acids such as PANS-Gly in which the amino acid portion is glycine, PANS-Val in which the amino acid portion is valine, and PANS-Ala in which the amino acid portion is alanine can be utilized. Further, 3'-N-aminoacyladenosine aminonucleosides (AANS-amino acids), in which a 3'-aminoacyladenosine and an amino acid are bonded via an amide bond as a chemical bond formed as a result of dehydration condensation of the amino group of the 3'-aminoacyladenosine and the carboxyl group of the amino acid, corresponding to all amino acids, for example, AANS-Gly in which the amino acid portion is glycine, AANS-Val in which the amino acid portion is valine, AANS-Ala in which the amino acid portion is alanine, and so forth can also be used. Furthermore, nucleosides and nucleosides bound with an amino acid via an ester bond can also be used. In addition, any of substances formed with a bonding scheme that can chemically bond a nucleoside or a substance having a chemical structure similar to that of nucleoside and an amino acid or a substance having a chemical structure similar to amino acid can be used.

The peptide acceptor region preferably comprises puromycin or a derivative thereof, or puromycin or a derivative thereof and one or two residues of deoxyribonucleotides or ribonucleotides. The term "derivative" used in this case means a derivative that can bind to the C-terminal of peptide in a protein translation system. The puromycin derivative is not limited to those having the total puromycin structure, and includes those having the puromycin structure a part of which is eliminated. Specific examples of the puromycin derivative include PANS-amino acids, AANS-amino acids and so forth.

Although the peptide acceptor region may have a structure consisting only of puromycin, it preferably has a nucleotide sequence comprising DNA and/or RNA of one or more residues at the 5' end side. As such a sequence, dC-puromycin, rC-puromycin, and so forth, more preferably, a CCA sequence comprising dCdC-puromycin, rCrC-puromycin, rCdC-puromycin, dCrC-puromycin or the like and imitating the 3' end of aminoacyl-tRNA (Philipps, G. R., Nature 223, 374-377 (1969)), is suitable. As for the type of nucleotide, preference is higher in the order of C>(U or T)>G>A.

The spacer region is preferably a PEG region containing polyethylene glycol as a main component. The spacer region usually contains, in addition to the PEG region, a donor region that can bind to the 3' end of a nucleic acid.

The donor region that can bind to the 3' end of nucleic acid usually consists of one or more nucleotides. The number of nucleotides is usually 1 to 15, preferably 1 to 2. The nucleotides may be a ribonucleotide or a deoxyribonucleotide. The donor region may have a modification substance.

The sequence of the 5' end of the donor region affects the ligation efficiency with the coding region encoding the prey. In order to attain ligation of the coding region and the spacer region, it is required to include at least one or more residues, and at least one residue of dC (deoxycytidylic acid) or two residues of dCdC (dideoxycytidylic acid) is preferred for an acceptor having a poly-A sequence. As for the type of nucleotide, preference is higher in the order of C>(U or T)>G>A.

The PEG region contains polyethylene glycol as a main component. The expression "contains polyethylene glycol as a main component" used herein means that the total number of nucleotides contained in the PEG region is 20 or less, or the average molecular weight of the polyethylene glycol is 400 or more. It preferably means that the total number of nucleotides is 10 or less, or the average molecular weight of the polyethylene glycol is 1000 or more.

The average molecular weight of the polyethylene glycol in the PEG region is usually 400 to 30,000, preferably 1,000 to 10,000, more preferably 2,000 to 8,000. If the molecular weight of the polyethylene glycol is lower than about 400, a posttreatment for assignment translation may be required for assignment translation of a genotype molecule containing the spacer region (Liu, R., Barrick, E., Szostak, J. W., Roberts, R. W., Methods in Enzymology, vol. 318, 268-293 (2000)). However, if PEG having a molecular weight if 1000 or more, preferably 2000 or more, is used, highly efficient assignment can be attained only by assignment translation, and therefore the posttreatment for the translation becomes unnecessary. Further, when the molecular weight of the polyethylene glycol increases, stability of the genotype molecule tends to increase, and in particular, the stability becomes favorable with a molecular weight of 1000 or more. If the molecular weight is 400 or less, properties thereof are not different so much from those of a DNA spacer, and it may become unstable.

By having a spacer region containing polyethylene glycol as a main component, it becomes possible to form an assigning molecule not only in a cell-free translation system of rabbit reticulocytes, but also in a cell-free translation system of wheat germ, the stability of the genotype molecule in both translation systems is markedly improved, and it becomes unnecessary to perform any treatment after the translation.

In the embodiment of (2), it is preferred that DNA encodes a fusion protein of a protein and streptavidin or avidin, DNA is labeled with biotin, and a translated prey associates with the DNA because transcription and translation is carried out in a state that one DNA molecule is contained in one compartment of emulsion. Examples of the method for detecting an interaction using such an assigning molecule include the STABLE method.

The emulsion is usually a W/O type emulsion formed by mixing two kinds of surface active agents, mineral oil and a reaction mixture of cell-free transcription and translation system. In order to form a W/O type emulsion, it is usually necessary for the surface active agents to have an HLB (hydrophile-lipophile balance) value of 3.5 to 6. The HLB value of mixed two kinds of surface active agents is calculated from the HLB values of the individual surface active agents by using a simple equation. For example, if Span 85 (HLB=1.8) and Tween 80 (HLB=15.0) are mixed in volumes of 40.2 µl and 9.8 µl, respectively, the mixture has an HLB value of 4.4. The ratio of the surface active agents and mineral oil is usually 1:18 (volume ratio). Further, the ratio of the reaction mixture is 1 to 50% (volume ratio) with respect to the whole emulsion, and it is usually 5%. The emulsion can be formed by adding the reaction mixture as several divided portions to a mixture of the surface active agents and mineral oil at a low temperature with stirring and mixing them. The reactions of transcription and translation can be started by raising the temperature of the emulsion.

The preparation of DNA encoding a prey, and transcription and translation of such a DNA in a cell-free transcription and translation system can be performed in a usual manner.

As described above, by labeling the bait and prey for detection and modifying them for separation in particular schemes, a complex formed by cell-free cotranslation can be specifically detected.

As for the cell-free cotranslation of a bait and a prey, the cell-free translation system (including cell-free transcription and translation system) in which the cell-free cotranslation is performed may be any of systems of *E. coli*, rabbit reticulocytes, wheat germs and so forth. Although formation of assigning molecules is quite unstable with *E. coli* in the in vitro virus method, it has been confirmed that it is stable in a system of rabbit reticulocytes (Nemoto N., Miyamoto-Sato E., and Yanagawa H., FEBS Lett. 414, 405 (1997); Roberts R. W., Szostak J. W., Proc. Natl. Acad. Sci. USA, 94, 12297 (1997)), and it has been further confirmed that it is still more stable in a system of wheat germ (Japanese Patent Laid-open No. 2002-176987). For the STABLE method, the system may be any of systems of *E. coli*, rabbit reticulocyte, wheat germ and so forth.

The conditions for the translation and transcription in the cell-free cotranslation are suitably selected depending on a cell-free translation system to be used.

The templates of the bait and prey added to the cell-free translation system may be either RNA or DNA, so long as the cell-free translation system is a cell-free transcription and translation also causing transcription.

Hereafter, an example of a translation template preferred for use as a bait will be explained.

Figure 8:
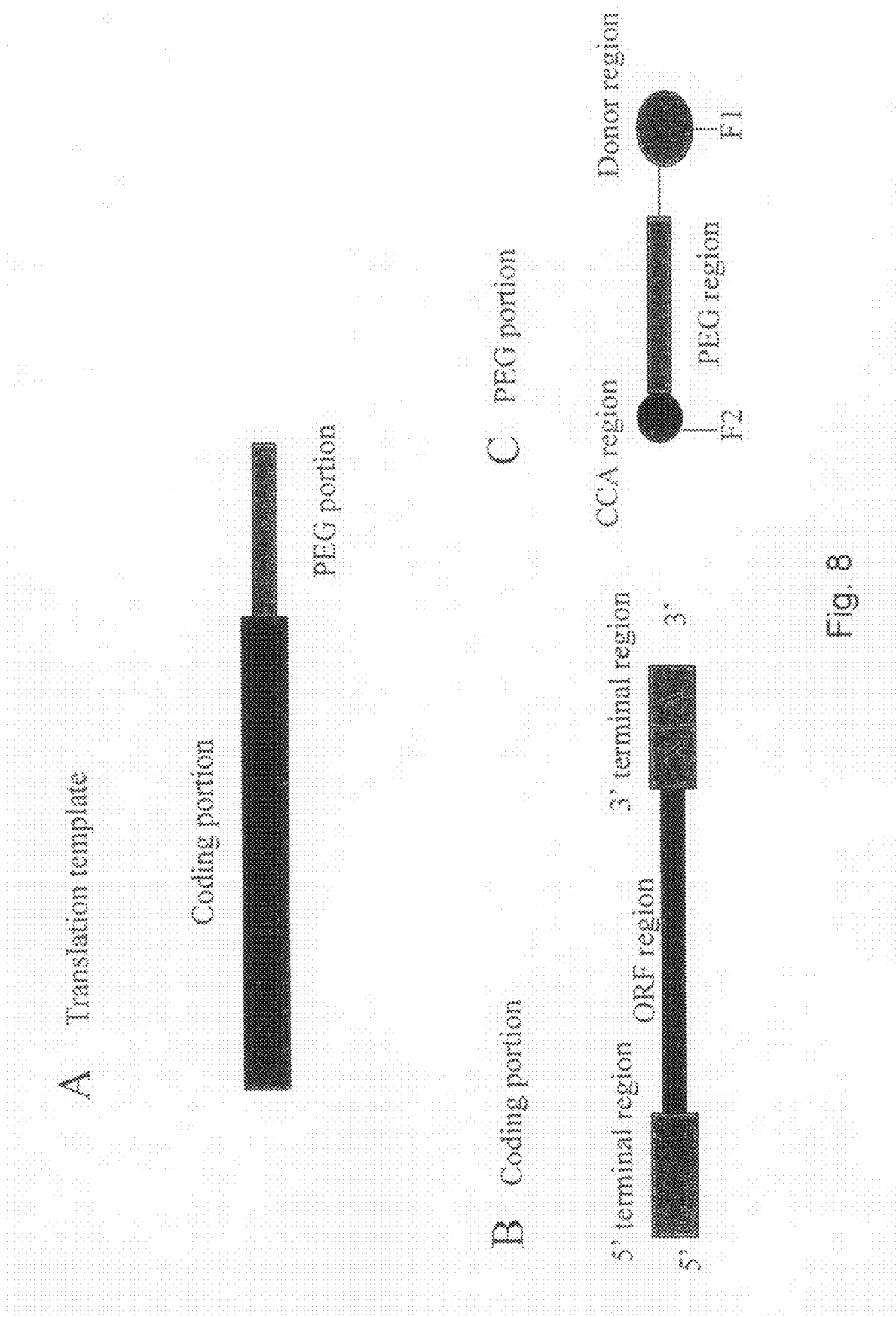
FIG. 8 shows configurations of a translation template (A) as well as a coding molecule (B) and spacer molecule (C), which are constituents of the template. The translation template consists of a coding portion derived from the coding molecule and a spacer portion derived from the spacer molecule. F1 and F2 represent a fluorescent dye.

As a bait used in the cotranslation screening of this embodiment, used is a translation template characterized by comprising a coding portion having information for translation into a protein and a PEG spacer portion as shown in FIG. 8. The coding portion has information for translation into a protein, and it may be any sequence. However, it is preferably characterized by having an acceptor (A sequence) in a 3' end region of the coding portion, or having an acceptor (A sequence) in a 3' end region of the coding portion and a translation amplification sequence (X sequence) 5'-upstream from the A sequence. It contains a short poly-A sequence as the A sequence of the coding portion. The short poly-A sequence is usually a sequence comprising 2 to 10 nucleotides of A. It is characterized by having a sequence having (C or G)NN(C or G) sequence, for example, a XhoI sequence, as the X sequence. The PEG spacer portion has a PEG region containing polyethylene glycol as a main component, a donor region for ligation with the coding portion, and a CCA region at the 3' end. Although the PEG spacer portion may consist only of the donor region or CCA region, it is preferably has a configuration comprising the PEG region containing polyethylene glycol as a main component. The CCA region is characterized by not having a function of binding by a transpeptidation reaction to a protein translated from the translation template. The PEG region is characterized by having a molecular weight of the polyethylene glycol of 500 or more. Further, it is characterized by containing at least one function-imparting unit (F) in the donor region and/or the CCA region. It is characterized in that the function-imparting unit (F1 and/or F2) immobilizes or labels with fluorescence the translation template and/or a protein translated from the translation template. As the immobilization substance, biotin and so forth are contemplated, and as the fluorescent substance, fluorescein, Cy5, rhodamine green (RhG) and so forth can be contemplated. The present invention relates to these coding portion, translation template, and libraries thereof, as well as a protein translated on a ribosome and library thereof.

The translation template of a bait (FIG. 8, A) comprises a coding portion derived from a coding molecule (FIG. 8, B) and a PEG spacer portion derived from a PEG spacer molecule (FIG. 8, C). In this embodiment, a PEG spacer portion can be ligated to the coding portion to improve stability thereof, and thus translation efficiency can be improved, basically regardless of the sequence of the coding portion. However, it is further possible to further improve the translation efficiency depending on the configuration of the coding portion or the type of the PEG spacer portion. The details thereof are described below.

The coding portion of this embodiment (FIG. 8, B) comprises a 5' end region, an ORF region, and a 3' end region, and it may or may not have a Cap structure at the 5' end. Further, the sequence of the coding portion is not particularly limited, and use thereof as one incorporated into any vector or plasmid can be contemplated. The 3' end region of the coding portion includes one having a poly-A x 8 sequence as the A sequence or one having, as the X sequence, the XhoI sequence or a sequence of SNNS(S is G or C) as a sequence of 4 or more nucleotides, and XA as a combination of the A sequence and X sequence. A configuration that a Flag-tag sequence is included as an affinity tag sequence upstream from the A sequence, X sequence, or XA sequence is contemplated. The affinity tag sequence used here may be a sequence for using any means that enables detection or purification of a protein, for example, those utilizing an antigen-antibody reaction such as HA-tag and protein A of IgG (z domain), His-tag, and so forth. As for factors affecting the translation efficiency, the combination of the XA sequence is important. The first four nucleotides of the X sequence are important, and one having a sequence of SNNS is preferred. Further, the 5' end region comprises a transcription promoter and a translation enhancer. As the transcription promoter, T7/T3, SP6, and so forth can be used, and no particular limitation is imposed. However, for a cell-free translation system of wheat, a sequence containing an omega sequence or a part of omega sequence is preferably used as the translation enhancer sequence, and SP6 is preferably used as the promoter. The part of the omega sequence is one containing a part of the omega sequence of TMV (O29, refer to Gallie D. R., Walbot V., Nucleic Acids Res., vol. 20, 4631-4638 (1992) and WO02/48347, FIG. 3). The ORF region of the coding portion may be any sequence comprising DNA and/or RNA. It may be a gene sequence, exon sequence, intron sequence, random sequence, or any natural sequence or artificial sequence, and the sequence is not limited.

The PEG spacer molecule of this embodiment (FIG. 8, C) comprises a CCA region, a PEG region, and a donor region. The minimum essential component is the donor region. As for the factors affecting the translation efficiency, one having not only the donor region but also the PEG region is preferred, and it preferably has puromycin which does not have an ability to bind with an amino acid. The molecular weight of the polyethylene glycol in the PEG region is 400 to 30,000, preferably 1,000 to 10,000, more preferably 2,000 to 6,000. Further, the CCA region may have a configuration including puromycin or a configuration not including puromycin. As puromycin, puromycin and 3'-N-aminoacylpuromycin aminonucleosides (PANS-amino acids) including PANS-amino acids corresponding to all amino acids such as PANS-Gly in which the amino acid portion is glycine, PANS-Val in which the amino acid portion is valine, and PANS-Ala in which the amino acid portion is alanine can be utilized. Further, 3'-N-aminoacyladenosine aminonucleosides (AANS-amino acids), in which a 3'-aminoacyladenosine and an amino acid is bonded via an amide bond as a chemical bond formed as a result of dehydration condensation of the amino group of the 3'-aminoacyladenosine and the carboxyl group of the amino acid, corresponding to all amino acids, for example, AANS-Gly in which the amino acid portion is glycine, AANS-Val in which the amino acid portion is valine, AANS-Ala in which the amino acid portion is alanine, and so forth can also be used. Furthermore, nucleosides and nucleosides bound with an amino acid via an ester bond can also be used. In addition, any of substances formed with a bonding scheme that can chemically bond a nucleoside or a substance having a chemical structure similar to that of nucleoside and an amino acid or a substance having a chemical structure similar to amino acid can be used. For this translation template, any substances corresponding to the aforementioned puromycin derivatives of which amino group lacks the ability to bind to an amino acid, and a CCA region lacking puromycin are also contemplated. However, by incorporating puromycin that cannot bind with a protein on a ribosome, the translation efficiency can be further enhanced. Although the reason for this is not certain, it may possible that puromycin that cannot bind with a protein stimulates a ribosome to enhance the turnover. A nucleotide sequence comprising DNA and/or RNA of one or more residues is preferably contained on the 5' end side of the CCA region (CCA). As for the type of nucleotide, preference is higher in the order of C>(U or T)>G>A. As such a sequence, dc-puromycin, rc-puromycin, and so forth, more preferably, a CCA sequence comprising dCdC-puromycin, rCrC-puromycin, rCdC-puromycin, dCrC-puromycin or the like and imitating the 3' end of aminoacyl-tRNA (Philipps, G. R., Nature 223, 374-377 (1969)) is suitable. In one embodiment of the present invention, these puromycins are made incapable of binding with an amino acid in a certain manner.

The PEG spacer portion of this embodiment may have a configuration containing a modification substance (F1 and/or F2). With this characteristic, it can be used as a tag for collection, reuse by purification, or immobilization of translation template. Those comprising at least one residue of nucleotide of DNA and/or RNA incorporated with any of various separation tags such as fluorescent substance, biotin, and His-tag may be possible. Further, if SP6+O29 and Flag+XhoI+An (n=8) are used as the 5' end region and the 3' end region of the coding portion, respectively, for example, the lengths of the 5' end region and the 3' end region are about 60 bp and about 40 bp, respectively, and thus they have such a length that they can be designed in primers for PCR as an adaptor region. This provides a novel advantage. That is, it becomes possible to easily prepare a coding portion having a 5' end region and 3' end region according to this embodiment by PCR from any vector, plasmid, and cDNA library, and by ligating the PEG spacer portion, instead of a 3' UTR, to this coding portion, a translation template showing a high translation efficiency can be obtained.

The ligation of the PEG spacer molecule and the coding molecule according to this embodiment may be attained any method such as usual methods utilizing a DNA ligase or those based on a photoreaction, and the method is not particularly limited. In the ligation using an RNA ligase, as factors in the coding portion affecting the ligation efficiency, the A sequence of the 3' end region is important. It is a poly-A continuous chain consisting of at least two, preferably 3 or more, more preferably 6 to 8, of single kind or mixed kinds of residues selected from dA and/or rA. The DNA and/or RNA sequence of the 5' end of the donor region of the PEG spacer portion affects the ligation efficiency. In order to ligate the coding portion and PEG spacer portion with an RNA ligase, it is required to contain at least one or more residues, and for an acceptor having a poly-A sequence, at least 1 residue of dC (deoxycytidylic acid) or two residues of dCdC (dideoxycytidylic acid) is preferred. As for the type of nucleotide, preference is higher in the order of C>(U or T)>G>A. Furthermore, it is preferable to add polyethylene glycol of the same molecular weight as the PEG region during the ligation reaction.

Hereafter, an example of a translation template preferably used as a prey will be explained.

As a prey in cotranslation screening according to this embodiment, a protein of which C-terminal is modified with a translation template as represented in FIG. 9 (i.e., assigning molecule) is used. The translation template comprises a coding portion having information for translation into a protein and a PEG spacer portion. The coding portion has an A sequence at the 3' end, and the A sequence comprises a short poly-A sequence. The PEG spacer portion is characterized in that polyethylene glycol in the PEG region containing polyethylene glycol as a main component has a molecular weight of 400 or more, and the donor region and/or the CCA region contains at least one modification substance (F1 and/or F2). Further, the CCA region is characterized by having a function of binding by transpeptidation to a protein translated from the translation template, and the CCA region typically has puromycin. Further, it is characterized in that the modification substance (F1 and/or F2) immobilizes or labels with fluorescence the translation template and/or a protein translated from the translation template. As the immobilization substance, biotin and so forth are contemplated, and as the fluorescent substance, fluorescein, Cy5, rhodamine green (RhG) and so forth can be contemplated. The present invention relates to these coding portion, translation template, and libraries thereof, as well as a protein synthesized by translation on a ribosome (i.e., assigning molecule) and a library of such proteins (i.e., assigning molecules).

The prey is a protein synthesized by translation utilizing the translation template, of which C-terminal is modified with the translation template (FIG. 9, A, assigning molecule), and has characteristics in the translation template (FIG. 9, B) and the configuration of a protein of which C-terminal is modified with PEG (FIG. 9, C). It will be described in detail below.

The PEG spacer portion of the translation template (FIG. 9, B) is the same as that of the aforementioned translation template preferred for use as an bait except that it is characterized in that puromycin can bind with an amino acid. Further, the coding portion is also the same as that of the aforementioned translation template preferred for use as a bait. However, as for a configuration suitable for assignment, in particular, it is important to use an A sequence as the 3' end region, and this markedly increase the assignment efficiency of the total proteins and markedly decrease the amount of free proteins. Also in this case, if SP6+O29 and Flag+XhoI+An (n=8) are used as the 5' end region and the 3' end region of the coding portion, respectively, for example, the lengths of the 5' end region and the 3' end region are about 60 bp and about 40 bp, respectively, and thus they have such a length that they can be designed in primers for PCR as an adaptor region. This makes it possible to easily prepare a coding portion having a 5' end region and 3' end region according to this embodiment by PCR from any vector, plasmid, and cDNA library, and by ligating the PEG spacer portion, a translation template showing a high assignment efficiency can be obtained.

When the cording portion of the protein of which C-terminal is modified with PEG according to this embodiment (FIG. 9, C) is not used in detection of an interaction of proteins, i.e., when the protein is use for, for example, FCCS measurement, fluorescence reader, protein chip, and so forth, it may be intentionally cleaved with an RNase A or the like. By the cleavage, difficulty of detection of an interaction between proteins due to inhibition by the coding portion can be eliminated. Further, it is also possible to immobilize such a simple assigning molecule on a plate, bead, or slide glass.

The cell-free cotranslation will be explained with reference to FIG. 10. As shown in FIG. 10, a prey is translated in vitro in the presence of a bait. As shown in FIG. 10, A and B, there are a case where the bait is a protein, and it is translated simultaneously with the prey in a cell-free translation system, and a case where the bait is a nucleic acid, hormone or the like, and it is added to a cell-free translation system. As shown in FIG. 10, the prey is made into a fusion protein or assigning molecule.

The complex may be formed by binding of a bait and one prey (I), or by binding of another prey to a prey binding to a bait (II).

Because the detection method of the present invention enables in vitro formation of the complex, interactions between proteins, nucleic acid and protein, and so forth can be consistently detected in vitro.

When the bait is a protein, examples of the bait include a protein consisting only of a functional domain for an interaction with an objective protein, a protein including a functional domain, a protein of full length, and so forth. If a protein of full length is used, it is expected that it has multiple functional domains, and therefore it favorably becomes possible to more comprehensively detect preys. The protein of full length may be a single protein having a full length, or an assembly of two or more baits from which a protein of full length can be reconstructed.

The bait may be a complex as shown in FIG. 11, and this is called "complexed bait". By using such a complex, nonspecific adsorption can be further reduced, and it becomes possible to more comprehensively detect preys as the same effect as that of the full length protein.

As described above, as a complex contemplated for the cell-free cotranslation, a complex of a single bait and a single prey, a complex of a complexed bait and a prey, a complex of a bait and multiple preys, and a complex of a complexed bait and multiple preys are possible. Therefore, an interaction detectable by the detection method of the present invention includes not only a direct interaction between a bait and a prey, but also an indirect interaction for forming a complex.

It is considered that the most important factor in the cell-free cotranslation according to the present invention is that a protein is folded in a native state and in an undenatured state immediately after translation, a bait and a prey, a bait and another bait, or a prey and another prey, which should interact with each other, should coexist in a cell-free translation system, and thus they can promptly interact with each other. This is supported by the fact that a more superior result could be obtained by cotranslation compared with separate translation followed by coexistence by mixing. That is, it is considered that this is because a protein translated in vitro in a native folding state can encounter a protein, nucleic acid or the like, and therefore prompt formation of a complex by an interaction becomes possible.

The conventional methods of detecting an interaction require expression in E. coli and purification of a bait in a large amount. For example, when an interaction of a bait and a prey is expressed in a cell by the TAP method or the like, at least one month of preparation is needed. Further, the mRNA displaying method employing the pull-down method based on a GST fusion protein has problems that it takes at least 2 or 3 weeks because of the large amount expression in E. coli and purification of the bait, a substance that cannot be expressed in E. coli cannot be used as the bait, and so forth, and it further requires addition of bait in an amount 50 to 100 times the amount of prey to cause interaction with the prey. In the cell-free cotranslation, it becomes that only addition of almost equal weight of mRNA or DNA template to a cell-free translation system is sufficient, and it becomes completely unnecessary to express the bait in cells. Thus, the operation time can be markedly shortened. Furthermore, with a complexed bait or full length protein, an interaction of a bait and a prey can be further enhanced and made specific, and thus detection of nonspecific bonds can be avoided. Further, by using a complexed bait, a larger number of preys that interact with the second bait thereof can be comprehensively analyzed.

Although no system realizing complex formation by an interaction and screening consistently in vitro has existed so far, by performing translation and screening including those for a bait completely in vitro according to the detection method of the present invention described above, a system that can comprehensively detect interactions between proteins or between a protein and a nucleic acid with avoiding nonspecific detection can be constructed. Therefore, the present invention also provides a screening method utilizing the detection method of the present invention.

The screening method of the present invention is characterized by forming complexes by interactions of a bait and preys during cell-free cotranslation, and analyzing a prey that interacts with the bait by screening of the complexes. Therefore, the screening method of the present invention may be the same as an ordinary screening method for a prey that interacts with a bait comprising the detection step of detecting an interaction between a bait and prey and the selection step of selecting a prey for which an interaction is detected, except that the method comprises the detection step of detecting an interaction between a bait and a prey by the detection method of the present invention.

The screening method of the present invention further comprises the preparation step of preparing a prey selected in the selection step, and it is preferable to repeat the detection step, selection step and preparation step by using the prepared prey instead of or together with the bait used in the detection step. In this embodiment, the method is constituted by, for example, 1) the step of cell-free cotranslation in a cell-free translation system in which a prey and a bait cause an interaction, 2) the step of screening for detecting a prey interacting with the bait, 3) the step of examining and analyzing the prey, and 4) the step of repeating the steps from 1) by using the prey examined and analyzed in 3), as shown in FIG. 12. The steps of 1) and 2) correspond to the detection step and selection step, and the step of 3) corresponds to the preparation step. That is, the step of contacting a prey to the bait in the detection step corresponds to the step of the cell-free cotranslation, and the steps of detecting and selecting a complex in the detection step correspond to the step of screening.

In the screening method of the present invention, the prey selected in the selection step may be used again in the detection step.

In the screening method of the present invention, the cell-free cotranslation may be performed with a bait and a prey library, which is a group of multiple preys, so that two or more preys may be detected in the step of screening.

As shown in FIG. 11, a complexed bait and a prey may coexist, and a complex of the complexed bait and the prey may be formed by an interaction. By using a prey library in this cell-free cotranslation so that multiple kinds of preys of the prey library should coexist with the bait, and multiple complexes of the preys with the bait should be formed by interactions, multiple kinds of preys that interacts with the bait can be simultaneously and comprehensively detected in the screening. Further, if a full length protein is used as the bait, it becomes possible to comprehensively detect a larger number of preys, because a full length protein generally contains multiple functional domains for interactions.

Furthermore, as shown in FIG. 11, by forming multiple complexes of preys that interact with a complexed bait, multiple preys that interact with the complexed bait can be detected, and the second bait serves as a reinforcer of the interaction of a bait and a prey to realize a more specific interaction, which makes it possible to avoid nonspecific detection in the comprehensive detection. In evolutionary molecular engineering techniques such as the vitro virus method and the STABLE method, the prey is an assigning molecule (fusion). In the formation of complexes using a prey library or multiple kinds of preys, the preys may or may not directly interact with the bait.

When the complex obtained by the screening of complexes is an assigning molecule, a prey forming the complex may be detected by RT-PCR or PCR, and the screening may be performed again by using the PCR product as a prey (reconstruction of prey) or by using a prey analyzed from the PCR product as a new succeeding bait, as shown in FIG. 12. The method of performing the screening again by using the PCR product or performing screening by using a prey analyzed from the PCR product as a new succeeding bait can be performed only in the evolutionary molecular engineering techniques such as the in vitro virus method and the STABLE method, and cannot be carried out in a method of directly analyzing a protein such as the pull-down method and the TAP method.

When an assigning molecule is used, gene sequence of a proteinic prey can be known by RT-PCR or PCR after the screening. As shown in FIGS. 10 and 11, the proteinic prey referred to above is a prey interacting with a bait, a prey interacting that prey or the like, and all multiple kinds of preys interacting a bait can be comprehensively analyzed. When rescreening of a prey is further necessary, a DNA template, which is a product of RT-PCR or PCR, is transcribed, and the same cycles are repeated. Further, when a prey is determined by RT-PCR or PCR and the following sequence, it becomes possible to use that proteinic prey as a bait. If two or more kinds of preys that interact with the first bait are found, it becomes possible to form a complexed bait, and thus it becomes possible to detect a further larger number of preys.

If the cell-free cotranslation is used, it becomes possible to detect an interaction between proteins consistently in vitro even in the pull-down method or the TAP method. However, the assigning molecule is not formed in the TAP method, and therefore proteins must be directly analyzed in the analysis of preys. Then, if the pull-down method or the TAP method is used as the screening method in the in vitro virus method or the STABLE method, an assigning molecule is formed, and therefore gene sequence of a prey that causes interaction can be easily detected by RT-PCR or PCR in the analysis of the prey. Furthermore, if the cell-free cotranslation is used, it becomes possible to detect interactions between proteins consistently in vitro in the in vitro virus method or the STABLE method. Further, the number of preys is extremely large, the range of candidate preys can be narrowed down by rescreening performed by repeating the cycles. Further, the analyzed prey can be used as a bait in the next analysis, and if the number of preys increases, complexing of the bait advances, which results in detection of further preys. As described above, use of a prey as a bait in the subsequent cycle can be easily realized only in the in vitro virus method, STABLE method and so forth, which use an assigning molecule. However, the mRNA display method and the like requires synthesis in *E. coli* and purification of a large amount of GST fusion protein as a new bait, and thus preparation of the bait takes time, which makes the method difficult. If the cell-free cotranslation is used, such procedures are unnecessary, and the cycles can be easily repeated.

In the screening of complexes after the cell-free cotranslation, it is preferred that preys can be screened comprehensively without breaking the complexes produced by the cell-free cotranslation. For this purpose, a device for immobilization may be imparted to the bait with an affinity tag or the like so as to detect a prey that interacts with the bait. Any kind of such a device for immobilization may be used. Examples include, for example, a method of performing two-stage screening using IgG-protein A affinity or calmodulin beads as in the conventional TAP method, and a method of performing one or two-stage screening using streptavidin or avidin/biotin affinity, GST-tag, Flag-tag, T7-tag, His-tag or the like as in the pull-down method.

Examples of the prey library include a cDNA library (random priming library, dT priming library), random library, peptide library, hormone library, antibody library, ligand library, pharmaceutical compound library, and so forth, and any kind of library may be used. For example, if a random priming cDNA library is used as the prey library, although a full length prey cannot be expected for this library, a prey containing a functional domain can be expected. If such a library is used especially for screening using combinations with a complexed bait or full length protein, it becomes effective for comprehensive detection of preys.

Examples of the random priming library include cDNAs obtained by random priming and incorporated into multicloning sites (MCS) of vectors having a 5' untranslation region (UTR) containing the promoter of the RNA polymerase of SP6 (SP6) as a transcription promoter and a part of TMV omega sequence (O29) of the tobacco mosaic virus as a translation enhancer on the 5' end side of MCS, and containing a sequence for the Flag-tag, which is a tag for affinity separation analysis based on an antigen-antibody reaction, as an affinity tag sequence on the 3' end side of MCS, so that the Flag-tag should be added to the C-terminal of a protein expressed from an insert sequence incorporated into MCS.

The aforementioned detection method of the present invention includes the step of contacting a bait and a prey to form a complex. Therefore, a method of forming a complex of a bait and a prey that interacts with the bait is provided according to this step.

The formation method of the present invention is characterized by using the protein of the present invention as a bait in the formation of a complex of a bait and a prey, which is a protein that interacts with the bait, and preferably further labeling the bait and prey for detection and modifying them for separation in particular schemes, to perform cell-free cotranslation. Therefore, a preferred configuration of the formation method of the present invention may be the same as that of an ordinary method of forming a complex of a bait and a prey comprising contacting a bait and a prey that interacts with the bait, except that the bait and prey are labeled for detection and modified for separation in particular schemes, and the cell-free cotranslation is performed. The labeling for detection and modification for separation of the bait and prey in particular schemes as well as the cell-free cotranslation may be the same as those explained for the detection method of the present invention.

In the formation method of the present invention, not only a complex of a bait and a prey, for which interaction is known, but also a complex comprising elements for which interaction is unknown can be formed by performing the step of contacting the bait with a prey that interacts with the bait by contacting a bait with a prey library consisting of multiple kinds of preys.

Other methods for utilizing the protein of the present invention include the followings:

a method for analyzing an interaction between a protein and a substance, which is performed by fluorescence correlation spectroscopy, fluorescent imaging analysis method, fluorescence resonance energy transfer method, evanescent field molecular imaging method, fluorescence depolarization method, surface plasmon resonance method or enzyme linked immunosorbent assay using the protein of the present invention, a method for detecting an interaction between a protein and a substance, which uses the protein of the present invention and detects the interaction by amplification of a nucleotide sequence of a coding portion bound to the C-terminal of the protein of the present invention, a method for detecting an interaction between a protein and a substance, which uses the protein of the present invention and uses the cell-free cotranslation method or the cell-free cotranslation screening method, a method for detecting an interaction between a protein and a substance, which uses the protein of the present invention and labels the protein with fluorescence and/or immobilizes the protein, a method for analyzing an interaction of a protein or substance in vitro by using the protein of the present invention, a method for analyzing an interaction of a protein or substance, which uses the protein of the present invention, and utilizes the cotranslation method in vitro, a method for analyzing an interaction of a protein or substance in vivo by using the protein of the present invention, and the aforementioned methods for analyzing an interaction, which uses a nucleic acid encoding the protein of the present invention.

Further, the followings are also mentioned:

a method for analyzing an interaction between a protein and a target molecule, which uses a C-terminal modified protein comprising the protein and a modification agent binding to the C-terminal of the protein. The analysis of the interaction can be carried out by fluorescence correlation spectroscopy, fluorescent imaging analysis method, fluorescence resonance energy transfer method, evanescent field molecular imaging method, fluorescence depolarization method, surface plasmon resonance method or enzyme linked immunosorbent assay. The C-terminal modified protein may be immobilized. The C-terminal modified protein may be added on an array on which the target molecule is immobilized, and then the C-terminal modified protein specifically binding to the target molecule may be detected.

In the analysis method of this embodiment, the interaction is usually analyzed by contacting the modified protein of the present invention obtained above and the target molecule in a suitable combination selected depending on the type of the modification substance or reaction system and measuring change of a signal generated by the interaction between the modified protein and the target molecule among signals generated by the modified protein or the target molecule. The analysis of the interaction is carried out by, for example, fluorescence correlation spectroscopy, fluorescent imaging analysis method, fluorescence resonance energy transfer method, evanescent field molecular imaging method, fluorescence depolarization method, surface plasmon resonance method or enzyme linked immunosorbent assay. The details of these methods are explained below.

The "target molecule" means a molecule that interacts with the modified protein of the present invention, and it may be specifically a protein, nucleic acid, sugar chain, low molecular weight compound or the like, preferably a protein or DNA.

The protein is not particularly limited so long as it has an ability to interact with the modified protein of the present invention, and it may be a protein of full length or a partial peptide containing an active site for binding. Further, it may be a protein of which amino acid sequence or function is known or unknown. It may be a synthesized peptide chain, a protein purified from an organism, a protein obtained by translation from a cDNA library using a suitable translation system and purification, or the like, and they can be used as the target molecule. The synthesized peptide chain may be a glycoprotein consisting of a synthesized peptide chain attached with a sugar chain. Among these, a purified protein of which amino acid sequence is known or a protein obtained by translation from a cDNA library and purification using suitable methods can be preferably used.

The nucleic acid is not particularly limited so long as it has an ability to interact with the modified protein of the present invention, and either DNA or RNA may be used. Further, it may be a nucleic acid of which nucleotide sequence or function is known or unknown. Preferably, a nucleic acid of which function as a nucleic acid having an ability to bind to a protein or nucleotide sequence is known or a nucleic acid obtained by cleavage with a restriction enzyme or the like and isolation from a genomic library or the like can be used.

The sugar chain is not particularly limited so long as it has an ability to interact with the modified protein of the present invention, and it may be a sugar chain of which saccharide sequence or function is known or unknown. Preferably, an already isolated and analyzed sugar chain of which saccharide sequence or function is known is used.

The low molecular weight compound is not particularly limited so long as it has an ability to interact with the modified protein of the present invention. A compound of which function is unknown or a compound of which ability to bind to a protein is already known may also be used.

The "interaction" caused by these targets molecules with the modified protein of the present invention usually means an action caused by an intermolecular force generated by at least one of covalent bond, hydrophobic bond, hydrogen bond, van der Waals binding and binding caused by electrostatic force between a protein and a target molecule. However, this term should be construed in its broadest sense, and it should not be construed in any limitative way. The covalent bond includes a coordinate bond and dipole bond. The binding caused by electrostatic force includes, besides electrostatic bond, electric repulsion. Further, a bonding reaction, synthetic reaction and decomposition reaction caused as a result of the aforementioned action are also included in the interaction.

Specific examples of the interaction include association and dissociation of an antigen and an antibody, association and dissociation of a protein receptor and a ligand, association and dissociation of an adhesion molecule and a partner molecule, association and dissociation of an enzyme and a substrate, association and dissociation of a nucleic acid and a protein binding to it, association and dissociation of proteins in an information transmission system, association and dissociation of a glycoprotein and a protein and association and dissociation of a sugar chain and a protein.

The target molecule to be used may be modified with a modification substance and used depending on embodiments. The modification substance is usually selected from nonradioactive modification substances such as fluorescent substances. The fluorescent substances may be any of various fluorescent dyes of, for example, fluorescein type, rhodamine type, Cy3, Cy5, eosine type, NBD type and so forth, which have a free functional group (e.g., carboxyl group, hydroxyl group, amino group etc.) and can bind to the aforementioned target substance such as proteins and nucleic acids. In addition, other compounds such as dyes may be used, and type and size of the compounds are not critical so long as they enable the modification.

Among these modification substances, a substance suitable for the method of measurement or analysis of change of signal generated due to an interaction between the target molecule and the modified protein of the present invention is used.

The aforementioned modification substance can be bound to the target molecule by a suitable method known per se. Specifically, when the target molecule is a protein, the method of modifying the C-terminal described in WO02/48347 or the like may be used. Further, when the target molecule is a nucleic acid, it can by easily modified by a method of performing PCR using an oligo DNA primer bound with a modification substance beforehand via a covalent bond or the like.

Further, the modified protein of the present invention or the target molecule used for present invention may be bound to a solid phase (i.e., immobilized) depending on the embodiment. As the method for binding to a solid phase, there are a method of binding it via the modification substance and a method of binding it via another portion.

The modification substance used in binding via the modification substance is usually a molecule specifically binding to a particular polypeptide (henceforth also referred to as a "ligand"), and a particular polypeptide binding to the ligand (henceforth also referred to as an "adaptor protein") is bound to the solid phase. The adaptor protein also includes binding proteins, receptor proteins constituting receptors, antibodies and so forth.

Examples of combinations of the adaptor protein and the ligand include any of various receptor proteins and a ligand thereof, for example, a biotin or iminobiotin binding protein such as avidin and streptavidin and biotin or iminobiotin, maltose binding protein and maltose, G protein and guanine nucleotide, polyhistidine peptide and metal ion such as nickel or cobalt ion, glutathione-S-transferase and glutathione, DNA binding protein and DNA, antibody and antigen molecule (epitope), calmodulin and calmodulin binding peptide, ATP binding protein and ATP, estradiol receptor protein and estradiol and so forth.

Among these, preferred combinations of the adaptor protein and the ligand are biotin or iminobiotin binding protein such as avidin and streptavidin and biotin or iminobiotin, maltose binding protein and maltose, polyhistidine peptide and metal ion such as nickel or cobalt ion, glutathione-S-transferase and glutathione, antibody and antigen molecule (epitope) and so forth, and a combination of streptavidin and biotin or iminobiotin is the most preferred. These binding proteins per se are known, and DNAs coding these proteins have already been cloned.

The adaptor protein can be bound to a solid phase surface by using a method known per se. Specifically, for example, there can be used a method of utilizing tannic acid, formalin, glutaraldehyde, pyruvic aldehyde, bis-diazotized benzizone, toluene-2,4-diisocyanate, amino group, carboxyl group that can be converted into an active ester group, hydroxyl group or amino group that can be converted into phosphoramidite group, or the like.

When the binding is attained via a portion other than the modification substance, there can be used a known method usually used for binding a protein, nucleic acid, sugar chain or low molecular weight compound to a solid phase. Specifically, there can be used, for example, a method of utilizing tannic acid, formalin, glutaraldehyde, pyruvic aldehyde, bis-diazotized benzizone, toluene-2,4-diisocyanate, amino group, carboxyl group that can be converted into an active ester group, hydroxyl group or amino group that can be converted into phosphoramidite group, or the like.

The solid phase may be one usually used for immobilizing a protein, nucleic acid or the like, and material and shape thereof are not particularly limited. For example, glass plates, nitrocellulose membranes, nylon membranes, polyvinylidene fluoride membranes, microplates made of plastics and so forth can be used.

The "measurement" is a means for collecting changes of signals used for analysis, and it should not be construed in any limitative way. As the measurement method used, any of methods that can detect an intermolecular interaction can be used, including fluorescence correlation spectroscopy, fluorescence resonance energy transfer method, evanescent field molecular imaging method, fluorescence depolarization method, fluorescence imaging analysis method, surface plasmon resonance method, enzyme linked immunosorbent assay and so forth.

The measurement method includes a method comprising adding the modified protein of the present invention onto an array on which a target molecule is immobilized and detecting the modified protein of the present invention specifically binding to the target molecule. The array on which the target molecule is immobilized means a solid phase on which the target molecule is immobilized in an arrangement enabling identification thereof. The method for detecting the modified protein of the present invention specifically binding to the target molecule is not particularly limited, so long as the method enables detection of the modified protein of the present invention specifically binding to the target molecule. However, there is usually used, for example, a method of removing the modified protein of the present invention not binding to the target molecule by washing from the array to which the modified protein of the present invention is added and detecting the remaining modified protein of the present invention.

Hereafter, examples of the measurement method will be explained.

1) Fluorescence Correlation Spectroscopy

The fluorescence correlation spectroscopy (FCS, Eigen, M., et al., Proc. Natl. Acad. Sci., USA, 91, 5740-5747 (1994)) is a method of measuring flow rate, diffusion coefficient, volume shrinkage or the like of particles under a confocal laser microscope or the like. In the present invention, interacting molecules can be measured by measuring change of translational Brownian movement of one original modified molecule of the present invention (C-terminal modified protein) caused by an interaction between the modified protein and a target molecule.

Specifically, fluorescence emitted from sample particles in a partial volume of a sample solution due to excitation of the sample particles by an excitation light is measured to obtain a photon ratio. This value changes with the number of the particles existing in a space volume observed during a specific period of time. The aforementioned various parameters can be calculated from the change of signals using an autocorrelation function. Apparatuses for carrying out FCS are also marketed from Carl Zeiss and so forth, and analysis can be performed by using these apparatuses also in the present invention.

When a protein-target molecule interaction is measured or analyzed by using this method, it is required to provide both of the C-terminal modified protein and the target molecule as solutions (liquid phase method). The target molecule does not need to be labeled. Further, a molecule having a molecular weight extremely smaller than that of the C-terminal modified protein of which interaction should be investigated is not suitable for this method, since such a molecule does not affect the Brownian movement of the C-terminal modified protein.

However, fluorescence cross-correlation spectroscopy (FCCS) using two kinds of fluorescent dyes can detect even an interaction between proteins having molecular weights of similar order, of which detection is difficult by FCS using one kind of fluorescent dye. Although the fluorescence resonance energy transfer (FRET) method is known as another method of using two kinds of fluorescent dyes, two kinds of fluorescent dyes need to approach each other at a distance within 40 to 50 Å in order to cause FRET, and there is a risk in this method that FRET may not be observed depending on sizes of proteins, locations at which the fluorescent dyes are attached or the like, even an interaction occurs. On the other hand, since the detection of cross-correlation does not depend on the distance between the fluorescent dyes in the FCCS method, it does not suffer from such a problem. Further, comparing with the fluorescence depolarization method as another detection system, the FCCS method has advantages of a smaller amount of required sample, shorter detection time, easier automatization for HTS and so forth. Further, since the FCCS method provides extremely fundamental information such as size and number of fluorescence-labeled molecules, it may be used for general purpose like the surface plasmon resonance method. The difference between the both is that, in the surface plasmon resonance method, an interaction is detected in the state that proteins are immobilized, whereas the FCCS method enables observation of interaction in a solution, which is closer to a natural state. In the FCCS method, although proteins do not need to be immobilized, the proteins must be labeled with fluorescent dyes instead. However, it has been made possible by the present invention to overcome this problem.

Further, the FCCS method enables investigation of a protein-protein interaction or protein-nucleic acid interaction in a state of solution, which is close to the intracellular environment, and enables convenient calculation of dissociation constant (binding constant) by one measurement.

The method for bringing a target molecule into contact with the C-terminal modified protein in this method may be any method that allows the contact in a sufficient degree such that they can interact with each other. However, it is preferably attained by a method of introducing a solution dissolving the C-terminal modified protein in a buffer usually used for biochemical purpose or the like at an appropriate concentration into a well for measurement in a commercially available FCS apparatus and further introducing a solution dissolving the target molecule in the same buffer at an appropriate concentration into the well.

In this method, as a method of performing multiple analyses, for example, there is used a method of introducing multiple kinds of different C-terminal modified proteins into wells for measurement in the aforementioned FCS apparatus, respectively, and further introducing a solution of a particular target molecule into the wells, or introducing a particular C-terminal modified protein into wells, and further introducing solutions of multiple kinds of different target molecules into the wells, respectively.

(2) Fluorescence Imaging Analysis Method

The fluorescence imaging analysis method is a method of bringing a modifying molecule into contact with an immobilized molecule and measuring or analyzing fluorescence emitted by the immobilized modifying molecule remained on the immobilized molecule due to an interaction between the both molecules using a commercially available fluorescence imaging analyzer.

When a protein-target molecule interaction is measured or analyzed by using this method, one of the C-terminal modified protein or the target molecule must be immobilized by the aforementioned method. When an immobilized target molecule is used, either a modified or unmodified target molecule can be used. Further, when it is used without immobilization, it must be modified with the aforementioned modification substance. Either a C-terminal modified protein immobilized at the modified portion or a C-terminal modified protein immobilized at a portion other than the modified portion may be used.

As a substrate for immobilizing a C-terminal modified protein or target molecule (solid phase), there can be used glass plates, nitrocellulose membranes, nylon membranes, microplates made of plastics and so forth, which are usually used for immobilizing a protein, nucleic acid or the like. Further, such substrates as mentioned above of which surfaces are bound with various functional groups (amino group, carboxyl group, thiol group, hydroxyl group etc.) or various ligands (biotin, iminobiotin, metal ions such as nickel or cobalt ion, glutathione, saccharides, nucleotides, DNA, RNA, antibody, calmodulin, receptor protein etc.) can also be used.

The method for bringing a modified target molecule or a C-terminal modified protein into contact with an immobilized molecule in this method may be any method that allows the contact in a sufficient degree such that the both molecules can interact with each other. However, it is preferably attained by a method of preparing a solution dissolving the modified target molecule or the C-terminal modified protein in a buffer usually used for biochemical purpose at an appropriate concentration and bringing the solution into contact with the solid phase surface.

After bringing the both molecules into contact with each other, a step of washing off excessively existing modified target molecule or C-terminal modified protein with the same buffer or the like is preferably performed, and fluorescence signal emitted from the modification substance of the target molecule or C-terminal modified protein which remained on the solid phase, or a mixed signal of fluorescence emitted from the immobilized modified molecule and fluorescence emitted from the modified molecule remained on the solid phase can be measured or analyzed by using a commercially available imaging analyzer to identify the molecule that interacts with the immobilized molecule.

In this method, as a method of simultaneously performing multiple analyses, for example, there is used a method of immobilizing multiple kinds of C-terminal modified proteins or modified or unmodified target molecules on the aforementioned solid phase surface with positioning addresses, a method of bringing multiple kinds of non-immobilized C-terminal modified proteins or modified target molecules into contact with one kind of C-terminal modified protein or modified or unmodified target molecule, or the like. When multiple kinds of C-terminal modified proteins or modified target molecules are brought into contact, the molecules remained on the solid phase can be obtained by dissociating them using difference of buffer concentration or the like and analyzed by a known method to identify them.

(3) Fluorescence Resonance Energy Transfer Method

As another intermolecular interaction detection method using two kinds of fluorescent dyes, the fluorescence resonance energy transfer (FRET) method is well known. FRET means a phenomenon that, if a fluorescence spectrum of one of two kinds of fluorescent dyes (energy donor) and an absorption spectrum of the other (energy receptor) overlap, and the distance between two of the fluorescent dyes is sufficiently small, it becomes more likely that excitation energy of the donor excites the receptor before the donor emits fluorescence. Therefore, two kinds of proteins of which interaction is desired to be detected are labeled with fluorescent dyes serving as the donor and the receptor, respectively, and the donor is excited. When the two kinds of proteins do not interact with each other, FRET is not caused because the distance between the fluorescence dyes is large, and thus fluorescence spectrum of the donor is observed. However, if the two kinds of proteins interact with each other, and hence the distance between the fluorescent dyes becomes smaller, fluorescence spectrum of the receptor is observed due to FRET. Therefore, presence or absence of an interaction between the proteins can be determined on the basis of difference in wavelengths of fluorescence spectra. As for the fluorescent dyes, a combination of fluorescein as the donor and rhodamine as the receptor is frequently used. Further, it is recently attempted to observe FRET in a cell to detect an interaction by using combination of mutant green fluorescence proteins (GFP) emitting fluorescence of different wavelengths. As a drawback of this method, it is mentioned that since two kinds of fluorescent dyes need to approach to each other at a distance within 40 to 50 Å in order to cause FRET, there is a risk that FRET may not be observed depending on sizes of proteins, locations at which the fluorescent dyes are attached or the like, even if an interaction occurs.

(4) Evanescent Field Molecular Imaging Method

The evanescent field molecular imaging method is a method described in Funatsu, T., et al., Nature, 374, 555-559 (1995) or the like, and it is a method of bringing a second molecule as a solution into contact with a molecule immobilized on a transparent material such as glass, irradiating them with a laser light or the like from a light source at such an angle that an evanescent field should be generated, and measuring or analyzing the generated evanescent light using a detector. These operations can be performed by using an evanescent field fluorescence microscope known per se.

When a protein-target molecule interaction is measured or analyzed by using this method, one of the C-terminal modified protein or the target molecule must be immobilized by the aforementioned method. When an immobilized target molecule is used, it does not need to be modified. However, when it is used without immobilization, it must be modified with the aforementioned modification substance.

As the substrate for immobilizing the C-terminal modified protein or target molecule, a substrate made of a material of glass or the like is used, and quartz glass is preferably used. Further, a substrate of which surface is cleaned by ultrasonication is preferred in order to prevent scatter of laser light or the like.

The method for bringing a non-immobilized C-terminal modified protein or target molecule into contact with an immobilized molecule in this method may be any method that allows the contact in a sufficient degree such that the both molecules can interact with each other. However, a method of preparing a solution dissolving the non-immobilized C-terminal modified protein or modified target molecule in a buffer usually used for biochemical purpose at an appropriate concentration and adding the solution dropwise to the solid phase surface is preferred.

After bringing the both molecules into contact with each other, fluorescence generated through excitation by the evanescent field illumination can be measured by using a detector such as a CCD camera to identify the molecule that interacts with the immobilized molecule.

In this method, as a method of simultaneously performing multiple analyses, for example, there is used a method of immobilizing multiple kinds of C-terminal modified proteins or modified target molecules on the aforementioned substrate with positioning addresses, or the like.

(5) Fluorescence Depolarization Method

The fluorescence polarization method (Perran, J., et al., J. Phys. Rad., 1, 390-401 (1926)) is a method utilizing the fact that a fluorescent molecule excited with a polarized fluorescent light emits fluorescence in the same plane of polarization during the excited state while it maintains a stationary state, whereas the emitted fluorescence has a plane different from that of the excitation light when the excited molecule undergoes rotational Brownian movement or the like during the excited state. The movement of molecule is affected by the size thereof, and when the fluorescent molecule is a macromolecule, the molecule scarcely shows movement during the excited state, and emitted light is maintained to be a polarized light. However, in the case of a low molecular weight fluorescent molecule, since it shows high moving velocity, the emitted light is depolarized. Therefore, if intensity of the fluorescence emitted from a fluorescent molecule excited by a plane polarized light is measured along the original plane and a plane perpendicular thereto, information of motility and existing state of the molecule can be obtained from a ratio of the fluorescence intensities for the both planes. According to this method, behavior of a target molecule that interacts with a fluorescence-modified molecule can be traced without being affected by contaminants, if any. This is because shift of polarization degree is measured only when the fluorescence-modified molecule and the target molecule interact with each other.

As apparatuses for carrying out this method, BECON (produced by Panyera) and so forth are marketed, and this method can be carried out by using these apparatuses.

When a protein-target molecule interaction is measured or analyzed by using this method, it is required to provide both of the C-terminal modified protein and the target molecule as solutions. The target molecule does not need to be modified. Further, a molecule having a molecular weight extremely smaller than that of the C-terminal modified protein of which interaction should be investigated is not suitable for this method, since such a molecule does not affect the Brownian movement of the C-terminal modified protein.

The method for bringing a target molecule into contact with the C-terminal modified protein in this method may be any method that allows the contact in sufficient degree such that they should interact with each other. However, it is preferably attained by a method of introducing a solution dissolving the C-terminal modified protein in a buffer usually used for biochemical purpose at an appropriate concentration into a well for measurement in a commercially available fluorescence depolarization apparatus and further introducing a solution dissolving the target molecule in the same buffer at an appropriate concentration into the well.

It is expected that specificity of interaction between the C-terminal modified protein and the target molecules to be measured in this method is not necessarily so high as that of an antigen-antibody reaction. Therefore, in order to identify an optimum combination, it is effective that degree of interaction should be numerically defined. As an index representing degree of interaction, for example, a value of the minimum target substance concentration providing the maximum fluorescence polarization degree for a C-terminal modified protein of a fixed concentration or the like can be used.

In this method, as a method of simultaneously performing multiple analyses, for example, there is used a method of introducing multiple kinds of different C-terminal modified proteins into wells for measurement in the aforementioned fluorescence depolarization apparatus, respectively, and further introducing a solution of a particular target molecule into the wells, or introducing a particular C-terminal modified protein into wells and further introducing solutions of multiple kinds of different target molecules into the wells, respectively.

(6) Surface Plasmon Resonance Method

The surface plasmon resonance method is a method of measuring surface plasmon excited by a molecule interacting at a metal/liquid interface as change of intensity of reflected light (Cullen, D. C., et al., Biosensors, 3 (4), 211-225 (1987-88)). When a protein-target molecule interaction is measured or analyzed by using this method, the C-terminal modified protein must be immobilized by the aforementioned method, but the target molecule does not need to be modified.

As a substrate for immobilizing the C-terminal modified protein, a transparent substrate made of glass or the like on which a thin film of metal such as gold, silver or platinum is formed is used. The transparent substrate may be any of those usually used for surface plasmon resonance apparatuses. It generally consists of glass as a substrate consisting of a material transparent to a laser light, and such a substrate having a thickness of about 0.1 to 5 mm is generally used. Further, thickness of the metal thin film is suitably about 100 to 2000 Å. Those marketed as such immobilization substrates for surface plasmon resonance apparatuses can also be used. The C-terminal modified protein can be immobilized on the substrate by the method described above.

The method for bringing a target molecule into contact with the C-terminal modified protein in this method may be any method that allows the contact in a sufficient degree such that the both molecules can interact with each other. However, a method of bringing the immobilized C-terminal modified protein into contact with a solution dissolving the target molecule in a buffer usually used for biochemical purpose at an appropriate concentration can be preferably used.

These steps may also be performed by using a commercially available surface plasmon resonance apparatus, for example, BIAcore 2000 (produced by Pharmacia Biosensor). After bringing the both molecules into contact with each other, change with time of relative intensity of each reflected light can be measured by using a surface plasmon resonance apparatus known per se to analyze or measure an interaction of the immobilized C-terminal modified protein and the target molecule.

In this method, as a method of simultaneously performing multiple analyses, for example, there is used a method of immobilizing multiple kinds of C-terminal modified proteins on a substrate used for the surface plasmon resonance apparatus with positioning addresses, a method of bringing multiple kinds of target molecules into contact with one kind of immobilized C-terminal modified protein, or the like.

(7) Enzyme Linked Immunosorbent Assay

The enzyme linked immunosorbent assay (ELISA, Crowther, J. R., Methods in Molecular Biology, 42 (1995)) is a method of bringing a solution containing an antibody into contact with an antigen immobilized on a solid phase and measuring or analyzing the antibody remaining on the immobilized antigen due to the interaction between the both molecules (antigen-antibody reaction) on the basis of fluorescence emitted from a modification molecule (IgG etc.) specifically binding to the antibody or a signal emitted by a dye formed from the modification molecule as a substrate using a commercially available detector (ELISA reader).

When a protein-target molecule interaction is measured or analyzed by using this method, the C-terminal modified protein serving as the antigen must be immobilized by the aforementioned method. Further, the target molecule serving as the antibody must be modified with the aforementioned modification substance.

As a substrate for immobilizing the C-terminal modified protein serving as the antigen, microplates made of plastics usually used for ELISA and so forth can also be used.

The method for bringing the modified target molecule serving as the antibody into contact with an immobilized molecule in this method may be any method that allows the contact in a sufficient degree such that the both molecules can interact with each other. However, a method of preparing a solution dissolving the modified target molecule in a buffer usually used for biochemical purpose at an appropriate concentration and introducing the solution into a microplate is preferred.

After bringing the both molecules into contact with each other, a step of washing off excessively existing modified molecule not binding to the immobilized molecule is preferably performed, and fluorescence emitted from the modified molecule remained on the solid phase can be measured or analyzed by using a commercially available ELISA reader or the like to identify the molecule that interacts with the immobilized antigen molecule.

In this method, as a method of simultaneously performing multiple analyses, for example, there is used a method of immobilizing multiple kinds of different modified target molecules in each well of the aforementioned microplate.

Further, the protein of the present invention can also be used for identification of a molecule that causes an interaction.

When primary structure of a target molecule for which an interaction with a C-terminal modified protein is recognized on the basis of measurement according to any one of the methods described above is unknown, the primary structure can be analyzed by a suitable method known per se. Specifically, when the target molecule for which an interaction is recognized is a protein, its amino acid sequence can be analyzed by using an amino acid analyzer etc. to identify the primary structure. Further, when the target molecule is a nucleic acid, nucleotide sequence can be determined by a nucleotide sequence determination method using an automatic DNA sequencer or the like.

Furthermore, the protein of the present invention can also be used for analysis of an interaction with a protein library.

The present invention provides a gene or nucleic acid sequence encoding a novel protein that can form a complex with the c-Fos protein, which was obtained by performing cotranslation selection/screening of IVV using the c-Fos protein as the bait and a mouse brain cDNA library as the prey, and methods for utilizing them. The present invention also provides a method for utilizing a gene or nucleic acid sequence encoding a known protein, which is not known to form a complex with the c-Fos protein.

The present invention not only enables screening of known gene sequences and known nucleic acid sequences, but also can provide a novel protein having a novel amino acid sequence formed by unexpected frame shift, a novel protein having a nucleic acid sequence for which only the nucleic acid sequence is published on the basis of genome information, or a novel protein having a completely novel nucleic acid sequence, further, a protein that forms a complex by an unexpected indirect interaction in addition to a direct interaction, a gene or nucleic acid sequence encoding the protein, and methods for utilizing them.

EXAMPLES

Hereafter, the amino acid sequences of the proteins of the present invention and the sequences of the nucleic acids encoding them will be specifically described. However, the following examples should be construed as a mere aid for specifically understanding the present invention, and the scope of the present invention is no way limited by the following examples.

Example 1

Cotranslation selection/screening of IVV was carried out by using the c-Fos protein as a bait and a mouse brain cDNA library as a prey (FIG. 2), and as a result, genes or nucleic acid sequences encoding novel proteins that can form a complex with the c-Fos protein were obtained.

The preparation method of the bait, c-Fos protein, was as follows. A DNA template was prepared from a pCMV-Fos-CBPzz vector (SEQ ID NO: 168) by PCR (primers 5' SP6 (O29)T7-FosCBPzz (SEQ ID NO: 169) and 3' FosCBPzz (SEQ ID NO: 170), and PCR program CYCB1 (refer to Table 1)) using TaKaRa Ex Taq (Takara Shuzo). The DNA template was transcribed (37° C., 2 hours) by using RiboMAX™ Large Scale RNA Production Systems (Promega) to prepare a mRNA template of the bait c-Fos protein. A bait DNA made to coexist was prepared by PCR (primers 5' DNA (SEQ ID NO: 172) and 3' DNA (SEQ ID NO: 173)) using DNA-Fos/Jun (SEQ ID NO: 171) containing the Fos/Jun binding sequence as a template according to the PCR program V-2 (refer to Table 1).

Figure 3:
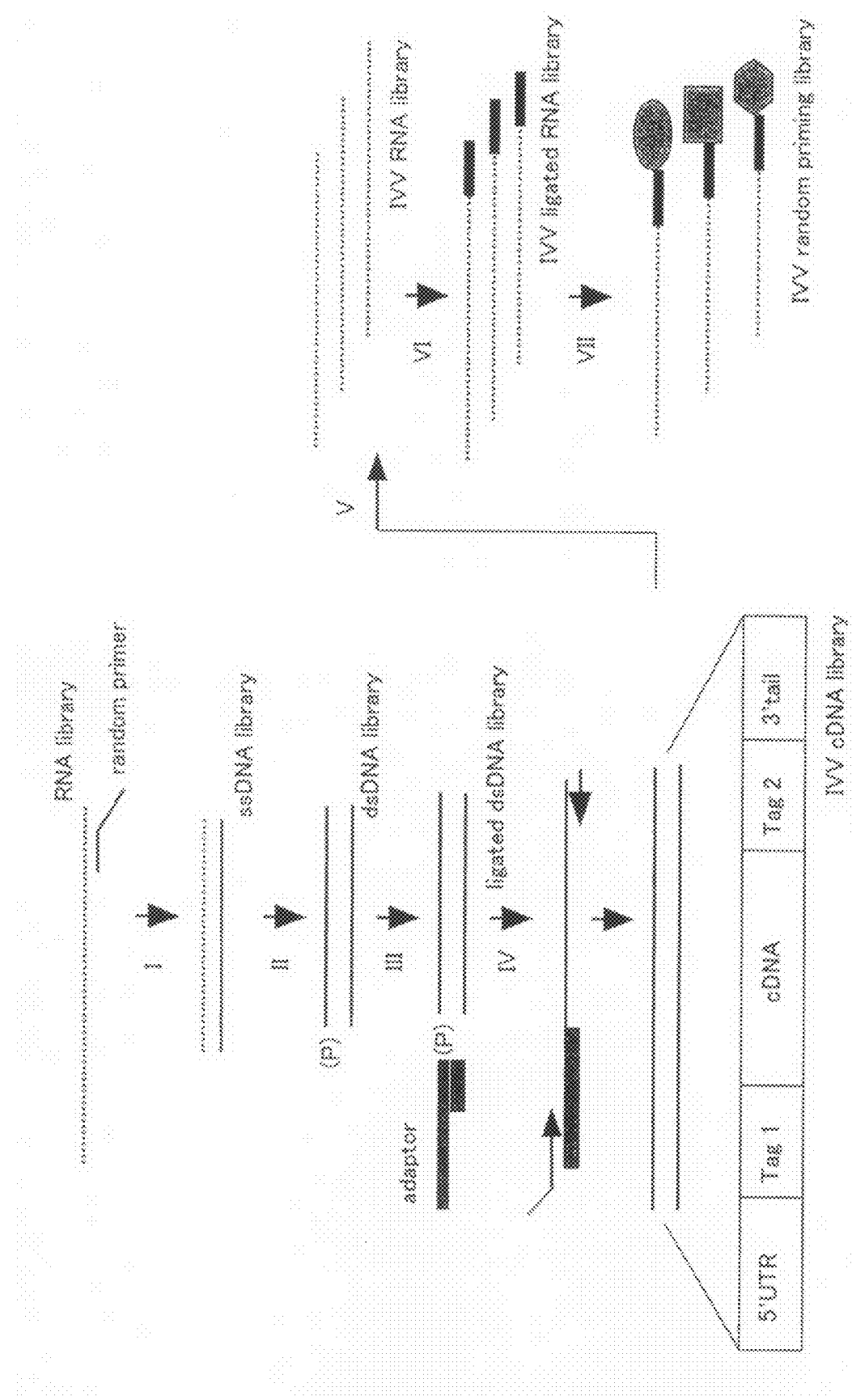
FIG. 3 shows the random priming library of IVV used for detection of the proteins and genes of the present invention and the nucleotide sequences thereof, and the outline of the method for producing it. Using an RNA library as a template and a random primer including a random sequence consisting of nine nucleotides and a specific sequence (tag2 sequence) in the random priming method, a library of single strand cDNAs (ssDNA) complementary to mRNAs is synthesized by reverse transcription (I). Only RNAs are decomposed in the double strands of cDNA and RNA with RNaseH, at the same time, DNAs complementary to cDNAs are synthesized with DNA polymerase I, and further a nick existing between the DNAs synthesized with DNA polymerase I is modified by using a DNA ligase to synthesized a double strand (dsDNA) library (II). The synthesized double-stranded cDNAs have a phosphate group at the 5' end only on the side synthesized with the DNA polymerase I, and therefore this is utilized to ligate an adaptor having a specific sequence (5' UTR=promoter+enhancer) using a DNA ligase to synthesize a ligated dsDNA library (III). PCR is carried out by utilizing the adaptor and the specific sequence of the random primer to prepare a cDNA library of assigning molecules having the sequences of a promoter and an enhancer on the 5' end side and an A tail on the 3' end side (IVV cDNA library) (IV). Then, the IVV cDNA library is transcribed to form an IVV RNA library (V), a spacer for preparing IVV is ligated (VI), and further it is translated in a cell-free translation system or the like to form a library of assigning molecules (VII).

The preparation method of the mouse brain cDNA library as the prey was as follows. An IVV random library was prepared as shown in FIG. 3. As an RNA library, a commercially available mouse brain (polyA+) RNA library (obtained by purifying a tissue extracted RNA library in an oligo dT column, Clontech) was purchased. As for design of an adaptor, it was designed so as to add a 5' UTR sequence suitable for the production of assigning molecules (promoter SP6+enhancer O29 or O') to the library as a sequence required for IVV formation. For the mouse brain (polyA+) RNA library, an adaptor having the enhancer O29 was used. The main chain (SEQ ID NO: 174 or 175) and the subchain (gaattcgc or ggaattcg) of the adaptor for the enhancer O29 were each dissolved in the TE buffer (10 mM Tris-Cl, pH8.0, 1 mM EDTA) at a concentration of 100 μM, and 10 μl each of the solutions of the main chain and subchain were mixed so that the main chain and the subchain were mixed in equimolar amounts. The mixture was heated at 90° C. for 2 minutes and at 70° C. for 5 minutes, set on a water bath of 60° C., and then slowly cooled from 60° C. to room temperature by turning off the heater of the bath. The mixture was divided into 5 μl aliquots, and stored at −20° C. Then, the mouse brain (polyA+) RNA library was reverse-transcribed into single stranded DNAs (FIG. 3, I). 0.5 μg of the mouse brain (polyA+) RNA library (1.4 pmole/0.5 μg), 2 pmol of 3' random primer (SEQ ID NO: 176) and DEPC water were added to obtain a volume of 12.0 μl, and the mixture was heated at 70° C. for 10 minutes, and cooled for 1 minute on ice. A reverse transcription reaction was performed at 45° C. for 1 hour by using this mixture and SuperScriptII RT (SuperScript Double-stranded cDNA Synthesis Kit, Invitrogen). Then, the total amount of the single stranded DNAs synthesized by the reverse transcription reaction was used for a reaction with an *E. coli* DNA ligase, *E. coli* Polymerase I and *E. coli* RNase H (Superscript Double-stranded cDNA Synthesis Kit, Invitrogen) at 16° C. for 2 hours, and the product was blunt-ended with T4 DNA polymerase at 16° C. for 5 minutes to synthesize double-stranded DNAs (FIG. 3, II). Then, the adaptor previously prepared was ligated by taking advantage of the fact that the 5' ends of the double-stranded DNAs were phosphorylated (FIG. 3, III). The synthesized double-stranded DNA library was subjected to ethanol precipitation, and dissolved in 4 μl of DEPC water. 100 μM of the prepared adaptor in a volume of 1.0 μl and 50 μl of Ligation High (TOYOBO) were added thereto, reacted overnight at 16° C., purified (DNA purification kit, QIAGEN), and then adjusted to a volume of 50 μl. Thereafter, PCR (EX Taq Hot Start Version, TaKaRa) was performed (FIG. 3, IV). Out of 50 μl of the ligated double-stranded DNA library, 2 μl was used as a template together with 5' PCR primer (SEQ ID NO: 172) having a specific sequence required for IVV (O29) and 3' PCR primer (SEQ ID NO: 173) to prepare an IVV cDNA library. As for the PCR conditions, the total volume was 100 μl, and 22 cycles of the reactions (each cycle consists of reactions at 94° C. for 30 seconds, at 60° C. for 30 seconds, and at 72° C. for 90 seconds, and the final extension reaction was performed at 72° C. for 180 seconds).

Cotranslation (26° C., 60 minutes) of the mRNA template of the bait c-Fos protein, the mouse brain cDNA library as the prey, and the bait DNA made to coexist was carried out in a cell-free translation system of wheat (Wheat Germ Extract, Promega) in a volume of 50 μl. To 50 μl of the sample, 50 μl of IgG binding buffer (10 mM Tris-Cl, pH 8.0, 150 mM NaCl, 0.1% NP40) was added to obtain the total volume of 100 μl (cotranslation sample). Then, IgG agarose (Sigma) was washed twice with the IgG binding buffer, and the cotranslation sample (100 μl) was added thereto, and the mixture was stirred by rotation at 4° C. for 2 hours. The IgG agarose was washed 3 times with the binding buffer and once with a TEV cleaving buffer (10 mM Tris-Cl, pH 8.0, 150 mM NaCl, 0.1% NP40, 0.5 mM EDTA, 1 mM DTT), and the bait/prey complex binding to the IgG agarose was cleaved with TEV protease (GIBCO-BRL, 16° C., 2 hours). Further, to 90 μl of the supernatant, 300 μl of a calmodulin binding buffer, 0.3 μl of 1 M $CaCl_2$ and 50 μl of calmodulin beads washed twice with 500 μl of the calmodulin binding buffer were added, and the mixture was stirred by rotation at 4° C. for 1 hour. After centrifugation, the beads were washed 3 times with 1000 μl the calmodulin binding buffer. 50 μl of a calmodulin elution buffer was added, and the mixture was left on ice for 1 to 2 minutes, and centrifuged to collect 50 μl of a solution. By using the collected solution as a template, RT-PCR (One step RT-PCR kit (QIAGEN), primers: SEQ ID NOS: 177 and 178, program: RT-QH30' (refer to Table 1)). After this screening/selection procedure (FIG. 2) was repeated for 3 rounds, the library was cloned and sequenced to obtain the sequences of SEQ ID NOS: 1 to 14 (amino acid sequences of Fip-cx), SEQ ID NOS: 15 to 19 (amino acid sequences of Eef1dTEF-1), SEQ ID NOS: 20 to 22 (amino acid sequences of Schip1) and nucleic acid sequences corresponding to them (SEQ ID NOS: 1 to 22 in FIG. 1A). The same results were obtained for both of the library prepared by using the sequence of SEQ ID NO: 174 as the main chain of the adaptor for enhancer O29 and the library prepared by using the sequence of SEQ ID NO: 175 as the same.

All the proteins had a Leu zipper, and they are proteins found by the present invention for the first time to directly interact with c-Fos.

Figure 4:
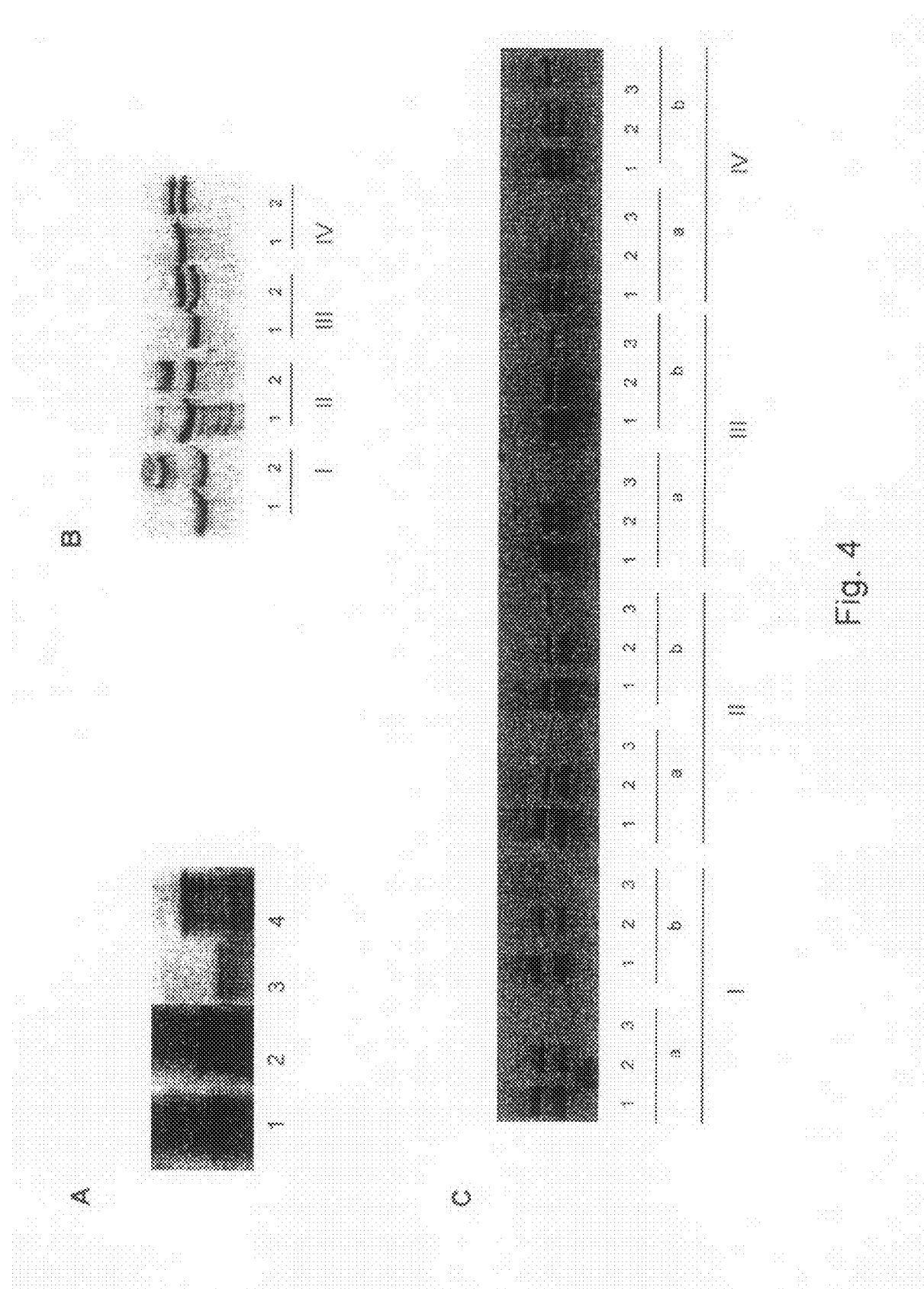
FIG. 4 (electrophoretic photographs) shows the result 1 of the verification of the interactions of the proteins and genes of the present invention and the nucleotide sequences thereof.
A: Proteins having the amino acid sequences of SEQ ID NOS: 2 (Fip-cx), 16 (Eef1dTEF-1), and 22 (Schip1) were confirmed by the C-terminal labeling method in a wheat cell-free translation system. Lane 1 to 4: c-Jun protein, proteins of SEQ ID NO: 2 (Fip-cx), SEQ ID NO: 16 (Eef1dTEF-1), and SEQ ID NO: 22 (Schip1).
B: IVVs having the amino acid sequences of SEQ ID NOS: 2 (Fip-cx), 16 (Eef1dTEF-1), and 22 (Schip1) were confirmed in a wheat cell-free translation system. Lanes 1 and 2: mRNA and IVV, I to IV: c-Jun, SEQ ID NO: 2 (Fip-cx), SEQ ID NO: 16 (Eef1dTEF-1), and SEQ ID NO: 22 (Schip1).
C: Interactions were confirmed by the pull-down method utilizing IVVs having the amino acid sequences of SEQ ID NOS: 2 (Fip-cx), 16 (Eef1dTEF-1), and 22 (Schip1). Lanes 1 to 3: IVV, supernatant, and beads. a and b: with and without the bait c-Fos. I to IV: c-Jun, SEQ ID NO: 2 (Fip-cx), SEQ ID NO: 16 (Eef1dTEF-1), and SEQ ID NO: 22 (Schip1).

As a verification experiment of the interactions of the obtained proteins and c-Fos, expression of the proteins of SEQ ID NOS: 2 (Fip-cx), 16 (Eef1dTEF-1) and 22 (Schip1) (FIG. 1A) in a cell-free translation system was experimentally confirmed by using the DNA sequences of SEQ ID NOS: 2-1, 16-1, and 22-1 according to the descriptions of WO02/46395, Example 1, (2) Preparation of coding molecule and (3) Translation of coding molecule, i.e., it was confirmed by the C-terminal labeling method that the proteins were expressed in a wheat cell-free translation system (FIG. 4, A).

Further, formation of IVV was also confirmed according to the descriptions of WO02/46395, Example 1, (4) Binding of spacer molecule and coding molecule and (5) Formation of assigning molecule (FIG. 4, B). Furthermore, the interaction with c-Fos was confirmed for those subjected to the first stage pull-down (FIG. 2, IgG+TEV) by 8 M urea/10% SDS-PAGE (FIG. 4, C). As a result, it could be confirmed that the proteins of SEQ ID NOS: 2 (Fip-cx), 16 (Eef1dTEF-1) and 22 (Schip1) interacted with c-Fos.

Further, the proteins and genes or nucleic acid sequences of the present invention can be used as an inhibitor for blocking transcription, gene duplication and so forth as functions of c-Fos by utilizing the novel function thereof (function of enabling binding with c-Fos in this case). The basis of the above is originates in the fact that the genes detected by the IVV method have been detected through a competitive process constituted by screening repeated multiple times. Therefore, the genes detected by the IVV method show a certain number distribution, and a gene having a stronger competitive power should be detected in a larger number. This suggests that a larger number of clones corresponds to stronger competitive power, and thus such a gene acts more effectively as a blocking agent or inhibitor. In the IVV selection performed in this example, three (/72) of c-Jun well known as a prey were detected for the bait c-Fos. Thus, the numbers of clones (FIG. 1A) detected in the selection indicate that Fip-cx, Eef1 and Schip1 have extremely stronger competitive power compared with known proteins, and they can sufficiently compete, and the proteins can be utilized as an inhibitor for blocking functions of transcription of a complex, gene duplication and so forth by the interaction of c-Jun and a known protein.

Example 2

A prey IVV library was prepared from the bait c-Fos and a mouse brain cDNA library in the same manner as that used in Example 1, and the screening/selection procedure (FIG. 2) was also performed in the same manner as that used in Example 1. However, in this example, the first stage selection using IgG beads in the two-stage screening was repeated 3 times, and the two-stage selection was performed only for the 4th time to obtain the proteins of SEQ ID NOS: 47 to 56 (amino acid sequences of Fip-cx.1), SEQ ID NOS: 57 to 76 (amino acid sequences of Fip-cx.2), SEQ ID NOS: 77 to 81 (amino acid sequences of Optin), SEQ ID NOS: 82 to 84 (amino acid sequences of Snap19), SEQ ID NOS: 85 and 86 (amino acid sequences of C130020M04Rik), SEQ ID NOS: 87 to 89 (amino acid sequences of FLJ32000), SEQ ID NOS: 90 and 91 (amino acid sequences of Rit2), SEQ ID NOS: 92 and 93 (amino acid sequences of cytocrome b), SEQ ID NOS: 94 and 95 (amino acid sequences of Apoe), SEQ ID NOS: 96 and 97 (amino acid sequences of App), SEQ ID NOS: 98 and 99 (amino acid sequences of Dnaja2), SEQ ID NOS: 100 and 101 (amino acid sequences of Fip-c10), SEQ ID NO: 102 (amino acid sequence of Fip-c4), SEQ ID NO: 103 (amino acid sequence of Fip-c18), and nucleic acid sequences corresponding to these proteins (SEQ ID NOS: 47 to 76 in FIG. 1A, and SEQ ID NOS: 77 to 103 in FIG. 1B). The same results were obtained for both of the library prepared by using the sequence of SEQ ID NO: 174 as the main chain of the adaptor for enhancer O29 and the library prepared by using the sequence of SEQ ID NO: 175 as the same.

Fip-cx.1, Fip-cx.2, Optin, C130020M04Rik, FLJ32000, and cytocrome b proteins have a Leu zipper, and Rit2, Apoe, App, Dnaja2, Fip-c10, Fip-c4, and Fip-c18 proteins do not have a Leu zipper. All the proteins are proteins found by the present invention for the first time to form a complex with c-Fos.

As a verification experiment of the interactions of the obtained proteins and c-Fos, expression of the proteins of SEQ ID NOS: 48 (Fip-cx.1), 75 (Fip-cx.2), 78 (Optn), 84 (Snapc5), 86 (C130020M04Rik), 88 (FLJ32000), 91 (Rit2), 93 (cytochrome b), 95 (Apoe), 97 (betaAPP), 99 (Hsp40), 101 (Fip-c10), 102 (Fip-c4) and 103 (Fip-c18) (FIG. 1) in a cell-free translation system was experimentally confirmed by using the DNA sequences of SEQ ID NOS: 105, 139, 142, 148, 150, 152, 155, 157, 159, 161, 163, 165, 166 and 167 according to the descriptions of WO02/46395, Example 1, (2) Preparation of coding molecule and (3) Translation of coding molecule, i.e., it was confirmed by the C-terminal labeling method that the proteins were expressed in a wheat cell-free translation system (FIG. 5, A). Further, among those C-terminal labeled proteins for which expression was confirmed, the proteins of SEQ ID NOS: 48 (Fip-cx.1) and 75 (Fip-cx.2), which are completely novel proteins not registered at any database, were used as a prey protein to confirm interactions thereof with the bait c-Fos by pull-down. As for the preparation method of the prey protein, specifically, PCR cloning kit (QIAGEN) was used to extract a sequence cloned in the pDrive vector (SEQ ID NO: 179, QIAGEN) from cells, and a DNA template was prepared by PCR (primers 5' F3 (SEQ ID NO: 180) and 3' R3 (SEQ ID NO: 181), PCR program: ISHI1562 (refer to Table 1), 100 μl scale) using TaKaRa Ex Taq (Takara Shuzo). The DNA template was transcribed (37° C., 2 hours, 50 μl scale) by using RiboMAX™ Large Scale RNA Production Systems (Promega) to prepare a mRNA template of the prey protein.

The preparation method of the bait c-Fos protein is the same as that used for the selection/screening.

Cell-free translation of the prey template (10 μl scale) was performed for 1 hour by using the C-terminal labeling method to prepare a prey protein in a C-terminal labeled state. At the same time, the translation reaction of the bait c-fos template was performed for 1 hour by the cell-free translation (50 μl scale) to produce the bait protein. After the translation, the both and the binding buffer were mixed (prey: 8 μl, bait: 10 μl, IgG binding buffer: 82 μl), and incubated with 50 μl of IgG agarose beads for 2 hours, and the beads were washed, then added with 20 μl of a buffer containing SDS, boiled at 100° C. for 5 minutes, and eluted. This sample was developed by 17.5% SDS-PAGE, and the FITC fluorochrome was observed by means of a fluorescence imager (FIG. 5, B). In addition, a reaction was also performed without adding the bait c-Fos protein as a control.

As a result, it could be confirmed that the proteins of SEQ ID NOS: 48 (Fip-cx.1) and 75 (Fip-cx.2) directly interacted with c-Fos.

Figure 6:
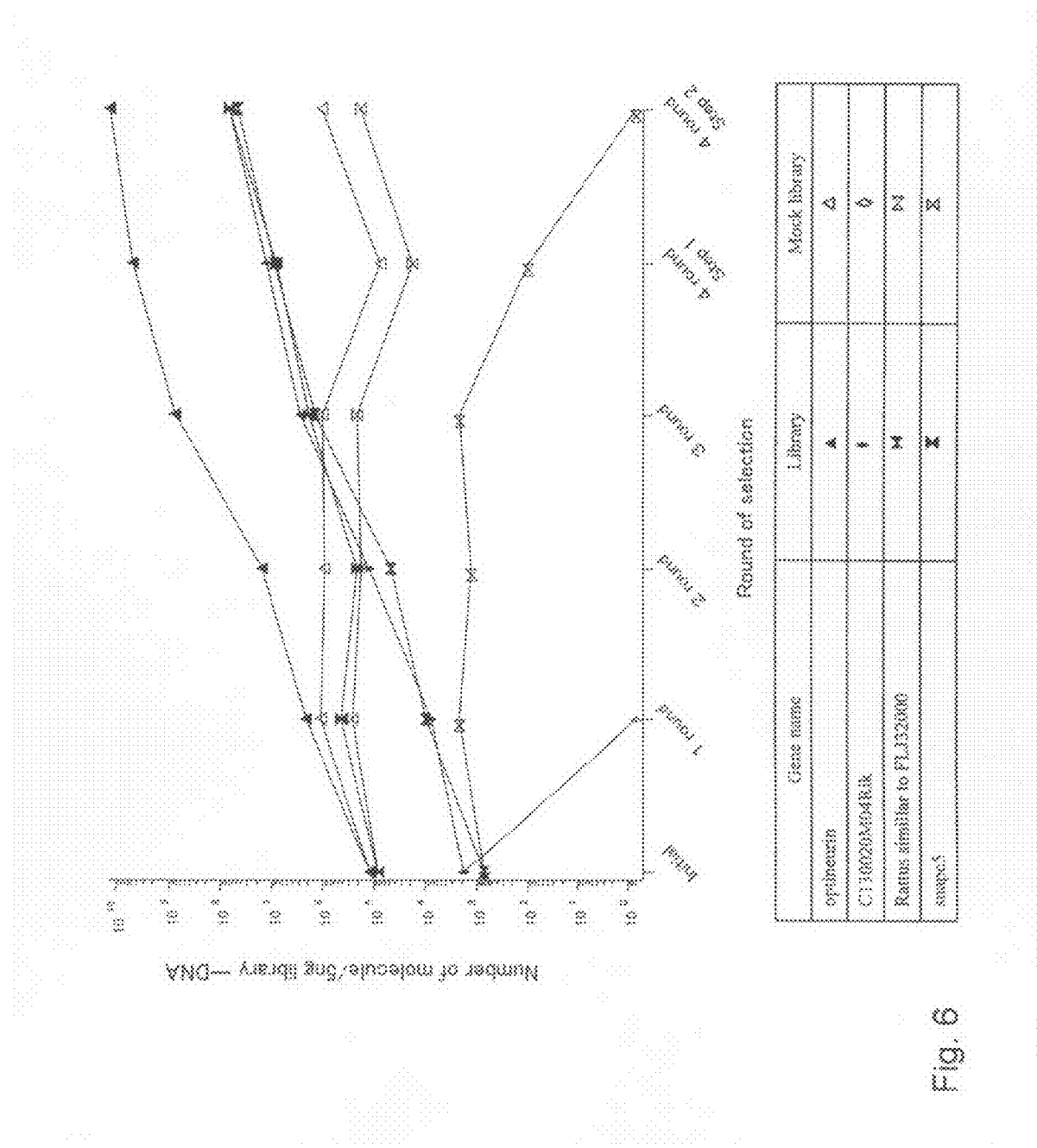
FIG. 6 shows the result of verification of the concentration rate and indirect interaction of the genes of the present invention. In order to confirm concentrations of 4 kinds of proteins of SEQ ID NOS: 78 (Optn), 84 (Snapc5), 86 (C130020M04Rik) and 88 (FLJ32000), real-time PCR was performed by using the nucleic acid sequences of SEQ ID NO: 142, 148, 150 and 152.
Figure 7:
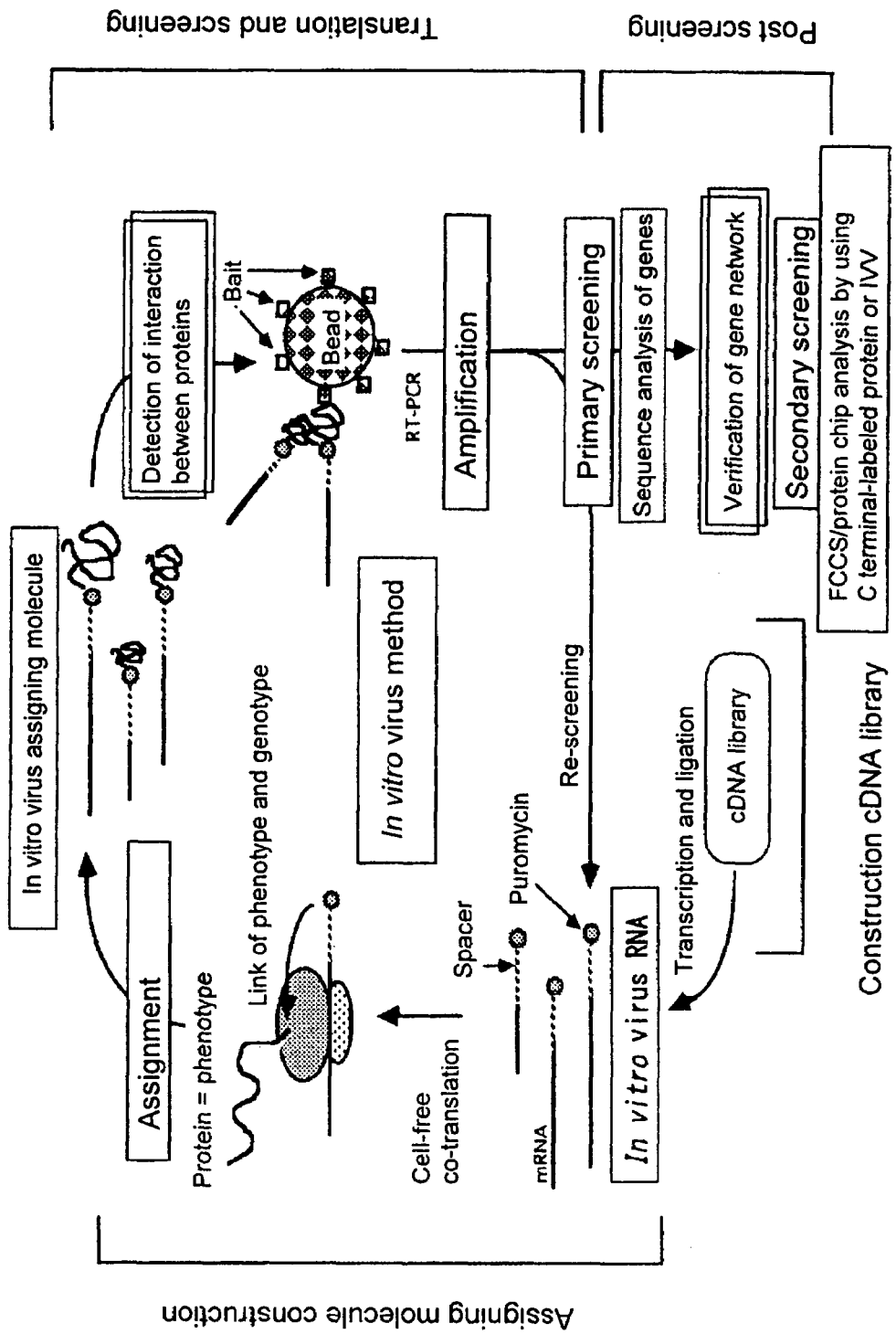
FIG. 7 shows outlines of the primary screening and secondary screening in the analysis of interaction of IVV with substances or proteins using the proteins and nucleic acid sequences of the present invention. It is possible to detect interactions with the substances and proteins in the primary screening using the proteins and nucleic acid sequences of the present invention, and further analyze the details of the interaction in the secondary screening using FCCS, microarray or the like. Further, the proteins and nucleic acid sequences of the present invention can also be independently used for analysis of interaction with the substances or proteins using FCCS, microarray, or the like as IVV or C-terminal labeled proteins. Furthermore, it is also possible to apply them to the evolutionary molecular engineering using IVV of the proteins or nucleic acid sequences of the present invention, and utilize them to create functional proteins in the primary screening. In such a case, it is also possible to analyze details of interactions of the created functional proteins with a combination of the primary screening and secondary screening.

Furthermore, as shown in FIG. 6, concentration of genes directly or indirectly interacting with c-Fos was confirmed by real time PCR using the nucleic acid sequences of SEQ ID NOS: 142 (Optn), 148 (Snapc5), 150 (C130020M04Rik) and 152 (FLJ32000). As for the specific method of the real time PCR, primers (SEQ ID NOS: 182 to 189) were designed for four kinds of genes (SEQ ID NOS: 142 (Optn), 148 (Snapc5), 150 (C130020M04Rik) and 152 (FLJ32000)) so that the amplification should be attained in the ranges of sequences obtained by the screening. For preparation of calibration curves, a gene comprising a DNA fragment of positive control incorporated into the pDrive vector was amplified by PCR (5' M13_F primer (SEQ ID NO: 190) and 3' M13_R primer (SEQ ID NO: 191) were used, and the PCR program lightcycler of Table 1 was used), which was controlled so that 1E03, 1E05, 1E07 or 1E09 clones/reaction should be obtained. The measurement was controlled so that each of the library DNA before screening, library DNA in each cycle of screening, and Mock library DNA not added with the bait c-Fos should be in an amount of 5 ng/reaction. The PCR measurement reaction was performed in a scale of 20 μl according to the programs shown in Table 1 by using LightCycler Instrument or LightCycler FastStart DNA Master SYBR Green I (both are produced by Roche Diagnostics).

Further, the proteins and genes or nucleic acid sequences of the present invention can be used as an inhibitor for blocking transcription, gene duplication and so forth as functions of c-Fos by utilizing the novel function thereof (function of enabling binding with c-Fos in this case). The basis of the above is originates in the fact that the genes detected by the IVV method have been detected through a competitive process constituted by screening repeated multiple times. Therefore, the genes detected by the IVV method show a certain number distribution, and a gene having a stronger competitive power should be detected in a larger number. This suggests that a larger number of clones corresponds to stronger competitive power, and thus such a gene acts more effectively as a blocking agent or inhibitor. In the IVV selection performed in this example, three (/142) of JunD well known as a prey were detected for the bait c-Fos. Thus, the numbers of clones (FIGS. 1A and 1B) detected in the selection indicate that Fip-cx.1, Fip-cx.2, Optn, and so forth have extremely stronger competitive power compared with known proteins, and Snap19, FLJ32000, and so forth can sufficiently compete with known proteins, and thus the proteins can be utilized as an inhibitor for blocking functions of transcription of a complex, gene duplication and so forth by the interaction of c-Jun and a known protein.

TABLE 1

PCR programs

Program name: CYCB1
Reaction conditions:

| | |
|---|---|
| 95° C. | 1 minute |
| 98° C. | 20 seconds |
| 55° C. | 1 minute |
| 72° C. | 4 minutes |
| 4° C. | Pause |

(98°C / 55°C / 72°C: 15 cycles)

Program name: V-2
Reaction conditions:

| | |
|---|---|
| 98° C. | 20 seconds |
| 55° C. | 1 minute |
| 72° C. | 3 minutes |
| 4° C. | Pause |

(35 cycles)

Program name: RT-QH30'
Reaction conditions:

| | |
|---|---|
| 60° C. | 30 minutes |
| 95° C. | 15 minutes |
| 94° C. | 30 seconds |
| 60° C. | 30 seconds |
| 72° C. | 3 minutes |
| 72° C. | 10 minutes |

(32 cycles for 1st and 2nd rounds, 30 cycles for 3rd round)

Program name: ISHI1562
Reaction conditions:

| | |
|---|---|
| 94° C. | 2 minutes |
| 94° C. | 30 seconds |
| 62° C. | 30 seconds |
| 73° C. | 2 minutes |
| 73° C. | 15 minutes |

(15 cycles)

TABLE 1-continued

PCR programs

Program name: lightcycler
Reaction condition:
95° C.  10 minutes
95° C.  15 seconds ┐
X° C.   10 seconds  ├ 40 cycles
72° C.  5 seconds  ┘

X: Annealing temperature was 62 to 51° C. depending on the Tm values of primers.

INDUSTRIAL APPLICABILITY

Because proteins that interact with c-Fos have been provided, it becomes possible to provide proteins forming a complex with c-Fos by not only a direct interaction, but also an unexpected indirect interaction, and nucleic acids encoding these proteins as well as methods for utilizing them.

---

What is claimed is:

1. A method for inhibiting formation of a complex between a target protein and a c-Fos protein, said method comprising:
    having a protein and a c-Fos protein in a system in which the complex is to be formed, wherein said protein is selected from the group consisting of:
    (a) the protein comprising the amino acid sequence of SEQ ID NO 96,
    (b) the protein comprising the amino acid sequence of SEQ ID NO: 97;
    (c) a protein which interacts with the c-Fos protein and comprises the amino acid sequence of SEQ ID NO: 96 with a deletion, substitution or addition of one amino acid residue; and
    (d) a protein which interacts with the c-Fos protein and comprises the amino acid sequence of SEQ ID NO: 97 with a deletion, substitution or addition of one amino acid residue,
    and wherein the formation between the target protein and the c-Fos protein of the complex is inhibited by said protein.

2. The method according to claim 1, wherein the protein (a)-(d) is translated in the system.

3. A method for inhibiting formation of a complex between a target protein and a c-Fos protein, said method comprising: having a protein and a c-Fos protein in a system in which the complex is to be formed, wherein said protein is selected from the group consisting of:
    (i) the protein encoded by the nucleotide sequence of SEQ ID NO: 160, and which interacts with the c-Fos protein;
    (ii) the protein encoded by the nucleotide sequence of SEQ ID NO: 161, and which interacts with the c-Fos protein;
    (iii) a protein which interacts with the c-Fos protein and is encoded by a nucleotide sequence that hybridizes under stringent conditions to the nucleotide sequence of SEQ ID NO: 160, wherein said stringent conditions comprise a wash in 0.1×SSC, 0.1% SDS for 15 minutes at 60° C.; and
    (iv) a protein which interacts with the c-Fos protein and is encoded by a nucleotide sequence that hybridizes under stringent conditions to the nucleotide sequence of SEQ ID NO: 161, wherein said stringent conditions comprise a wash in 0.1×SSC, 0.1% SDS for 15 minutes at 60° C.,
    and wherein the formation between the target protein and the c-Fos protein of the complex is inhibited by said protein.

4. The method according to claim 1, wherein the c-Fos protein is translated in the system.

5. The method according to claim 1, wherein both the protein (a)-(d) and c-Fos are translated in the system.

* * * * *

SEQUENCE LISTING

<160> NUMBER OF SEQ ID NOS: 191

<210> SEQ ID NO 1
<211> LENGTH: 184
<212> TYPE: PRT
<213> ORGANISM: Mus musculus

<400> SEQUENCE: 1

Met Pro Leu Arg His Leu Ala Asp Arg Leu Gly His Leu Ala Asp Arg
1               5                   10                  15

Leu Arg His Leu Thr Asp Arg Leu Arg His Leu Ala Asp Arg Leu Arg
                20                  25                  30

His Leu Thr Asp Arg Leu Arg His Leu Ala Asp Arg Leu Arg His Leu
            35                  40                  45

Ala Asp Arg Leu Lys His Leu Thr Ser Arg Leu Gly His Leu Thr Asp
        50                  55                  60

Arg Ser Trp His Leu Thr Asp Arg Leu Gly His Leu Thr Asp Arg Leu
65                  70                  75                  80

Arg His Leu Thr Asp Arg Leu Gly His Leu Thr Asp Arg Gln Arg Tyr
                85                  90                  95

Leu Ala Asp Arg Leu Arg His Leu Thr Asp Arg Leu Gly His Leu Thr
                100                 105                 110

Asp Arg Leu Arg His Leu Thr Asp Arg Leu Gly His Leu Thr Asp Arg
            115                 120                 125

Leu Arg His Leu Thr Asp Arg Leu Gly His Leu Thr Asp Arg Leu Met
        130                 135                 140

His Leu Thr Asp Arg Leu Arg His Leu Ala Asp Arg Gln Arg His Leu
145                 150                 155                 160

Ala Asp Arg Gln Arg His Leu Ala Asp Arg Leu Arg His Leu Ala Asp
                165                 170                 175

Lys Leu Arg His Gln Leu Gln Leu
            180

<210> SEQ ID NO 2
<211> LENGTH: 55
<212> TYPE: PRT
<213> ORGANISM: Mus musculus

<400> SEQUENCE: 2

Asp Lys Leu Arg His Leu Thr Asp Arg Leu Gly His Leu Thr Asp Arg
1               5                   10                  15

Leu Arg His Leu Thr Asp Arg Leu Gly His Leu Thr Asp Arg Leu Met
                20                  25                  30

-continued

```
His Leu Thr Asp Arg Leu Met His Leu Thr Asp Arg Leu Arg His Leu
        35                  40                  45

Ala Asp Arg Gln Arg His Asp
    50                  55

<210> SEQ ID NO 3
<211> LENGTH: 55
<212> TYPE: PRT
<213> ORGANISM: Mus musculus

<400> SEQUENCE: 3

Asp Arg Leu Arg His Leu Thr Asp Arg Leu Gly His Leu Thr Asp Arg
1               5                  10                  15

Leu Arg His Leu Thr Asp Arg Leu Gly His Val Thr Asp Arg Leu Met
            20                  25                  30

His Leu Thr Asp Arg Leu Met His Leu Thr Asp Arg Leu Arg His Leu
        35                  40                  45

Ala Asp Arg Gln Arg His Asp
    50                  55

<210> SEQ ID NO 4
<211> LENGTH: 38
<212> TYPE: PRT
<213> ORGANISM: Mus musculus

<400> SEQUENCE: 4

Thr Asp Arg Leu Gly His Leu Thr Asp Arg Leu Arg His Leu Thr Asp
1               5                  10                  15

Arg Leu Gly His Leu Thr Asp Arg Leu Met His Leu Thr Asp Arg Leu
            20                  25                  30

Ser His Pro Thr Gln Thr
        35

<210> SEQ ID NO 5
<211> LENGTH: 45
<212> TYPE: PRT
<213> ORGANISM: Mus musculus

<400> SEQUENCE: 5

Asp Arg Leu Gly His Leu Thr Asp Arg Leu Lys His Leu Thr Asp Arg
1               5                  10                  15

Leu Gly His Leu Thr Asp Arg Leu Val His Leu Thr Asp Arg Leu Met
            20                  25                  30

His Leu Thr Asp Arg Leu Arg His Leu Ala Val Arg Gln
        35                  40                  45

<210> SEQ ID NO 6
<211> LENGTH: 55
<212> TYPE: PRT
<213> ORGANISM: Mus musculus

<400> SEQUENCE: 6

Asp Lys Leu Arg His Leu Thr Asp Arg Leu Gly His Leu Thr Asp Arg
1               5                  10                  15

Leu Arg His Leu Thr Asp Arg Leu Gly His Leu Thr Asp Arg Leu Met
            20                  25                  30

His Leu Thr Asp Arg Leu Met His Leu Thr Asp Arg Leu Arg His Leu
        35                  40                  45

Ala Asp Arg Arg Arg His Asp
    50                  55
```

-continued

<210> SEQ ID NO 7
<211> LENGTH: 55
<212> TYPE: PRT
<213> ORGANISM: Mus musculus

<400> SEQUENCE: 7

Asp Lys Leu Arg His Leu Thr Asp Arg Leu Gly His Leu Thr Asp Arg
1               5                   10                  15

Leu Arg His Leu Thr Asp Arg Leu Gly His Leu Thr Asp Arg Leu Met
            20                  25                  30

His Leu Thr Asp Arg Leu Met His Leu Thr Asp Arg Pro Arg His Leu
        35                  40                  45

Ala Asp Arg Gln Arg His Asp
    50                  55

<210> SEQ ID NO 8
<211> LENGTH: 55
<212> TYPE: PRT
<213> ORGANISM: Mus musculus

<400> SEQUENCE: 8

Asp Lys Leu Arg His Leu Thr Asp Arg Leu Gly His Leu Thr Asp Arg
1               5                   10                  15

Leu Arg His Leu Thr Asp Arg Leu Gly His Leu Thr Asp Arg Leu Met
            20                  25                  30

His Leu Thr Asp Arg Leu Met His Leu Thr Asp Arg Leu Gly His Leu
        35                  40                  45

Ala Asp Arg Gln Arg His Asp
    50                  55

<210> SEQ ID NO 9
<211> LENGTH: 45
<212> TYPE: PRT
<213> ORGANISM: Mus musculus

<400> SEQUENCE: 9

Asp Arg Leu Gly His Leu Thr Asp Arg Leu Lys His Leu Thr Asp Arg
1               5                   10                  15

Leu Gly His Leu Thr Asp Arg Leu Ile His Leu Thr Asp Arg Leu Met
            20                  25                  30

His Leu Thr Asp Arg Leu Arg His Leu Ala Val Arg Gln
        35                  40                  45

<210> SEQ ID NO 10
<211> LENGTH: 38
<212> TYPE: PRT
<213> ORGANISM: Mus musculus

<400> SEQUENCE: 10

Gly His Leu Thr Asp Arg Leu Arg His Leu Thr Asp Arg Leu Gly His
1               5                   10                  15

Leu Thr Asp Arg Leu Met His Leu Thr Asp Arg Leu Met His Leu Thr
            20                  25                  30

Asp Arg Leu Arg Gln Arg
        35

<210> SEQ ID NO 11
<211> LENGTH: 31
<212> TYPE: PRT

```
<213> ORGANISM: Mus musculus

<400> SEQUENCE: 11

Gly His Leu Thr Asp Arg Leu Met His Leu Thr Asp Arg Leu Met His
1               5                   10                  15

Leu Thr Asp Arg Leu Arg His Leu Ala Asp Arg Gln Arg His Asp
            20                  25                  30

<210> SEQ ID NO 12
<211> LENGTH: 38
<212> TYPE: PRT
<213> ORGANISM: Mus musculus

<400> SEQUENCE: 12

Thr Asp Gly Leu Gly His Leu Thr Asp Arg Leu Arg His Leu Thr Asp
1               5                   10                  15

Arg Leu Gly His Leu Thr Asp Arg Leu Met His Leu Thr Asp Arg Leu
            20                  25                  30

Arg His Leu Ala Asp Gln
            35

<210> SEQ ID NO 13
<211> LENGTH: 45
<212> TYPE: PRT
<213> ORGANISM: Mus musculus

<400> SEQUENCE: 13

Asp Arg Leu Gly His Leu Thr Asp Ile Leu Lys His Leu Thr Asp Arg
1               5                   10                  15

Leu Gly His Leu Thr Asp Arg Leu Ile His Leu Thr Asp Arg Leu Met
            20                  25                  30

His Leu Thr Asp Arg Leu Arg His Leu Ala Val Arg Gln
            35                  40                  45

<210> SEQ ID NO 14
<211> LENGTH: 55
<212> TYPE: PRT
<213> ORGANISM: Mus musculus

<400> SEQUENCE: 14

Asp Lys Leu Arg His Leu Thr Asp Arg Leu Gly His Leu Thr Asp Arg
1               5                   10                  15

Leu Arg His Leu Thr Asp Arg Leu Gly His Leu Thr Asp Arg Leu Met
            20                  25                  30

Arg Leu Thr Asp Arg Leu Met His Leu Thr Asp Arg Leu Arg His Leu
            35                  40                  45

Ala Asp Arg Gln Arg His Asp
            50                  55

<210> SEQ ID NO 15
<211> LENGTH: 281
<212> TYPE: PRT
<213> ORGANISM: Mus musculus

<400> SEQUENCE: 15

Met Ala Thr Asn Phe Leu Ala His Glu Lys Ile Trp Phe Asp Lys Phe
1               5                   10                  15

Lys Tyr Asp Asp Ala Glu Arg Arg Phe Tyr Glu Gln Met Asn Gly Pro
            20                  25                  30

Val Thr Ser Gly Ser Arg Gln Glu Asn Gly Ala Ser Val Ile Leu Arg
```

-continued

```
                35                  40                  45
Asp Ile Arg Ala Arg Glu Asn Ile Gln Lys Ser Leu Ala Gly Ser
 50                  55                  60

Ser Gly Pro Gly Ala Ser Ser Pro Gly Gly Asp His Ser Glu Leu
 65                  70                  75                  80

Ile Val Arg Ile Thr Ser Leu Glu Val Glu Asn Gln Asn Leu Arg Gly
                 85                  90                  95

Val Val Gln Asp Leu Gln Gln Ala Ile Ser Lys Leu Glu Ala Arg Leu
                100                 105                 110

Ser Ser Leu Glu Lys Ser Ser Pro Thr Pro Arg Ala Thr Ala Pro Gln
                115                 120                 125

Thr Gln His Val Ser Pro Met Arg Gln Val Glu Pro Pro Thr Lys Lys
                130                 135                 140

Gly Ala Thr Pro Ala Glu Asp Asp Glu Asp Lys Asp Ile Asp Leu Phe
145                 150                 155                 160

Gly Ser Asp Glu Glu Glu Glu Asp Lys Glu Ala Ala Arg Leu Arg Glu
                165                 170                 175

Glu Arg Leu Arg Gln Tyr Ala Glu Lys Lys Ala Lys Lys Pro Thr Leu
                180                 185                 190

Val Ala Lys Ser Ser Ile Leu Leu Asp Val Lys Pro Trp Asp Asp Glu
                195                 200                 205

Thr Asp Met Ala Gln Leu Glu Thr Cys Val Arg Ser Ile Gln Leu Asp
210                 215                 220

Gly Leu Val Trp Gly Ala Ser Lys Leu Val Pro Val Gly Tyr Gly Ile
225                 230                 235                 240

Arg Lys Leu Gln Ile Gln Cys Val Val Glu Asp Asp Lys Val Gly Thr
                245                 250                 255

Asp Leu Leu Glu Glu Glu Ile Thr Lys Phe Glu Glu His Val Gln Ser
                260                 265                 270

Val Asp Ile Ala Ala Phe Asp Lys Ile
                275                 280
```

<210> SEQ ID NO 16
<211> LENGTH: 54
<212> TYPE: PRT
<213> ORGANISM: Mus musculus

<400> SEQUENCE: 16

```
His Ser Glu Leu Ile Val Arg Ile Thr Ser Leu Glu Val Glu Asn Gln
 1               5                  10                  15

Asn Leu Arg Gly Val Val Gln Asp Leu Gln Gln Ala Ile Ser Lys Leu
                20                  25                  30

Glu Ala Arg Leu Ser Ser Leu Glu Lys Ser Ser Pro Thr Pro Arg Ala
                35                  40                  45

Thr Ala Pro Gln Thr Arg
                50
```

<210> SEQ ID NO 17
<211> LENGTH: 53
<212> TYPE: PRT
<213> ORGANISM: Mus musculus

<400> SEQUENCE: 17

```
Arg Glu Leu Ile Val Arg Ile Thr Ser Leu Glu Val Glu Asn Gln Asn
 1               5                  10                  15

Leu Arg Gly Val Val Gln Asp Leu Gln Gln Val Ile Ser Lys Leu Glu
```

20                  25                  30

Ala Arg Leu Ser Ser Leu Glu Lys Ser Ser Pro Thr Pro Arg Ala Thr
                35                  40                  45

Ala Pro Gln Thr Arg
    50

<210> SEQ ID NO 18
<211> LENGTH: 54
<212> TYPE: PRT
<213> ORGANISM: Mus musculus

<400> SEQUENCE: 18

His Ser Glu Leu Ile Val Arg Ile Asn Ser Leu Glu Val Glu Asn Gln
1               5                   10                  15

Asn Leu Arg Gly Val Val Gln Asp Leu Gln Gln Ala Ile Ser Lys Leu
                20                  25                  30

Glu Ala Arg Leu Ser Ser Leu Glu Lys Ser Ser Pro Thr Pro Arg Ala
                35                  40                  45

Thr Ala Pro Arg Thr Arg
    50

<210> SEQ ID NO 19
<211> LENGTH: 54
<212> TYPE: PRT
<213> ORGANISM: Mus musculus

<400> SEQUENCE: 19

His Ser Glu Leu Ile Val Arg Ile Thr Ser Leu Glu Val Glu Asn Gln
1               5                   10                  15

Asn Leu Arg Gly Val Val Gln Asp Leu Gln Gln Ala Ile Ser Arg Leu
                20                  25                  30

Glu Ala Arg Leu Ser Ser Leu Glu Lys Ser Ser Pro Thr Pro Arg Ala
                35                  40                  45

Thr Ala Pro Gln Thr Arg
    50

<210> SEQ ID NO 20
<211> LENGTH: 268
<212> TYPE: PRT
<213> ORGANISM: Mus musculus

<400> SEQUENCE: 20

Met Leu Ser Ala Phe Pro Ala Gln Leu Ala Gln Gln Ser Phe Gly
1               5                   10                  15

Val Cys Val Leu Gly Cys Thr Glu Met Val His Gln Glu Asn Cys Ser
                20                  25                  30

Tyr Gln Ala Gln Lys Asn Glu Arg Glu Ser Ile Arg Gln Lys Leu Ala
                35                  40                  45

Leu Gly Ser Phe Phe Asp Asp Gly Pro Gly Ile Tyr Thr Ser Cys Ser
            50                  55                  60

Lys Ser Gly Lys Pro Ser Leu Ser Ala Arg Leu Gln Ser Gly Met Asn
65                  70                  75                  80

Leu Gln Ile Cys Phe Val Asn Asp Ser Gly Ser Asp Lys Asp Ser Asp
                85                  90                  95

Ala Asp Asp Ser Lys Thr Glu Thr Ser Leu Asp Thr Pro Leu Ser Pro
                100                 105                 110

Met Ser Lys Gln Ser Ser Ser Tyr Ser Asp Arg Asp Thr Thr Glu Glu
                115                 120                 125

```
Glu Ser Glu Ser Leu Asp Asp Met Asp Phe Leu Thr Arg Gln Lys Lys
        130                 135                 140

Leu Gln Ala Glu Ala Lys Met Ala Leu Ala Met Ala Lys Pro Met Ala
145                 150                 155                 160

Lys Met Gln Val Glu Val Arg Gln Asn Arg Lys Lys Ser Pro Val
                165                 170                 175

Ala Asp Leu Leu Pro His Met Pro His Ile Ser Glu Cys Leu Met Lys
                180                 185                 190

Arg Ser Leu Lys Pro Thr Asp Leu Arg Asp Met Thr Ile Gly Gln Leu
            195                 200                 205

Gln Val Ile Val Asn Asp Leu His Ser Gln Ile Glu Ser Leu Asn Glu
        210                 215                 220

Glu Leu Val Gln Leu Leu Ile Arg Asp Glu Leu His Thr Glu Gln
225                 230                 235                 240

Asp Ala Met Leu Val Asp Ile Glu Asp Leu Thr Arg His Ala Glu Ser
                245                 250                 255

Gln Gln Lys His Met Ala Glu Lys Met Pro Ala Lys
            260                 265

<210> SEQ ID NO 21
<211> LENGTH: 78
<212> TYPE: PRT
<213> ORGANISM: Mus musculus

<400> SEQUENCE: 21

Pro His Thr Pro His Ile Ser Glu Cys Leu Met Lys Arg Ser Leu Lys
1               5                   10                  15

Pro Thr Asp Leu Arg Asp Met Thr Ile Gly Gln Leu Gln Val Ile Val
            20                  25                  30

Asn Asp Leu His Ser Gln Ile Glu Ser Leu Asn Glu Glu Leu Val Gln
        35                  40                  45

Leu Leu Leu Ile Arg Asp Glu Leu His Thr Glu Gln Asp Ala Met Leu
    50                  55                  60

Val Asp Ile Glu Asp Leu Thr Arg His Ala Glu Arg Glu Gln
65                  70                  75

<210> SEQ ID NO 22
<211> LENGTH: 78
<212> TYPE: PRT
<213> ORGANISM: Mus musculus

<400> SEQUENCE: 22

Pro His Met Pro His Ile Ser Glu Cys Leu Met Lys Arg Ser Leu Lys
1               5                   10                  15

Pro Thr Asp Leu Arg Asp Met Thr Ile Gly Gln Leu Gln Val Ile Val
            20                  25                  30

Asn Asp Leu His Ser Gln Ile Glu Arg Leu Asn Glu Glu Leu Val Gln
        35                  40                  45

Leu Leu Leu Ile Arg Asp Glu Leu His Thr Glu Gln Asp Ala Met Leu
    50                  55                  60

Val Asp Ile Glu Asp Leu Thr Arg His Ala Glu Lys Glu Gln
65                  70                  75

<210> SEQ ID NO 23
<211> LENGTH: 552
<212> TYPE: DNA
<213> ORGANISM: Mus musculus
```

-continued

<400> SEQUENCE: 23

| | | |
|---|---|---|
| atgccattga ggcatctagc agacagattg gggcatctgg cagacagact gaggcatcta | 60 |
| acagacagat tgaggcatct agcagacaga ctgaggcatt aacagacag attgaggcat | 120 |
| ctagcagaca gattgaggca tctagcagac agactgaaac atcttaccag cagattgggg | 180 |
| catctaacag acagatcatg gcatctaaca gacagattgg ggcatctaac agacagattg | 240 |
| aggcatctaa cagacagatt ggggcatcta acagacagac agaggtatct agcagacaga | 300 |
| ttgaggcatc taacagacag attggggcat ctaacagaca gactgaggca tctaacagac | 360 |
| agattggggc atctaacaga cagactgagg catctaacag acagattggg gcatctaaca | 420 |
| gacagactga tgcatctaac agacagactg aggcatctag cagacagaca gaggcatcta | 480 |
| gcagacagac agaggcatct agcagacaga ctgaggcatc tagcagacaa attgaggcat | 540 |
| cagctgcagc tg | 552 |

<210> SEQ ID NO 24
<211> LENGTH: 165
<212> TYPE: DNA
<213> ORGANISM: Mus musculus

<400> SEQUENCE: 24

| | | |
|---|---|---|
| gacaaactga ggcatctaac agacagattg gggcatctaa cagacagact gaggcatcta | 60 |
| acagacagat tggggcatct aacagacaga ctgatgcatc taacagacag actgatgcat | 120 |
| ctaacagaca gactgaggca tctagcagac agacagaggc acgac | 165 |

<210> SEQ ID NO 25
<211> LENGTH: 165
<212> TYPE: DNA
<213> ORGANISM: Mus musculus

<400> SEQUENCE: 25

| | | |
|---|---|---|
| gacaaactga ggcatctaac agacagattg gggcatctaa cagacaggct gaggcatcta | 60 |
| acagacagat tggggcatct aacagacaga ctgatgcatc taacagacag actgatgcat | 120 |
| ctaacagaca gactgaggca tctagcagac agacagaggc acgac | 165 |

<210> SEQ ID NO 26
<211> LENGTH: 165
<212> TYPE: DNA
<213> ORGANISM: Mus musculus

<400> SEQUENCE: 26

| | | |
|---|---|---|
| gacaaactga ggcatctaac agacagattg gggcatctaa cagacagact gaggcatcta | 60 |
| acagacagat tggggcatct aacagacaga ctgatgcatc taacagacag actgatgcat | 120 |
| ctaacagaca gactgaggca tctagcagac aggcagaggc acgac | 165 |

<210> SEQ ID NO 27
<211> LENGTH: 165
<212> TYPE: DNA
<213> ORGANISM: Mus musculus

<400> SEQUENCE: 27

| | | |
|---|---|---|
| gacagactga ggcatctaac agacagattg gggcatttaa cagacagact gaggcattta | 60 |
| acagacagat tggggcatgt aacagacaga ctgatgcatt aacagacag actgatgcat | 120 |
| ctaacagaca gactgaggca tttagcagac agacagaggc acgac | 165 |

<210> SEQ ID NO 28
<211> LENGTH: 114
<212> TYPE: DNA
<213> ORGANISM: Mus musculus

<400> SEQUENCE: 28
acagacagat tggggcatct aacagacaga ctgaggcatc taacagacag attggggcat      60
ctaacagaca gactgatgca tctaacagac agactgagcc atcctacgca gacc            114

<210> SEQ ID NO 29
<211> LENGTH: 135
<212> TYPE: DNA
<213> ORGANISM: Mus musculus

<400> SEQUENCE: 29
gacagattgg ggcatctaac agacagactg aagcatctaa cagacagatt ggggcatcta      60
acagacagac tggtccatct aacagacaga ctgatgcatc taacagacag actgaggcat     120
ctagcagtta gacag                                                      135

<210> SEQ ID NO 30
<211> LENGTH: 165
<212> TYPE: DNA
<213> ORGANISM: Mus musculus

<400> SEQUENCE: 30
gacaaactga ggcatctaac agacagattg gggcatctaa cagacagact gaggcatcta      60
acagacagat tggggcatct aacagacaga ctgatgcatc taacagacag actgatgcat     120
ctaacagaca gactgaggca tctagcagac agacggaggc acgac                     165

<210> SEQ ID NO 31
<211> LENGTH: 165
<212> TYPE: DNA
<213> ORGANISM: Mus musculus

<400> SEQUENCE: 31
gacaaactga ggcatctaac agacagattg gggcatctaa cagacagact gaggcatcta      60
acagacagat tggggcatct aacagacaga ctgatgcatc taacagacag actgatgcac     120
taacagacac gaccgaggca tctagcagac agacagaggc acgac                     165

<210> SEQ ID NO 32
<211> LENGTH: 165
<212> TYPE: DNA
<213> ORGANISM: Mus musculus

<400> SEQUENCE: 32
gacaaactga ggcatctaac agacagattg gggcatctaa cagacagact gaggcatcta      60
acagacagat tggggcatct aacagacaga ctgatgcatc taacagacag actgatgcat     120
ctaacagaca gactggggca tctagcagac agacagaggc acgac                     165

<210> SEQ ID NO 33
<211> LENGTH: 135
<212> TYPE: DNA
<213> ORGANISM: Mus musculus

<400> SEQUENCE: 33
gacagattgg ggcatctaac agacagactg aagcatctaa cagacagatt ggggcatcta      60
acagacagac tgatccatct aacagacaga ctgatgcatc taacagacag actgaggcat     120

```
ctagcagtca gacag                                                      135

<210> SEQ ID NO 34
<211> LENGTH: 114
<212> TYPE: DNA
<213> ORGANISM: Mus musculus

<400> SEQUENCE: 34
gggcatctaa cagacagact gaggcatcta acagacagat tggggcatct aacagacaga     60
ctgatgcatc taacagacag actgatgcat ctaacagaca gactgaggca aaga          114

<210> SEQ ID NO 35
<211> LENGTH: 93
<212> TYPE: DNA
<213> ORGANISM: Mus musculus

<400> SEQUENCE: 35
gggcatctaa cagacagact gatgcatcta acagacagac tgatgcatct aacagacaga     60
ctgaggcatc tagcagacag acagaggcac gac                                  93

<210> SEQ ID NO 36
<211> LENGTH: 114
<212> TYPE: DNA
<213> ORGANISM: Mus musculus

<400> SEQUENCE: 36
acagacggat tggggcatct aacagacaga ctgaggcatc taacagacag attggggcat     60
ctaacagaca gactgatgca tctaacagac agactgaggc atctagcaga ccag          114

<210> SEQ ID NO 37
<211> LENGTH: 135
<212> TYPE: DNA
<213> ORGANISM: Mus musculus

<400> SEQUENCE: 37
gacagattgg ggcatctaac agacatactg aagcatctaa cagacagatt ggggcatcta     60
acagacagac tgatccatct aacagacaga ctgatgcatc taacagacag actgaggcat    120
ctagcagtca gacag                                                     135

<210> SEQ ID NO 38
<211> LENGTH: 165
<212> TYPE: DNA
<213> ORGANISM: Mus musculus

<400> SEQUENCE: 38
gacaaactga ggcatctaac agacagattg ggcatctaa cagacagact gaggcatcta     60
acagacagat tggggcatct aacagacaga ctgatgcgtc taacagacag actgatgcat    120
ctaacagaca gactgaggca tctagcagac agacagaggc acgac                    165

<210> SEQ ID NO 39
<211> LENGTH: 843
<212> TYPE: DNA
<213> ORGANISM: Mus musculus

<400> SEQUENCE: 39
atggctacaa actttctagc gcatgagaag atctggtttg acaagtttaa atatgatgat     60
gcagaaagga gattctatga gcagatgaac gggcctgtga cctccggctc ccgccaggag    120
```

-continued

| | |
|---|---|
| aatggtgcca gcgtgatcct ccgagacatt gcaagagcca gagagaacat ccagaaatcc | 180 |
| ttggctggaa gctcaggccc tggagcctcc agtggacctg gtggagacca cagtgagctc | 240 |
| attgtgagga ttaccagtct ggaagtggag aaccagaacc ttcgaggcgt ggtgcaagat | 300 |
| ttgcagcagg ccatttccaa gttggaggcc cggctgagct ctctagagaa gagttcacct | 360 |
| actccccgag ccacggcccc acagacccaa catgtctctc tatgcgtca agtggagccc | 420 |
| ccaaccaaga aggagccac accagcagag gacgatgagg acaaggacat tgacctgttc | 480 |
| ggcagtgacg aggaggaaga agataaggag gctgcccgac tacggaggag gaggctacgc | 540 |
| cagtacgcag agaagaaggc caagaagccc acactggtgg ccaaatcctc catccttttg | 600 |
| gatgttaaac cttgggatga tgagactgac atggcccagc tagagacttg tgtgcgttcc | 660 |
| atccaattgg acgggctggt ttgggggggcc tccaagcttg tgcctgttgg ctatggcatc | 720 |
| cggaagctgc agatccagtg tgtggtggag gatgacaaag tgggcaccga cttgctcgag | 780 |
| gaggagatca ccaaatttga ggagcatgtg cagagtgtcg acatcgcagc tttcgacaag | 840 |
| atc | 843 |

<210> SEQ ID NO 40
<211> LENGTH: 162
<212> TYPE: DNA
<213> ORGANISM: Mus musculus

<400> SEQUENCE: 40

| | |
|---|---|
| cacagtgagc tcattgtgag gattaccagt ctggaagtgg agaatcagaa ccttcgaggc | 60 |
| gtggtgcaag atttgcagca ggccatttcc aagttggagg cccggctgag ctctctagag | 120 |
| aagagttcac ctactccccg agccacggcc ccacagaccc ga | 162 |

<210> SEQ ID NO 41
<211> LENGTH: 159
<212> TYPE: DNA
<213> ORGANISM: Mus musculus

<400> SEQUENCE: 41

| | |
|---|---|
| cgtgagctca ttgtgaggat taccagtctg gaagtggaga atcagaacct tcgaggcgtg | 60 |
| gtgcaagatt tgcagcaggt catttccaag ttggaggccc ggctgagctc tctagagaag | 120 |
| agttcaccta ctccccgagc cacggcccca gacccga | 159 |

<210> SEQ ID NO 42
<211> LENGTH: 162
<212> TYPE: DNA
<213> ORGANISM: Mus musculus

<400> SEQUENCE: 42

| | |
|---|---|
| cacagtgagc tcattgtgag gattaacagt ttggaagtgg agaatcagaa ccttcgaggg | 60 |
| gtggtgcaag atttgcagca ggccatttcc aagttggagg cccggctgag ctctttagag | 120 |
| aagagttcac ctactccccg agccacggcc ccacggaccc ga | 162 |

<210> SEQ ID NO 43
<211> LENGTH: 162
<212> TYPE: DNA
<213> ORGANISM: Mus musculus

<400> SEQUENCE: 43

| | |
|---|---|
| cacagtgagc tcattgtgag gattaccagt ctggaagtgg agaatcagaa ccttcggggc | 60 |
| gtggtgcaag atttgcagca ggccatttcc aaggttggagg cccggctgag ctctctagag | 120 |

```
aagagttcac ctactccccg agccacggcc ccacagaccc ga        162
```

<210> SEQ ID NO 44
<211> LENGTH: 804
<212> TYPE: DNA
<213> ORGANISM: Mus musculus

<400> SEQUENCE: 44

```
atgctcagcg ctttccctgc gcagctcgcc cagcagtcca gctttggggt ctgcgtccta    60
ggatgtactg agatggtaca tcaggagaac tgctcgtacc aggcacagaa gaatgagaga   120
gagtctatca gacagaagtt ggcactcgga agcttctttg acgatggccc aggaatctat   180
accagctgca gcaaaagtgg gaagccaagc ctttctgcaa gactacagag cgggatgaac   240
ctccagatat gctttgtcaa tgacagcggc agtgacaagg acagcgatgc agatgacagt   300
aagacggaaa ccagcttgga cacgcccttg tcccccatga gcaagcagag ttcttcctat   360
tcggatagag acacaactga ggaggagtct gaatccctgg atgacatgga cttcctcaca   420
aggcaaaaga gctacaagc tgaagccaaa atggctctgg ccatggccaa accaatggcc   480
aaaatgcaag tagaagtgga aagacagaac aggaaaaagt ctcccgtcgc tgatcttctc   540
ccacacatgc ctcacataag cgaatgtttg atgaaaagaa gcttaaagcc caccgacctg   600
agagacatga ctatcgggca gctacaagtg atcgtcaatg acctccactc ccagattgaa   660
agtttgaatg aagagttggt ccagctgctc cttattcgag atgagctgca cacagaacaa   720
gatgccatgc tggtggacat tgaagacttg actagacacg ctgagagtca gcagaagcac   780
atggctgaga aaatgcccgc gaag                                          804
```

<210> SEQ ID NO 45
<211> LENGTH: 234
<212> TYPE: DNA
<213> ORGANISM: Mus musculus

<400> SEQUENCE: 45

```
ccacacacgc ctcacataag cgaatgtttg atgaaaagaa gcttaaagcc caccgacctg    60
agagacatga ctatcgggca gctacaagtg atcgtcaatg acctccactc ccagattgaa   120
agtttgaatg aagagttggt ccagctgctc cttattcgag atgagctgca cacagaacaa   180
gatgccatgc tggtggacat tgaagacttg actagacacg ctgagaggga gcag         234
```

<210> SEQ ID NO 46
<211> LENGTH: 234
<212> TYPE: DNA
<213> ORGANISM: Mus musculus

<400> SEQUENCE: 46

```
ccacacatgc ctcacataag cgaatgtttg atgaaaagaa gcttaaagcc caccgacctg    60
agagacatga ctatcgggca gctacaagtg atcgtcaatg acctccactc ccagattgag   120
cgtttgaatg aagagttggt ccagctgctc cttattcgag atgagctgca cacagaacaa   180
gatgccatgc tggtggacat tgaagacttg actagacacg ctgagaagga gcag         234
```

<210> SEQ ID NO 47
<211> LENGTH: 191
<212> TYPE: PRT
<213> ORGANISM: Mus musculus

<400> SEQUENCE: 47

Met Pro Leu Arg His Leu Ala Asp Arg Leu Gly His Leu Ala Asp Arg
1               5                   10                  15

Leu Arg His Leu Thr Asp Arg Leu Arg His Leu Ala Asp Arg Leu Arg
            20                  25                  30

His Leu Thr Asp Arg Leu Arg His Leu Ala Asp Arg Leu Lys His Leu
        35                  40                  45

Ala Asp Arg Leu Lys His Leu Thr Asp Arg Leu Gly His Leu Thr Asp
    50                  55                  60

Arg Ser Trp His Leu Thr Asp Arg Leu Gly His Leu Thr Asp Arg Leu
65                  70                  75                  80

Arg His Leu Thr Asp Arg Leu Gly His Leu Thr Asp Arg Gln Arg Tyr
            85                  90                  95

Leu Ala Asp Arg Leu Arg His Leu Thr Asp Arg Leu Gly His Leu Thr
                100                 105                 110

Asp Lys Leu Arg His Leu Thr Asp Arg Leu Gly His Leu Thr Asp Arg
        115                 120                 125

Leu Arg His Leu Thr Asp Arg Leu Gly His Leu Thr Asp Arg Leu Met
    130                 135                 140

His Leu Thr Asp Arg Leu Met His Leu Thr Asp Arg Leu Arg His Leu
145                 150                 155                 160

Ala Asp Arg Gln Arg His Leu Ala Asp Arg Gln Arg His Leu Ala Asp
            165                 170                 175

Arg Leu Arg His Leu Ala Asp Lys Leu Arg His Gln Leu Gln Leu
            180                 185                 190

<210> SEQ ID NO 48
<211> LENGTH: 71
<212> TYPE: PRT
<213> ORGANISM: Mus musculus

<400> SEQUENCE: 48

Ile Glu Ala Ser Asn Arg Gln Ile Gly Ala Ser Asn Arg Gln Thr Glu
1               5                   10                  15

Ala Ser Asn Arg Gln Ile Gly His Leu Thr Asp Arg Leu Arg His Leu
            20                  25                  30

Thr Asp Arg Leu Gly His Leu Thr Asp Arg Leu Met His Leu Thr Asp
        35                  40                  45

Arg Leu Met His Leu Thr Asp Arg Leu Arg His Leu Ala Asp Arg Gln
    50                  55                  60

Arg His Leu Ala Asp Arg Leu
65                  70

<210> SEQ ID NO 49
<211> LENGTH: 55
<212> TYPE: PRT
<213> ORGANISM: Mus musculus

<400> SEQUENCE: 49

Asp Lys Leu Arg His Leu Thr Asp Arg Leu Gly His Leu Thr Asp Arg
1               5                   10                  15

Leu Arg His Leu Thr Asp Arg Leu Gly His Leu Thr Asp Arg Leu Met
            20                  25                  30

His Leu Thr Asp Arg Leu Met His Leu Thr Asp Arg Leu Arg His Leu
        35                  40                  45

Ala Asp Arg Gln Arg His Asp
    50                  55

```
<210> SEQ ID NO 50
<211> LENGTH: 45
<212> TYPE: PRT
<213> ORGANISM: Mus musculus

<400> SEQUENCE: 50

Asp Arg Leu Gly His Leu Thr Asp Arg Leu Arg His Leu Thr Asp Arg
1               5                   10                  15

Leu Gly His Leu Thr Asp Arg Leu Met His Leu Thr Asp Arg Leu Met
            20                  25                  30

His Leu Thr Asp Arg Leu Arg His Leu Ala Val Arg Gln
        35                  40                  45

<210> SEQ ID NO 51
<211> LENGTH: 45
<212> TYPE: PRT
<213> ORGANISM: Mus musculus

<400> SEQUENCE: 51

Asp Arg Leu Gly Arg Leu Thr Asp Arg Leu Arg His Leu Thr Asp Arg
1               5                   10                  15

Leu Gly His Leu Thr Asp Arg Leu Met His Leu Thr Asp Arg Leu Met
            20                  25                  30

His Leu Thr Asp Arg Leu Arg His Leu Ala Val Arg Gln
        35                  40                  45

<210> SEQ ID NO 52
<211> LENGTH: 45
<212> TYPE: PRT
<213> ORGANISM: Mus musculus

<400> SEQUENCE: 52

Asp Arg Leu Gly His Leu Thr Asp Arg Leu Arg Tyr Leu Thr Asp Arg
1               5                   10                  15

Leu Gly His Leu Thr Asp Arg Leu Met His Leu Thr Asp Arg Leu Met
            20                  25                  30

His Leu Thr Asp Arg Leu Arg His Leu Ala Val Arg Gln
        35                  40                  45

<210> SEQ ID NO 53
<211> LENGTH: 45
<212> TYPE: PRT
<213> ORGANISM: Mus musculus

<400> SEQUENCE: 53

Asp Arg Leu Gly His Leu Thr Asp Arg Leu Arg His Leu Thr Asp Arg
1               5                   10                  15

Leu Gly His Leu Thr Asp Arg Leu Met His Leu Thr Asp Arg Leu Thr
            20                  25                  30

His Leu Thr Asp Arg Leu Arg His Leu Ala Val Arg Gln
        35                  40                  45

<210> SEQ ID NO 54
<211> LENGTH: 45
<212> TYPE: PRT
<213> ORGANISM: Mus musculus

<400> SEQUENCE: 54

Asp Arg Leu Gly His Leu Thr Asp Arg Leu Lys His Leu Thr Asp Arg
1               5                   10                  15
```

```
Leu Gly His Leu Thr Asp Arg Leu Ile His Leu Thr Asp Arg Leu Met
            20                  25                  30

His Leu Thr Asp Arg Leu Arg His Leu Ala Val Arg Gln
            35                  40              45

<210> SEQ ID NO 55
<211> LENGTH: 45
<212> TYPE: PRT
<213> ORGANISM: Mus musculus

<400> SEQUENCE: 55

Gly Arg Leu Gly His Leu Thr Asp Arg Leu Arg His Leu Thr Asp Arg
1               5                   10                  15

Leu Gly His Leu Thr Asp Arg Leu Met His Leu Thr Asp Arg Leu Met
            20                  25                  30

His Leu Thr Asp Arg Leu Arg His Leu Ala Val Arg Gln
            35                  40              45

<210> SEQ ID NO 56
<211> LENGTH: 38
<212> TYPE: PRT
<213> ORGANISM: Mus musculus

<400> SEQUENCE: 56

Asp Arg Leu Arg His Leu Ala Asp Arg Leu Arg His Leu Thr Asp Arg
1               5                   10                  15

Leu Arg His Leu Ala Asp Arg Leu Lys His Leu Ala Asp Arg Leu Lys
            20                  25                  30

His Leu Thr Asn Arg Lys
        35

<210> SEQ ID NO 57
<211> LENGTH: 184
<212> TYPE: PRT
<213> ORGANISM: Mus musculus

<400> SEQUENCE: 57

Met Pro Leu Arg His Leu Ala Asp Arg Leu Gly His Leu Ala Asp Arg
1               5                   10                  15

Leu Arg His Leu Thr Asp Arg Leu Arg His Leu Ala Asp Arg Leu Arg
            20                  25                  30

His Leu Thr Asp Arg Leu Arg His Leu Ala Asp Arg Leu Arg His Leu
            35                  40                  45

Ala Asp Arg Leu Lys His Leu Thr Asp Arg Leu Gly His Leu Thr Asp
        50                  55                  60

Arg Ser Trp His Leu Thr Asp Arg Leu Gly His Leu Thr Asp Arg Leu
65                  70                  75                  80

Arg His Leu Thr Asp Arg Leu Gly His Leu Thr Asp Arg Gln Arg Tyr
                85                  90                  95

Leu Ala Asp Arg Leu Arg His Leu Thr Asp Arg Leu Gly His Leu Thr
                100                 105                 110

Asp Arg Leu Arg His Leu Thr Asp Arg Leu Gly His Leu Thr Asp Arg
            115                 120                 125

Leu Arg His Leu Thr Asp Arg Leu Gly His Leu Thr Asp Arg Leu Met
            130                 135                 140

His Leu Thr Asp Arg Leu Arg His Leu Ala Asp Arg Gln Arg His Leu
145                 150                 155                 160

Ala Asp Arg Gln Arg His Leu Ala Asp Arg Leu Arg His Leu Ala Asp
```

165                 170                 175

Lys Leu Arg His Gln Leu Gln Leu
                180

<210> SEQ ID NO 58
<211> LENGTH: 79
<212> TYPE: PRT
<213> ORGANISM: Mus musculus

<400> SEQUENCE: 58

Glu Lys Val Lys Thr Leu Lys Ala Gln Asn Ser Glu Leu Ala Ser Thr
1               5                   10                  15

Ala Asn Thr Leu Arg Glu Gln Val Ala Leu Leu Lys Gln Lys Val Met
            20                  25                  30

Asn His Val Asn Ser Gly Cys Gln Leu Met Leu Thr Gln Gln Leu Gln
        35                  40                  45

Thr Phe Trp Glu Gln Thr Val Arg Ala Glu Gly Gln Trp Lys Lys Lys
    50                  55                  60

Asn Asn Arg Asp Lys Leu Glu Asn Leu Thr Gly Cys Asp Arg Glu
65                  70                  75

<210> SEQ ID NO 59
<211> LENGTH: 76
<212> TYPE: PRT
<213> ORGANISM: Mus musculus

<400> SEQUENCE: 59

Arg Ile Lys Ala Glu Arg Lys Arg Met Arg Asn Arg Ile Ala Ala Ser
1               5                   10                  15

Glu Cys Arg Lys Arg Lys Leu Glu Arg Ile Ala Arg Leu Glu Glu Lys
            20                  25                  30

Val Lys Thr Leu Lys Ala Gln Asn Ser Glu Leu Ala Ser Thr Ala Asn
        35                  40                  45

Met Leu Arg Glu Gln Val Ala Gln Leu Lys Gln Lys Val Met Asn His
    50                  55                  60

Val Asn Ser Gly Cys Gln Leu Met Leu Thr Gln Gln
65                  70                  75

<210> SEQ ID NO 60
<211> LENGTH: 49
<212> TYPE: PRT
<213> ORGANISM: Mus musculus

<400> SEQUENCE: 60

Gly His Leu Ala Asp Arg Leu Arg His Leu Thr Asp Arg Leu Arg His
1               5                   10                  15

Leu Ala Asp Arg Leu Arg His Leu Thr Asp Arg Leu Arg His Leu Ala
            20                  25                  30

Asp Arg Leu Arg His Leu Ala Asp Arg Leu Lys His Leu Thr Asp Arg
        35                  40                  45

Tyr

<210> SEQ ID NO 61
<211> LENGTH: 56
<212> TYPE: PRT
<213> ORGANISM: Mus musculus

<400> SEQUENCE: 61

His Leu Thr Asp Arg Leu Arg His Leu Thr Asp Arg Leu Gly His Leu

```
                1               5                  10                  15
Thr Asp Arg Leu Arg His Leu Thr Asp Arg Leu Arg His Leu Thr Asp
                    20                  25                  30
Arg Leu Met His Leu Thr Asp Arg Leu Gly His Leu Ala Asp Arg Gln
            35                  40                  45
Arg His Leu Ala Asp Arg Gln Arg
        50                  55

<210> SEQ ID NO 62
<211> LENGTH: 44
<212> TYPE: PRT
<213> ORGANISM: Mus musculus

<400> SEQUENCE: 62

Ala Asp Arg Leu Gly His Leu Ala Asp Arg Leu Arg His Leu Thr Asp
1               5                   10                  15
Arg Leu Arg His Leu Ala Asp Arg Leu Arg His Leu Thr Asp Arg Leu
                    20                  25                  30
Arg His Leu Ala Asp Arg Leu Arg His Leu Ala Asp
            35                  40

<210> SEQ ID NO 63
<211> LENGTH: 27
<212> TYPE: PRT
<213> ORGANISM: Mus musculus

<400> SEQUENCE: 63

Ala Asp Arg Leu Arg His Leu Thr Asp Arg Leu Arg His Leu Ala Asp
1               5                   10                  15
Arg Leu Arg His Leu Thr Asp Arg Leu Arg His
                    20                  25

<210> SEQ ID NO 64
<211> LENGTH: 53
<212> TYPE: PRT
<213> ORGANISM: Mus musculus

<400> SEQUENCE: 64

Thr Asp Arg Leu Gly His Leu Thr Asp Arg Leu Arg His Leu Thr Asp
1               5                   10                  15
Arg Leu Gly His Leu Thr Asp Arg Leu Arg His Leu Thr Asp Arg Leu
                    20                  25                  30
Gly His Leu Thr Asp Arg Leu Met His Leu Thr Asp Arg Leu Arg His
            35                  40                  45
Leu Ala Asp Arg Pro
        50

<210> SEQ ID NO 65
<211> LENGTH: 46
<212> TYPE: PRT
<213> ORGANISM: Mus musculus

<400> SEQUENCE: 65

Arg Gln Arg His Leu Thr Asp Arg Leu Arg His Leu Thr Asp Arg Leu
1               5                   10                  15
Gly His Leu Thr Asp Arg Leu Arg His Leu Thr Asp Arg Leu Gly His
                    20                  25                  30
Leu Thr Asp Arg Leu Met His Leu Thr Asp Arg Leu Arg Pro
            35                  40                  45
```

<210> SEQ ID NO 66
<211> LENGTH: 39
<212> TYPE: PRT
<213> ORGANISM: Mus musculus

<400> SEQUENCE: 66

Asp Arg Leu Ser His Leu Ala Asp Arg Leu Arg His Leu Thr Asp Arg
1               5                   10                  15

Leu Arg His Leu Thr Asp Arg Leu Gly His Leu Thr Asp Arg Leu Arg
            20                  25                  30

His Leu Ala Asp Arg Gln Arg
        35

<210> SEQ ID NO 67
<211> LENGTH: 39
<212> TYPE: PRT
<213> ORGANISM: Mus musculus

<400> SEQUENCE: 67

Asp Arg Leu Arg His Leu Ala Asp Arg Leu Arg His Leu Thr Asp Arg
1               5                   10                  15

Leu Arg His Leu Thr Asp Arg Leu Gly His Leu Thr Asp Arg Leu Arg
            20                  25                  30

His Leu Ala Asp Arg Gln Arg
        35

<210> SEQ ID NO 68
<211> LENGTH: 39
<212> TYPE: PRT
<213> ORGANISM: Mus musculus

<400> SEQUENCE: 68

Gly Arg Leu Arg His Leu Ala Asp Arg Leu Arg His Leu Thr Asp Arg
1               5                   10                  15

Leu Arg His Leu Thr Asp Arg Leu Gly His Leu Thr Asp Arg Leu Arg
            20                  25                  30

His Leu Ala Asp Arg Gln Arg
        35

<210> SEQ ID NO 69
<211> LENGTH: 43
<212> TYPE: PRT
<213> ORGANISM: Mus musculus

<400> SEQUENCE: 69

Tyr Leu Ala Asp Arg Leu Arg His Leu Thr Asp Arg Leu Gly His Leu
1               5                   10                  15

Thr Asp Arg Leu Arg His Leu Thr Asp Arg Leu Gly His Leu Thr Asp
            20                  25                  30

Arg Leu Arg His Leu Thr Asp Arg Leu Gly Gln
        35                  40

<210> SEQ ID NO 70
<211> LENGTH: 43
<212> TYPE: PRT
<213> ORGANISM: Mus musculus

<400> SEQUENCE: 70

Tyr Leu Ala Asp Arg Leu Arg His Leu Thr Asp Arg Leu Arg His Leu
1               5                   10                  15

```
Thr Asp Arg Leu Arg His Leu Thr Asp Arg Leu Gly His Leu Thr Asp
         20                  25                  30

Arg Leu Arg His Leu Thr Asp Arg Leu Gly Gln
         35                  40

<210> SEQ ID NO 71
<211> LENGTH: 76
<212> TYPE: PRT
<213> ORGANISM: Mus musculus

<400> SEQUENCE: 71

Arg Ile Lys Ala Glu Arg Lys Arg Met Arg Asn Arg Ile Ala Ala Ser
1               5                   10                  15

Lys Cys Arg Lys Arg Lys Leu Glu Arg Ile Ala Arg Leu Glu Glu Lys
            20                  25                  30

Val Lys Thr Leu Lys Ala Gln Asn Ser Glu Leu Ala Ser Thr Ala Asn
        35                  40                  45

Met Leu Arg Glu Gln Val Ala Gln Leu Lys Gln Lys Val Met Asn His
    50                  55                  60

Val Asn Ser Gly Cys Gln Leu Met Leu Thr Gln Gln
65                  70                  75

<210> SEQ ID NO 72
<211> LENGTH: 44
<212> TYPE: PRT
<213> ORGANISM: Mus musculus

<400> SEQUENCE: 72

Leu Gly His Leu Thr Asp Arg Leu Arg His Leu Thr Asp Arg Leu Gly
1               5                   10                  15

His Leu Thr Asp Arg Leu Met His Leu Thr Asp Arg Leu Arg His Leu
            20                  25                  30

Ala Asp Arg Gln Arg His Leu Ala Asp Arg Gln Lys
        35                  40

<210> SEQ ID NO 73
<211> LENGTH: 36
<212> TYPE: PRT
<213> ORGANISM: Mus musculus

<400> SEQUENCE: 73

Leu Gly His Leu Thr Asp Arg Leu Arg His Leu Thr Asp Arg Leu Gly
1               5                   10                  15

His Leu Thr Asp Arg Leu Met His Leu Thr Asp Arg Leu Arg His Leu
            20                  25                  30

Ala Asp Thr Gln
        35

<210> SEQ ID NO 74
<211> LENGTH: 44
<212> TYPE: PRT
<213> ORGANISM: Mus musculus

<400> SEQUENCE: 74

Gly His Leu Thr Asp Arg Leu Arg His Leu Thr Asp Arg Leu Gly His
1               5                   10                  15

Leu Thr Asp Arg Leu Arg His Leu Thr Asp Arg Leu Gly His Leu Thr
            20                  25                  30

Asp Arg Leu Met His Leu Thr Asp Arg Leu Arg His
        35                  40
```

<210> SEQ ID NO 75
<211> LENGTH: 51
<212> TYPE: PRT
<213> ORGANISM: Mus musculus

<400> SEQUENCE: 75

```
Arg His Leu Thr Asp Arg Leu Gly His Leu Thr Asp Arg Leu Arg His
1               5                   10                  15
Leu Thr Asp Arg Leu Gly His Leu Thr Asp Arg Leu Met His Leu Thr
            20                  25                  30
Asp Arg Leu Arg His Leu Ala Asp Arg Gln Arg His Leu Ala Asp Arg
        35                  40                  45
Gln Arg His
    50
```

<210> SEQ ID NO 76
<211> LENGTH: 51
<212> TYPE: PRT
<213> ORGANISM: Mus musculus

<400> SEQUENCE: 76

```
Arg His Leu Thr Asp Arg Leu Gly His Leu Thr Asp Arg Leu Arg His
1               5                   10                  15
Leu Thr Asp Arg Leu Gly Arg Leu Thr Asp Arg Leu Met His Leu Thr
            20                  25                  30
Asp Arg Leu Arg His Leu Ala Asp Arg Gln Arg His Leu Ala Asp Arg
        35                  40                  45
Gln Arg His
    50
```

<210> SEQ ID NO 77
<211> LENGTH: 584
<212> TYPE: PRT
<213> ORGANISM: Mus musculus

<400> SEQUENCE: 77

```
Met Ser His Gln Pro Leu Ser Cys Leu Thr Glu Lys Gly Asp Ser Pro
1               5                   10                  15
Cys Glu Thr Pro Gly Asn Gly Pro Ser Asn Met Val His Pro Ser Leu
            20                  25                  30
Asp Thr Phe Thr Pro Glu Glu Leu Leu Gln Gln Met Lys Glu Leu Leu
        35                  40                  45
Val Glu Asn His Gln Leu Lys Glu Ala Met Lys Leu Asn Asn Gln Ala
    50                  55                  60
Met Lys Gly Arg Phe Glu Glu Leu Ser Ala Trp Thr Glu Lys Gln Lys
65                  70                  75                  80
Glu Glu Arg Leu Leu Phe Glu Met Gln Ser Lys Glu Val Lys Glu Arg
                85                  90                  95
Leu Lys Ala Leu Thr His Glu Asn Glu Arg Leu Lys Glu Glu Leu Gly
            100                 105                 110
Lys Phe Lys Glu Lys Ser Glu Lys Pro Leu Glu Asp Leu Thr Gly Gly
        115                 120                 125
Tyr Arg Tyr Pro Arg Ala Leu Glu Glu Val Glu Lys Leu Lys Thr
    130                 135                 140
Gln Val Glu Gln Glu Val Glu His Leu Lys Ile Gln Val Met Arg Leu
145                 150                 155                 160
```

-continued

```
Arg Ala Glu Lys Ala Asp Leu Leu Gly Ile Val Ser Glu Leu Gln Leu
                165                 170                 175

Lys Leu Asn Ser Gly Gly Ser Ser Glu Asp Ser Phe Val Glu Ile Arg
            180                 185                 190

Met Thr Glu Gly Glu Thr Glu Gly Ala Met Lys Glu Met Lys Asn Cys
        195                 200                 205

Pro Thr Pro Thr Arg Thr Asp Pro Ile Ser Leu Ser Asn Cys Thr Glu
    210                 215                 220

Asp Ala Arg Ser Cys Ala Glu Phe Glu Glu Leu Thr Val Ser Gln Leu
225                 230                 235                 240

Leu Leu Cys Leu Arg Glu Gly Asn Gln Lys Val Glu Arg Leu Glu Val
                245                 250                 255

Ala Leu Arg Glu Ala Lys Glu Arg Ile Ser Asp Phe Glu Lys Lys Ala
            260                 265                 270

Asn Gly His Ser Ser Thr Glu Lys Gln Thr Ala Arg Arg Ala Asp Arg
        275                 280                 285

Glu Lys Glu Asp Lys Gly Gln Glu Ser Val Gly Ser Glu Val Glu Thr
    290                 295                 300

Leu Ser Ile Gln Val Thr Ser Leu Phe Lys Glu Leu Gln Glu Ala His
305                 310                 315                 320

Thr Lys Leu Ser Glu Ala Glu Leu Met Lys Lys Arg Leu Gln Glu Lys
                325                 330                 335

Cys Gln Ala Leu Glu Arg Lys Asn Ser Ala Thr Pro Ser Glu Leu Asn
            340                 345                 350

Glu Lys Gln Glu Leu Val Tyr Ser Asn Lys Lys Leu Glu Leu Gln Val
        355                 360                 365

Glu Ser Met Arg Ser Glu Ile Lys Met Glu Gln Ala Lys Thr Glu Glu
    370                 375                 380

Glu Lys Ser Arg Leu Ala Thr Leu Gln Ala Thr His Asn Lys Leu Leu
385                 390                 395                 400

Gln Glu His Asn Lys Ala Leu Lys Thr Ile Glu Glu Leu Thr Lys Gln
                405                 410                 415

Gln Ala Glu Lys Val Asp Lys Met Leu Leu Gln Glu Leu Ser Glu Lys
            420                 425                 430

Leu Glu Leu Ala Glu Gln Ala Leu Ala Ser Lys Gln Leu Gln Met Asp
        435                 440                 445

Glu Met Lys Gln Thr Leu Ala Lys Gln Glu Glu Asp Leu Glu Thr Met
    450                 455                 460

Ala Val Leu Arg Ala Gln Met Glu Val Tyr Cys Ser Asp Phe His Ala
465                 470                 475                 480

Glu Arg Ala Ala Arg Glu Lys Ile His Glu Glu Lys Glu Gln Leu Ala
                485                 490                 495

Leu Gln Leu Ala Ile Leu Leu Lys Glu Asn Asn Asp Ile Glu Glu Gly
            500                 505                 510

Gly Ser Arg Gln Ser Leu Met Glu Met Gln Cys Arg His Gly Ala Arg
        515                 520                 525

Thr Ser Asp Ser Asp Gln Gln Thr Tyr Leu Phe Gln Arg Gly Ala Glu
    530                 535                 540

Asp Arg Ser Trp Gln His Gly Gln Gln Pro Arg Ser Ile Pro Ile His
545                 550                 555                 560

Ser Cys Pro Lys Cys Gly Glu Val Leu Pro Asp Ile Asp Thr Leu Gln
                565                 570                 575

Ile His Val Met Asp Cys Ile Ile
```

<210> SEQ ID NO 78
<211> LENGTH: 108
<212> TYPE: PRT
<213> ORGANISM: Mus musculus

<400> SEQUENCE: 78

```
Leu Lys Thr Gln Val Glu Gln Glu Val Glu His Leu Lys Ile Gln Val
1               5                   10                  15

Met Arg Leu Arg Ala Glu Lys Ala Asp Leu Leu Gly Ile Val Ser Glu
            20                  25                  30

Leu Gln Leu Lys Leu Asn Ser Gly Gly Ser Ser Glu Asp Ser Phe Val
        35                  40                  45

Glu Ile Arg Met Thr Glu Gly Thr Glu Gly Ala Met Lys Glu Met
    50                  55                  60

Lys Ser Cys Pro Thr Pro Thr Arg Thr Asp Pro Ile Ser Leu Ser Asn
65                  70                  75                  80

Cys Thr Glu Asp Ala Arg Ser Cys Ala Glu Phe Glu Glu Leu Thr Val
                85                  90                  95

Ser Gln Leu Leu Leu Cys Leu Arg Glu Gly Asn Gln
            100                 105
```

<210> SEQ ID NO 79
<211> LENGTH: 62
<212> TYPE: PRT
<213> ORGANISM: Mus musculus

<400> SEQUENCE: 79

```
His Leu Lys Ile Gln Val Met Arg Leu Arg Ala Glu Lys Ala Asp Leu
1               5                   10                  15

Leu Gly Ile Val Ser Glu Leu Gln Leu Lys Leu Asn Ser Gly Gly Ser
            20                  25                  30

Ser Glu Asp Ser Phe Val Glu Ile Arg Met Thr Glu Gly Glu Thr Glu
        35                  40                  45

Gly Ala Met Lys Glu Met Lys Asn Cys Pro Thr Pro Thr Arg
    50                  55                  60
```

<210> SEQ ID NO 80
<211> LENGTH: 62
<212> TYPE: PRT
<213> ORGANISM: Mus musculus

<400> SEQUENCE: 80

```
His Leu Lys Ile Gln Val Met Arg Leu Arg Ala Glu Lys Ala Asp Leu
1               5                   10                  15

Leu Gly Ile Val Ser Glu Leu Gln Leu Lys Leu Asn Ser Gly Gly Ser
            20                  25                  30

Ser Glu Asp Ser Phe Val Glu Ile Arg Met Thr Glu Gly Glu Thr Glu
        35                  40                  45

Gly Ala Met Lys Glu Met Lys Asn Cys Pro Ala Pro Thr Arg
    50                  55                  60
```

<210> SEQ ID NO 81
<211> LENGTH: 62
<212> TYPE: PRT
<213> ORGANISM: Mus musculus

<400> SEQUENCE: 81

His Leu Lys Ile Gln Val Met Arg Leu Arg Ala Glu Lys Ala Asp Leu
1               5                   10                  15

Leu Gly Ile Val Ser Glu Leu Arg Leu Lys Leu Asn Ser Gly Gly Ser
            20                  25                  30

Ser Glu Asp Ser Phe Val Glu Ile Arg Met Thr Glu Gly Glu Thr Glu
            35                  40                  45

Gly Ala Met Lys Glu Met Lys Asn Cys Pro Thr Pro Thr Arg
        50                  55                  60

<210> SEQ ID NO 82
<211> LENGTH: 102
<212> TYPE: PRT
<213> ORGANISM: Mus musculus

<400> SEQUENCE: 82

Met Leu Ser Arg Leu Gln Glu Leu Arg Lys Glu Glu Thr Leu Leu
1               5                   10                  15

Arg Leu Lys Ala Ala Leu His Asp Gln Leu Asn Arg Leu Lys Val Glu
            20                  25                  30

Glu Leu Ala Leu Gln Ser Met Ile Asn Ser Arg Gly Arg Thr Glu Thr
            35                  40                  45

Leu Ser Ser Gln Pro Ala Pro Glu Gln Leu Cys Asp Met Ser Leu His
        50                  55                  60

Val Asp Asn Glu Val Thr Ile Asn Gln Thr Thr Leu Lys Leu Ser Thr
65                  70                  75                  80

Arg Ser Pro Met Glu Glu Glu Glu Glu Glu Glu Glu Glu Glu Glu Glu
                85                  90                  95

Glu Glu Glu Ser Asp Ser
            100

<210> SEQ ID NO 83
<211> LENGTH: 56
<212> TYPE: PRT
<213> ORGANISM: Mus musculus

<400> SEQUENCE: 83

Arg Cys Arg Gln Lys Arg Lys Leu Trp Val Ser Ser Leu Glu Lys Lys
1               5                   10                  15

Ala Glu Glu Leu Thr Ser Gln Asn Ile Gln Leu Ser Asn Glu Val Thr
            20                  25                  30

Leu Leu Arg Asn Glu Val Ala Gln Leu Lys Gln Leu Leu Leu Ala His
            35                  40                  45

Lys Asp Cys Pro Val Thr Ala Gln
        50                  55

<210> SEQ ID NO 84
<211> LENGTH: 79
<212> TYPE: PRT
<213> ORGANISM: Mus musculus

<400> SEQUENCE: 84

Arg Lys Trp Lys Gly Thr Leu Ser Arg Leu Gln Glu Leu Arg Lys Glu
1               5                   10                  15

Val Glu Thr Pro Leu Arg Leu Lys Ala Ala Leu His Asp Gln Leu Asn
            20                  25                  30

Arg Leu Lys Val Glu Glu Leu Ala Leu Gln Ser Met Ile Asn Ser Arg
            35                  40                  45

Gly Arg Thr Glu Thr Leu Ser Ser Gln Pro Ala Pro Glu Gln Leu Cys

```
                    50                  55                  60
Asp Met Ser Leu His Val Asp Asn Glu Val Thr Ile Asn Gln Thr
 65                  70                  75
```

<210> SEQ ID NO 85
<211> LENGTH: 413
<212> TYPE: PRT
<213> ORGANISM: Mus musculus

<400> SEQUENCE: 85

```
Met Gly Asp Asp Arg Pro Phe Val Cys Ser Ala Pro Cys Gly Gln
 1               5                  10                  15

Arg Phe Thr Asn Glu Asp His Leu Ala Val His Lys His Lys His Glu
                20                  25                  30

Met Thr Leu Lys Phe Gly Pro Ala Arg Thr Asp Ser Val Ile Ile Ala
             35                  40                  45

Asp Gln Thr Pro Thr Pro Thr Arg Phe Leu Lys Asn Cys Glu Glu Val
         50                  55                  60

Gly Leu Phe Asn Glu Leu Ala Ser Ser Phe Glu His Glu Phe Lys Lys
 65                  70                  75                  80

Ala Ser Asp Asp Glu Lys Lys Gly Ala Ala Gly Pro Leu Asp Met
                85                  90                  95

Ser Leu Pro Ser Thr Pro Asp Ile Lys Ile Lys Glu Glu Pro Val
            100                 105                 110

Glu Val Asp Ser Ser Pro Pro Asp Ser Pro Ala Ser Ser Pro Cys Ser
            115                 120                 125

Pro Pro Leu Lys Glu Lys Glu Val Thr Thr Lys Pro Val Val Ile Ser
        130                 135                 140

Thr Pro Thr Pro Thr Ile Val Arg Pro Gly Ser Leu Pro Leu His Leu
145                 150                 155                 160

Gly Tyr Asp Pro Leu His Pro Thr Leu Pro Ser Pro Thr Ser Val Ile
                165                 170                 175

Thr Gln Ala Pro Pro Ser Asn Arg Gln Ile Gly Ser Pro Thr Gly Ser
            180                 185                 190

Leu Pro Leu Val Met His Leu Ala Asn Gly Gln Thr Met Pro Met Leu
        195                 200                 205

Pro Gly Pro Pro Val Gln Met Pro Ser Val Ile Ser Leu Ala Arg Pro
    210                 215                 220

Val Ser Met Val Pro Asn Ile Pro Gly Ile Pro Gly Pro Pro Val Asn
225                 230                 235                 240

Asn Ser Gly Ser Ile Ser Pro Ser Gly His Pro Met Pro Ser Glu Ala
                245                 250                 255

Lys Met Arg Leu Lys Ala Thr Leu Thr His Gln Val Ser Ser Ile Asn
            260                 265                 270

Gly Gly Cys Gly Met Val Val Gly Thr Ala Ser Thr Met Val Thr Ala
        275                 280                 285

Arg Pro Glu Gln Asn Gln Ile Leu Ile Gln His Pro Asp Ala Pro Ser
    290                 295                 300

Pro Ala Gln Pro Gln Val Ser Pro Ala Gln Pro Thr Pro Ser Thr Gly
305                 310                 315                 320

Gly Arg Arg Arg Arg Thr Val Asp Glu Asp Pro Asp Glu Arg Arg Gln
                325                 330                 335

Arg Phe Leu Glu Arg Asn Arg Ala Ala Ala Ser Arg Cys Arg Gln Lys
            340                 345                 350
```

```
Arg Lys Leu Trp Val Ser Ser Leu Glu Lys Lys Ala Glu Glu Leu Thr
            355                 360                 365

Ser Gln Asn Ile Gln Leu Ser Asn Glu Val Thr Leu Leu Arg Asn Glu
        370                 375                 380

Val Ala Gln Leu Lys Gln Leu Leu Ala His Lys Asp Cys Pro Val
385                 390                 395                 400

Thr Ala Leu Gln Lys Lys Thr Gln Gly Tyr Leu Gly Lys
                405                 410

<210> SEQ ID NO 86
<211> LENGTH: 58
<212> TYPE: PRT
<213> ORGANISM: Mus musculus

<400> SEQUENCE: 86

Arg Ala Ala Ala Ser Arg Cys Arg Gln Lys Arg Lys Leu Trp Val Ser
1               5                   10                  15

Ser Leu Glu Lys Lys Ala Glu Glu Leu Thr Ser Gln Asn Ile Gln Leu
            20                  25                  30

Ser Asn Lys Val Thr Leu Leu Arg Asn Glu Val Ala Gln Leu Lys Gln
        35                  40                  45

Leu Leu Leu Ala His Lys Asp Cys Pro Gly
    50                  55

<210> SEQ ID NO 87
<211> LENGTH: 1031
<212> TYPE: PRT
<213> ORGANISM: Mus musculus

<400> SEQUENCE: 87

Met Thr Asn Pro Lys Gly Lys Arg Arg Gly Thr Gln Ser Met Phe Ser
1               5                   10                  15

Arg Pro Phe Arg Lys His Gly Val Val Ser Leu Ala Thr Tyr Met Arg
            20                  25                  30

Ile Tyr Lys Lys Arg Asp Ile Val Asp Ile Lys Gly Met Gly Thr Val
        35                  40                  45

Gln Lys Gly Met Pro Cys Lys Cys Tyr His Gly Lys Thr Gly Arg Val
    50                  55                  60

Tyr Asn Val Thr Gln His Ala Met Gly Ile Ile Val Asn Lys Gln Val
65                  70                  75                  80

Lys Gly Lys Ile Leu Ala Lys Arg Ile Asn Val Gln Ile Glu His Ile
                85                  90                  95

Lys His Ser Lys Ser Arg Asp Gly Phe Leu Lys Gln Gly Glu Ala Ala
            100                 105                 110

His Phe Glu Tyr Leu Leu Tyr Pro Leu His Ser Ala Ser Ile Thr Gly
        115                 120                 125

Leu Ala Thr Cys Ile Arg Lys Pro Leu Ile Ala Thr Cys Ser Leu Asp
    130                 135                 140

Arg Ser Val Arg Ile Trp Asn Tyr Glu Ser Asn Ser Ser Cys Cys Lys
145                 150                 155                 160

Ala Leu Arg Glu Asp Leu Trp Leu Leu Leu Phe His Ile Thr Ala
                165                 170                 175

Pro Ala Thr Leu Ser Ser Pro Val Ile Phe Phe Cys Thr Leu Glu
            180                 185                 190

Leu Tyr Lys Glu Tyr Gln Glu Glu Ala Tyr Thr Val Ser Leu His Pro
        195                 200                 205
```

-continued

```
Ser Gly His Tyr Ile Val Val Gly Phe Ala Asp Lys Leu Arg Leu Met
    210                 215                 220

Asn Leu Leu Ile Asp Asp Ile Arg Ser Phe Lys Glu Tyr Ser Val Arg
225                 230                 235                 240

Gly Cys Lys Glu Cys Ala Phe Ser Asn Gly Gly His Leu Phe Ala Ala
                    245                 250                 255

Val Asn Gly Asn Val Ile His Ile Phe Thr Thr Thr Asn Leu Glu Asn
                260                 265                 270

Ile Asn Asn Leu Lys Gly His Thr Gly Lys Arg Glu Thr Glu Cys Val
            275                 280                 285

Leu Lys Val Cys Ser Tyr Asn Ser Val Thr Ile Ser Pro Asp Gly Lys
    290                 295                 300

Val Ile Phe Ala Val Gly Ser Asp Gln Thr Leu Lys Glu Ile Ala Asp
305                 310                 315                 320

Ser Leu Ile Leu Arg Glu Ile Pro Ala Phe Asp Val Val Tyr Thr Ala
                    325                 330                 335

Ile Thr Ile Ser His Ser Gly Arg Met Ile Phe Val Gly Thr Ser Val
                340                 345                 350

Gly Thr Ile Arg Ala Met Lys Tyr Pro Leu Pro Leu Gln Arg Glu Phe
            355                 360                 365

Asn Glu Tyr Gln Ala His Ala Gly Pro Val Thr Lys Ile Leu Leu Thr
    370                 375                 380

Phe Asp Asp Gln Phe Leu Leu Thr Val Ser Glu Asp Gly Cys Leu Phe
385                 390                 395                 400

Thr Trp Lys Val Phe Asp Lys Glu Gly Arg Gly Ile Lys Arg Glu Arg
                    405                 410                 415

Glu Val Gly Phe Ala Glu Glu Val Leu Val Thr Lys Thr Asp Met Glu
                420                 425                 430

Glu Lys Ile Leu His Arg Asn Leu Ala Thr Glu Phe Arg Arg Pro Met
            435                 440                 445

Ser Lys His Leu Glu Cys Pro Thr Ser Glu Thr Gly Pro Leu Thr Thr
    450                 455                 460

Ile Asn Ile Ser Pro Val Gln Pro Arg Pro Trp Gly His Val Leu Thr
465                 470                 475                 480

Cys Arg Thr Pro Val Ser Thr Asp Ser Ala Val Ala Ser Thr Arg Gly
                    485                 490                 495

Ser Val Asp Ser Ala Val Lys Pro Asp Arg Ser Thr Pro Thr Gln Glu
                500                 505                 510

Val Arg Ile Pro Pro Lys Pro Ala Ser Gly Val His Thr Arg Cys Gln
            515                 520                 525

Leu Gly Val Gln Lys Gln Met Glu His Val Ser Val Val Met Glu Val
    530                 535                 540

Arg Glu Thr Asn Arg Gln Arg Gln Gly Gly Ala Arg Asn Val Ile
545                 550                 555                 560

Lys Ala Gln Ile Met Leu Glu Leu Lys Thr Arg Val Glu Glu Leu Lys
                    565                 570                 575

Met Glu Asn Glu Tyr Gln Leu Arg Leu Lys Asp Met Asn Tyr Ser Glu
                580                 585                 590

Lys Ile Lys Glu Leu Thr Asp Lys Phe Ile Gln Glu Met Glu Ser Leu
            595                 600                 605

Lys Thr Lys Asn Gln Val Leu Lys Thr Glu Lys Glu Lys Gln Asp Ile
    610                 615                 620

Ser His Arg Glu His Leu Glu Asp Leu Ile Glu Arg Gln Ser Arg Glu
```

-continued

```
                625                 630                 635                 640
Leu Gln Asp Leu Glu Cys Cys Asn Asn Gln Lys Leu Leu Leu Glu Tyr
                    645                 650                 655
Glu Lys Tyr Gln Glu Leu Gln Leu Lys Ser Gln Arg Met Gln Glu Glu
                    660                 665                 670
Tyr Glu Lys Gln Leu Arg Asp Asn Asp Glu Thr Lys Ser Gln Ala Leu
                    675                 680                 685
Glu Glu Leu Thr Glu Phe Tyr Glu Ala Lys Leu Gln Glu Lys Thr Gly
                    690                 695                 700
Leu Leu Glu Glu Ala Leu Ser Thr Ala Ala Ser Pro Pro Leu Pro Ser
705                 710                 715                 720
Ala His Val Leu Ser Pro Phe Pro Thr Leu Ser Gln Ala Gln Glu Asp
                    725                 730                 735
Val Arg Gln Gln Leu Arg Glu Phe Glu Glu Thr Lys Lys Gln Ile Glu
                    740                 745                 750
Glu Asp Glu Asp Arg Glu Ile Gln Asp Ile Lys Thr Lys Tyr Glu Arg
                    755                 760                 765
Lys Leu Arg Asp Glu Lys Glu Ser Asn Leu Arg Leu Lys Gly Glu Thr
                    770                 775                 780
Gly Ile Met Arg Lys Lys Phe Ser Ser Leu Gln Lys Glu Ile Glu Glu
785                 790                 795                 800
Arg Thr Asn Asp Ile Glu Leu Leu Lys Thr Glu Gln Val Lys Leu Gln
                    805                 810                 815
Gly Val Ile Arg Ser Leu Glu Lys Asp Ile Gln Gly Leu Lys Arg Glu
                    820                 825                 830
Ile Gln Glu Arg Asp Glu Thr Ile Gln Asp Lys Glu Lys Arg Ile Tyr
                    835                 840                 845
Asp Leu Lys Lys Lys Asn Gln Glu Leu Glu Lys Phe Lys Phe Val Leu
                    850                 855                 860
Asp Tyr Lys Ile Lys Glu Leu Lys Lys Gln Ile Glu Pro Arg Glu Asn
865                 870                 875                 880
Glu Ile Lys Val Met Lys Glu Gln Ile Gln Glu Asn Pro Val Asn His
                    885                 890                 895
Trp Leu Arg Ser Arg Glu Arg Glu Cys Val Thr Gln Pro Arg His Leu
                    900                 905                 910
Arg Leu Pro Ala Pro Gln Asn Lys Leu Asp Gly Asn Leu Ala Cys Gly
                    915                 920                 925
Pro Val Arg Gly Arg Leu Cys His Ser Asp Ala Thr Ser Gly Ala Leu
                    930                 935                 940
Asn Val Gln Gly Ile Leu Cys Leu Phe His Leu Pro Phe Pro Cys Asp
945                 950                 955                 960
Arg Thr Pro Ser Phe Phe Pro Gly Glu Ala Cys Leu Leu Val Phe Ser
                    965                 970                 975
Leu Leu Ile Asp Val Leu Cys Arg Pro Thr Ser Asp Val Pro Val Ala
                    980                 985                 990
Ala Gly Asp Phe Leu Pro Cys Gly  Gly Pro Leu His Leu  Pro Pro Glu
                    995                 1000                1005
Leu His  His Leu Thr Val Ile  Arg Thr Asn Ala Ser  Pro Gln Lys
        1010                1015                1020
Cys Tyr  Pro Pro Thr Ser  Pro  Leu
        1025                1030
```

<210> SEQ ID NO 88

```
<211> LENGTH: 70
<212> TYPE: PRT
<213> ORGANISM: Mus musculus

<400> SEQUENCE: 88

Lys Lys Phe Ser Ser Leu Gln Lys Glu Ile Glu Glu Arg Thr Asn Asp
1               5                   10                  15

Ile Glu Leu Leu Lys Ser Glu Arg Met Lys Leu Gln Gly Ile Ile Arg
            20                  25                  30

Ser Leu Glu Lys Asp Ile Gln Gly Leu Lys Arg Glu Ile Gln Glu Arg
        35                  40                  45

Asp Glu Thr Ile Gln Asp Met Glu Lys Leu Asp Tyr Lys Asp Asp Tyr
    50                  55                  60

Asn Ser Asn Leu Glu Ile
65                  70

<210> SEQ ID NO 89
<211> LENGTH: 56
<212> TYPE: PRT
<213> ORGANISM: Mus musculus

<400> SEQUENCE: 89

Lys Lys Phe Ser Ser Leu Gln Lys Glu Ile Glu Glu Arg Thr Asn Asp
1               5                   10                  15

Ile Glu Leu Leu Lys Ser Glu Arg Met Lys Leu Gln Gly Ile Ile Arg
            20                  25                  30

Ser Leu Glu Lys Asp Ile Gln Gly Leu Lys Arg Glu Ile Gln Glu Arg
        35                  40                  45

Asp Glu Thr Ile Gln Asp Met Glu
    50                  55

<210> SEQ ID NO 90
<211> LENGTH: 217
<212> TYPE: PRT
<213> ORGANISM: Mus musculus

<400> SEQUENCE: 90

Met Glu Val Glu Asn Glu Ala His Cys Cys Pro Gly Ser Ser Ser Gly
1               5                   10                  15

Gly Ser Arg Glu Tyr Lys Val Val Met Leu Gly Ala Gly Gly Val Gly
            20                  25                  30

Lys Ser Ala Val Thr Met Gln Phe Ile Ser His Gln Phe Pro Asp Tyr
        35                  40                  45

His Asp Pro Thr Ile Glu Asp Ala Tyr Lys Thr Gln Val Arg Ile Asp
    50                  55                  60

Asn Glu Pro Ala Tyr Leu Asp Ile Leu Asp Thr Ala Gly Gln Ala Glu
65                  70                  75                  80

Phe Thr Ala Met Arg Glu Gln Tyr Met Arg Gly Gly Glu Gly Phe Ile
                85                  90                  95

Ile Cys Tyr Ser Val Thr Asp Arg Gln Ser Phe Gln Glu Ala Ala Lys
            100                 105                 110

Phe Lys Glu Leu Ile Phe Gln Val Arg His Thr Tyr Glu Ile Pro Leu
        115                 120                 125

Val Leu Val Gly Asn Lys Ile Asp Leu Glu Gln Phe Arg Gln Val Ser
    130                 135                 140

Thr Glu Glu Gly Met Asn Leu Ala Arg Asp Tyr Asn Cys Ala Phe Phe
145                 150                 155                 160
```

```
Glu Thr Ser Ala Ala Leu Arg Phe Gly Ile Asp Asp Ala Phe Gln Gly
                165                 170                 175

Leu Val Arg Glu Ile Arg Arg Lys Glu Ser Met Leu Ser Leu Val Glu
            180                 185                 190

Arg Lys Leu Lys Arg Lys Asp Ser Leu Trp Lys Lys Ile Lys Ala Ser
                195                 200                 205

Leu Lys Lys Lys Arg Glu Asn Met Leu
    210                 215

<210> SEQ ID NO 91
<211> LENGTH: 50
<212> TYPE: PRT
<213> ORGANISM: Mus musculus

<400> SEQUENCE: 91

Ala Ala Leu Arg Phe Gly Ile Asp Asp Ala Leu Gln Gly Leu Val Arg
1               5                   10                  15

Glu Ile Arg Arg Lys Glu Ser Met Leu Pro Leu Val Glu Arg Lys Leu
            20                  25                  30

Lys Arg Lys Asp Ser Leu Trp Lys Lys Ile Lys Ala Ser Leu Lys Lys
        35                  40                  45

Lys Arg
    50

<210> SEQ ID NO 92
<211> LENGTH: 140
<212> TYPE: PRT
<213> ORGANISM: Mus musculus

<400> SEQUENCE: 92

Gly Ala Thr Val Ile Thr Asn Leu Leu Ser Ala Ile Pro Tyr Ile Gly
1               5                   10                  15

Thr Thr Leu Val Glu Trp Ile Trp Gly Gly Phe Ser Val Asp Lys Ala
            20                  25                  30

Thr Leu Thr Arg Phe Phe Ala Phe His Phe Ile Leu Pro Phe Ile Ile
        35                  40                  45

Ala Ala Leu Ala Ile Val His Leu Leu Phe Leu His Glu Thr Gly Ser
    50                  55                  60

Asn Asn Pro Thr Gly Leu Asn Ser Asp Ala Asp Lys Ile Pro Phe His
65                  70                  75                  80

Pro Tyr Tyr Thr Ile Lys Asp Ile Leu Gly Ile Leu Ile Met Phe Leu
                85                  90                  95

Ile Leu Met Thr Leu Val Leu Phe Phe Pro Asp Met Leu Gly Asp Pro
            100                 105                 110

Asp Asn Tyr Met Pro Ala Asn Pro Leu Asn Thr Pro Pro His Ile Lys
        115                 120                 125

Pro Glu Trp Tyr Phe Leu Phe Ala Tyr Ala Ile Leu
    130                 135                 140

<210> SEQ ID NO 93
<211> LENGTH: 41
<212> TYPE: PRT
<213> ORGANISM: Mus musculus

<400> SEQUENCE: 93

Ser Asp Ala Asp Lys Ile Pro Phe His Pro Tyr Tyr Thr Ile Lys Asn
1               5                   10                  15

Ile Leu Gly Ile Leu Ile Ile Phe Leu Ile Leu Ile Thr Leu Val Leu
```

```
                    20                  25                  30

Phe Phe Pro Asp Ile Leu Gly Asp Pro
        35                  40

<210> SEQ ID NO 94
<211> LENGTH: 311
<212> TYPE: PRT
<213> ORGANISM: Mus musculus

<400> SEQUENCE: 94

Met Lys Ala Leu Trp Ala Val Leu Leu Val Thr Leu Leu Thr Gly Cys
1               5                   10                  15

Leu Ala Glu Gly Glu Pro Glu Val Thr Asp Gln Leu Glu Trp Gln Ser
            20                  25                  30

Asn Gln Pro Trp Glu Gln Ala Leu Asn Arg Phe Trp Asp Tyr Leu Arg
        35                  40                  45

Trp Val Gln Thr Leu Ser Asp Gln Val Gln Glu Glu Leu Gln Ser Ser
    50                  55                  60

Gln Val Thr Gln Glu Leu Thr Ala Leu Met Glu Asp Thr Met Thr Glu
65                  70                  75                  80

Val Lys Ala Tyr Lys Lys Glu Leu Glu Glu Gln Leu Gly Pro Val Ala
                85                  90                  95

Glu Glu Thr Arg Ala Arg Leu Gly Lys Glu Val Gln Ala Ala Gln Ala
            100                 105                 110

Arg Leu Gly Ala Asp Met Glu Asp Leu Arg Asn Arg Leu Gly Gln Tyr
        115                 120                 125

Arg Asn Glu Val His Thr Met Leu Gly Gln Ser Thr Glu Glu Ile Arg
    130                 135                 140

Ala Arg Leu Ser Thr His Leu Arg Lys Met Arg Lys Arg Leu Met Arg
145                 150                 155                 160

Asp Ala Asp Asp Leu Gln Lys Arg Leu Ala Val Tyr Lys Ala Gly Ala
                165                 170                 175

Arg Glu Gly Ala Glu Arg Gly Val Ser Ala Ile Arg Glu Arg Leu Gly
            180                 185                 190

Pro Leu Val Glu Gln Gly Arg Gln Arg Thr Ala Asn Leu Gly Ala Gly
        195                 200                 205

Ala Ala Gln Pro Leu Arg Asp Arg Ala Gln Ala Phe Gly Asp Arg Ile
    210                 215                 220

Arg Gly Arg Leu Glu Glu Val Gly Asn Gln Ala Arg Asp Arg Leu Glu
225                 230                 235                 240

Glu Val Arg Glu His Met Glu Glu Val Arg Ser Lys Met Glu Glu Gln
                245                 250                 255

Thr Gln Gln Ile Arg Leu Gln Ala Glu Ile Phe Gln Ala Arg Leu Lys
            260                 265                 270

Gly Trp Phe Glu Pro Ile Val Glu Asp Met His Arg Gln Trp Ala Asn
        275                 280                 285

Leu Met Glu Lys Ile Gln Ala Ser Val Ala Thr Asn Pro Ile Ile Thr
    290                 295                 300

Pro Val Ala Gln Glu Asn Gln
305                 310

<210> SEQ ID NO 95
<211> LENGTH: 31
<212> TYPE: PRT
<213> ORGANISM: Mus musculus
```

```
<400> SEQUENCE: 95

Thr Glu Val Lys Ala Tyr Lys Lys Glu Leu Glu Glu Gln Leu Gly Pro
 1               5                  10                  15

Val Ala Glu Glu Thr Arg Ala Arg Leu Gly Lys Glu Glu Gln Gly
            20                  25                  30

<210> SEQ ID NO 96
<211> LENGTH: 695
<212> TYPE: PRT
<213> ORGANISM: Mus musculus

<400> SEQUENCE: 96

Met Leu Pro Ser Leu Ala Leu Leu Leu Ala Ala Trp Thr Val Arg
 1               5                  10                  15

Ala Leu Glu Val Pro Thr Asp Gly Asn Ala Gly Leu Leu Ala Glu Pro
            20                  25                  30

Gln Ile Ala Met Phe Cys Gly Lys Leu Asn Met His Met Asn Val Gln
        35                  40                  45

Asn Gly Lys Trp Glu Ser Asp Pro Ser Gly Thr Lys Thr Cys Ile Gly
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Thr His Ile Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Ser Val Asp Ser Ala Asp Ala Glu Glu Asp Asp Ser Asp Val
        195                 200                 205

Trp Trp Val Gly Ala Asp Thr Asp Tyr Ala Asp Gly Gly Glu Asp Lys
    210                 215                 220

Val Val Glu Val Ala Glu Glu Glu Val Ala Asp Val Glu Glu Glu
225                 230                 235                 240

Glu Ala Asp Asp Asp Glu Asp Val Glu Asp Gly Asp Glu Val Glu Glu
                245                 250                 255

Glu Ala Glu Glu Pro Tyr Glu Glu Ala Thr Glu Arg Thr Thr Ser Thr
            260                 265                 270

Ala Thr Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335
```

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Leu Val Glu Thr His Met Ala
    370                 375                 380

Arg Val Glu Ala Met Leu Asn Asp Arg Arg Leu Asp Leu Glu Asn
385                 390                 395                 400

Tyr Ile Ile Ala Leu Gln Ala Val Pro Pro Arg Pro His His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Thr Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Pro Phe Gly Val Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Gly His Asp Ser Gly Phe Glu Val
        595                 600                 605

Arg His Gln Lys Leu Val Phe Phe Ala Glu Asp Val Gly Ser Asn Lys
    610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
    690                 695

<210> SEQ ID NO 97
<211> LENGTH: 68
<212> TYPE: PRT
<213> ORGANISM: Mus musculus

<400> SEQUENCE: 97

Ser Glu Pro Arg Ile Ser Tyr Gly Asn Asp Ala Leu Met Pro Ser Leu
1               5                   10                  15

```
Thr Glu Thr Lys Thr Thr Val Glu Leu Leu Pro Val Asn Gly Glu Phe
             20                  25                  30

Ser Leu Asp Asp Leu Gln Pro Trp His Pro Ser Gly Val Asp Ser Val
         35                  40                  45

Pro Ala Asn Thr Glu Asn Glu Val Glu Pro Val Asp Ala Arg Pro Ala
     50                  55                  60

Ala Asp Arg Gly
 65

<210> SEQ ID NO 98
<211> LENGTH: 983
<212> TYPE: PRT
<213> ORGANISM: Mus musculus

<400> SEQUENCE: 98

Met Lys Ala Gln Gln Ala Met Asp Lys Tyr Glu Gly Asp Ser Lys Ala
 1               5                  10                  15

Arg Glu Thr Arg Ser Thr Ala Ala Met Val Gly Trp Arg Ser Asp Arg
             20                  25                  30

Gly Leu Val Thr Cys Thr Arg Leu Arg Met Gln Asn Gly Ser Ser Leu
         35                  40                  45

Lys Ala Phe Arg Ser Arg Val Gly Lys Trp Gly Glu Pro Ser Ser Arg
     50                  55                  60

Ser His Lys Val Leu Lys Thr Ser Glu Thr Ser Gln Asp Ile Gln Lys
 65                  70                  75                  80

Val Ser Arg Glu Glu Ser Pro Ser Gln Leu Thr Ser Ala Val Pro Ala
                 85                  90                  95

Gln Arg Asn Cys Gln Pro Gly Ser Ala Ala Val Ile Asn Met Leu Arg
            100                 105                 110

Gly Gly Gly Gly Val Arg Ser Pro Trp Thr Asp His His Ile Arg Gln
        115                 120                 125

Arg Thr Asp His His Ile Arg Gln Pro Leu Phe Pro Ser Arg Arg Ser
    130                 135                 140

Pro Gln Glu Asn Glu Asp Asp Asp Asp Tyr Gln Met Phe Val Pro
145                 150                 155                 160

Ser Phe Ser Ser Ser Asp Leu Asn Ser Thr Arg Leu Cys Glu Glu Asn
                165                 170                 175

Ala Ser Ser Arg Pro Cys Ser Trp His Leu Gly Leu Ile Glu Pro Thr
            180                 185                 190

Glu Ile Ser Ser Ser Gly His Arg Ile Val Arg Arg Ala Ser Ser Ala
        195                 200                 205

Gly Glu Ser Asn Ala Cys Pro Pro Glu Val Arg Ile Arg Asp Cys Asp
    210                 215                 220

Asp Ser Gln Tyr Cys Pro Gly Arg Gln Leu Gln Asn Ser Pro Arg Pro
225                 230                 235                 240

Gly Gly Glu Arg Gly Met Thr Pro Tyr Gly Ser Ser Val Glu Leu Thr
                245                 250                 255

Ile Asp Asp Ile Asp His Val Tyr Asp Asn Ile Ser Phe Glu Asp Leu
            260                 265                 270

Lys Leu Met Val Ala Lys Arg Asp Glu Thr Glu Cys Ser Phe Ser Lys
        275                 280                 285

Pro Ser Arg Asp Ser Val Arg Pro Lys Ser Thr Pro Glu Leu Ala Phe
    290                 295                 300

Ser Lys Arg Gln Val Ser His Ser Thr Ser Ser Leu His Ser Arg Lys
```

```
            305                 310                 315                 320
    Glu Ala Gly Leu Gly Gly Gln Glu Ala Ser Thr Gln Ser Val His Glu
                    325                 330                 335

His Gln Glu Val Glu Glu Asn Ile Tyr Asp Thr Ile Gly Leu Pro Asp
                    340                 345                 350

Pro Pro Ser Met Asn Leu Asn His Ser Ser Leu His Gln Pro Lys Arg
                    355                 360                 365

Ser Thr Phe Leu Gly Leu Glu Ala Asp Phe Ala Cys Cys Asp Ser Leu
                370                 375                 380

Arg Pro Phe Val Ser Gln Asp Ser Leu Gln Phe Ser Glu Asp Asp Ile
    385                 390                 395                 400

Ser Tyr His Gln Gly Pro Ser Asp Thr Glu Tyr Leu Ser Leu Leu Tyr
                    405                 410                 415

Asp Ser Pro Arg Cys Asn Leu Pro Ile Ala Asp Lys Ala Leu Ser Asp
                    420                 425                 430

Lys Leu Ser Glu Glu Val Asp Glu Ile Trp Asn Asp Leu Glu Asn Tyr
                435                 440                 445

Ile Lys Lys Asn Glu Asp Lys Ser Arg Asp Arg Leu Leu Ala Ala Phe
    450                 455                 460

Pro Val Ser Lys Asp Asp Ala Pro Glu Arg Leu Tyr Val Asp Ser Thr
    465                 470                 475                 480

His Glu Leu Gly Arg Asp Thr Gly His Ala Thr Ser Met Leu Ala Leu
                    485                 490                 495

Pro Thr Ser Gln Thr Phe Leu Leu Pro Gly Lys Ser Arg Val Val Arg
                    500                 505                 510

Ala Ser Arg Ala Asn Cys Ser Leu Asp Asn Asp Ile Ile Ser Thr Glu
                    515                 520                 525

Gly Ser Phe Leu Ser Leu Asn Gln Leu Ser Leu Ala Ser Asp Gly Pro
                530                 535                 540

Pro Val Asp Asn Pro Tyr Asp Leu Ala Asn Cys Ser Leu Pro Gln Thr
    545                 550                 555                 560

Asp Pro Glu Asn Pro Asp Pro Gly Met Glu Val Thr Asp Lys Thr Lys
                    565                 570                 575

Ser Arg Val Phe Met Met Ala Arg Gln Tyr Ser Gln Lys Ile Lys Lys
                580                 585                 590

Val Asn Gln Ile Leu Lys Val Lys Ser Pro Glu Leu Glu Gln Pro Pro
                595                 600                 605

Ser Ser Gln His Arg Pro Ser His Lys Asp Leu Val Ala Ile Leu Glu
                610                 615                 620

Glu Lys Arg Gln Gly Gly Pro Ala Ile Gly Ala Arg Ile Ala Glu Tyr
    625                 630                 635                 640

Ser Gln Leu Tyr Asp Gln Ile Val Phe Arg Glu Thr Pro Leu Lys Ala
                    645                 650                 655

Gln Lys Asp Gly Trp Ala Ser Pro Gln Gly Pro Thr Leu His Arg Pro
                    660                 665                 670

Val Ser Pro Pro Gln Ala Gln Gly Ala Gly Glu Asp Trp Leu Trp His
                    675                 680                 685

Ser Pro Tyr Ser Asn Gly Glu Leu Ala Asp Phe Ser Pro Gln Thr Glu
                690                 695                 700

Gln Asp Ser Lys Ser Lys Tyr Pro Ile Thr Leu Glu Ser Thr Thr Lys
    705                 710                 715                 720

Ile Arg Pro Arg Gln Leu Ser Gly Ala Cys Ser Val Pro Ser Leu Gln
                    725                 730                 735
```

```
Val Ser Asp Pro Leu Leu Gly Ser Val Gln Gln Arg Cys Ser Val Val
            740                 745                 750

Val Ser Gln Pro His Lys Glu Asn Ser Gly Gln Ser Pro Leu Tyr Asn
            755                 760                 765

Ser Leu Gly Arg Lys Ala Ile Ser Ala Lys Pro Gln Pro Tyr Ser Arg
            770                 775                 780

Pro Gln Ser Ser Ser Ile Leu Ile Asn Lys Ser Leu Asp Ser Ile
785                 790                 795                 800

Asn Tyr Pro Ser Glu Thr Glu Thr Lys Gln Leu Leu Ser Ser Gln Lys
                    805                 810                 815

Ser Pro Arg Gly Ala Ser Gln Gln Asp Leu Pro Ser Gly Leu Ala Asn
            820                 825                 830

Ser Cys Gln Gln Asp Arg Gly Arg Ser Asp Leu Thr Leu Gln Asp
            835                 840                 845

Ser Gln Lys Val Leu Val Val Asn Arg Asn Leu Pro Leu Ser Ala Gln
            850                 855                 860

Ile Ala Thr Gln Asn Tyr Phe Cys Asn Phe Lys Asp Pro Glu Gly Asp
865                 870                 875                 880

Glu Asp Asp Tyr Val Glu Ile Lys Ser Glu Glu Asp Val Arg Leu
                    885                 890                 895

Asp Leu Ser Pro Arg Arg Gly Arg Lys Ser Asp Pro Gln Thr Pro Asp
            900                 905                 910

Pro Asp Cys Ser Asp Ser Ile Cys Ser His Ser Thr Pro Tyr Ser Leu
            915                 920                 925

Lys Glu Pro Val Ser Gly Arg Leu Gly Leu Pro Pro Tyr Leu Thr Ala
            930                 935                 940

Cys Lys Asp Ser Asp Lys Leu Asn Asp Tyr Leu Trp Arg Gly Pro Ser
945                 950                 955                 960

Pro Asn Gln Gln Asn Ile Val Gln Ser Leu Arg Glu Lys Phe Gln Cys
                    965                 970                 975

Leu Ser Ser Ser Ser Phe Ala
            980

<210> SEQ ID NO 99
<211> LENGTH: 46
<212> TYPE: PRT
<213> ORGANISM: Mus musculus

<400> SEQUENCE: 99

Phe Met Met Ala Arg Gln Tyr Ser Gln Lys Ile Lys Lys Val Asn Gln
1               5                   10                  15

Ile Leu Lys Val Lys Ser Pro Glu Leu Glu Gln Pro Ser Ser Gln
            20                  25                  30

His Arg Pro Ser His Lys Asp Leu Ala Ala Ile Leu Glu Lys
        35                  40                  45

<210> SEQ ID NO 100
<211> LENGTH: 412
<212> TYPE: PRT
<213> ORGANISM: Mus musculus

<400> SEQUENCE: 100

Met Ala Asn Val Ala Asp Thr Lys Leu Tyr Asp Ile Leu Gly Val Pro
1               5                   10                  15

Pro Gly Ala Ser Glu Asn Glu Leu Lys Lys Ala Tyr Arg Lys Leu Ala
            20                  25                  30
```

-continued

```
Lys Glu Tyr His Pro Asp Lys Asn Pro Asn Ala Gly Asp Lys Phe Lys
             35                  40                  45

Glu Ile Ser Phe Ala Tyr Glu Val Leu Ser Asn Pro Glu Lys Arg Glu
         50                  55                  60

Leu Tyr Asp Arg Tyr Gly Glu Gln Gly Leu Arg Glu Gly Ser Gly Gly
 65                  70                  75                  80

Gly Gly Gly Met Asp Asp Ile Phe Ser His Ile Phe Gly Gly Gly Leu
                 85                  90                  95

Phe Gly Phe Met Gly Asn Gln Ser Arg Ser Arg Asn Gly Arg Arg Arg
                100                 105                 110

Gly Glu Asp Met Met His Pro Leu Lys Val Ser Leu Glu Asp Leu Tyr
                115                 120                 125

Asn Gly Lys Thr Thr Lys Leu Gln Leu Ser Lys Asn Val Leu Cys Ser
            130                 135                 140

Ala Cys Ser Gly Gln Gly Gly Lys Ser Gly Ala Val Gln Lys Cys Ser
145                 150                 155                 160

Ala Cys Arg Gly Arg Gly Val Arg Ile Met Ile Arg Gln Leu Ala Pro
                165                 170                 175

Gly Met Val Gln Gln Met Gln Ser Val Cys Ser Asp Cys Asn Gly Glu
                180                 185                 190

Gly Glu Val Ile Asn Glu Lys Asp Arg Cys Lys Lys Cys Glu Gly Lys
            195                 200                 205

Lys Val Ile Lys Glu Val Lys Ile Leu Glu Val His Val Asp Lys Gly
            210                 215                 220

Met Lys His Gly Gln Arg Ile Thr Phe Thr Gly Glu Ala Asp Gln Ala
225                 230                 235                 240

Pro Gly Val Glu Pro Gly Asp Ile Val Leu Leu Gln Glu Lys Glu
                245                 250                 255

His Glu Val Phe Gln Arg Asp Gly Asn Asp Leu His Met Thr Tyr Lys
                260                 265                 270

Ile Gly Leu Val Glu Ala Leu Cys Gly Phe Gln Phe Thr Phe Lys His
            275                 280                 285

Leu Asp Ala Arg Gln Ile Val Val Lys Tyr Pro Pro Gly Lys Val Ile
        290                 295                 300

Glu Pro Gly Cys Val Arg Val Val Arg Gly Glu Gly Met Pro Gln Tyr
305                 310                 315                 320

Arg Asn Pro Phe Glu Lys Gly Asp Leu Tyr Ile Lys Phe Asp Val Gln
                325                 330                 335

Phe Pro Glu Asn Asn Trp Ile Asn Pro Asp Lys Leu Ser Glu Leu Glu
                340                 345                 350

Asp Leu Leu Pro Ser Arg Pro Glu Val Pro Asn Val Ile Gly Glu Thr
            355                 360                 365

Glu Glu Val Glu Leu Gln Glu Phe Asp Ser Thr Arg Gly Ser Gly Gly
            370                 375                 380

Gly Gln Arg Arg Glu Ala Tyr Asn Asp Ser Ser Asp Glu Glu Ser Ser
385                 390                 395                 400

Ser His His Gly Pro Gly Val Gln Cys Ala His Gln
                405                 410
```

<210> SEQ ID NO 101
<211> LENGTH: 25
<212> TYPE: PRT
<213> ORGANISM: Mus musculus

<400> SEQUENCE: 101

Leu Ser Asn Pro Glu Lys Arg Glu Leu Tyr Asp Arg Tyr Gly Glu Gln
1               5                   10                  15

Gly Leu Arg Glu Gly Ser Gly Gly Gly
            20                  25

<210> SEQ ID NO 102
<211> LENGTH: 29
<212> TYPE: PRT
<213> ORGANISM: Mus musculus

<400> SEQUENCE: 102

Ala His Ser Phe Ser Val Phe Arg Leu Pro Ser Trp Trp Ile Val Gly
1               5                   10                  15

Trp Trp Ser Lys Gly Gly Val Gly Ser Asp Leu Glu Met
            20                  25

<210> SEQ ID NO 103
<211> LENGTH: 35
<212> TYPE: PRT
<213> ORGANISM: Mus musculus

<400> SEQUENCE: 103

Pro Asp Ile Lys His Pro Gly Asn Leu Glu His Tyr Ile Lys Arg Val
1               5                   10                  15

Asn Leu Arg Ile Ile Ala Ile Glu Glu Gly Glu Lys Ser Gln Leu Lys
            20                  25                  30

Gly Pro Lys
        35

<210> SEQ ID NO 104
<211> LENGTH: 573
<212> TYPE: DNA
<213> ORGANISM: Mus musculus

<400> SEQUENCE: 104
atgccattga ggcatctagc agacagattg gggcatctgg cagacagact gaggcatcta     60
acagacagat tgaggcatct agcagacaga ctgaggcatc taacagacag actgaggcat    120
ctagcagaca gactgaagca tctagcagac agactgaaac atctaacaga cagattgggg    180
catctaacag acagatcatg gcatctaaca gacagattgg ggcatctaac agacagattg    240
aggcatctaa cagacagatt ggggcatcta acagacagac agaggtatct agcagacaga    300
ttgaggcatc taacagacag attggggcat ctaacagaca aactgaggca tctaacagac    360
agattggggc atctaacaga cagactgagg catctaacag acagattggg gcatctaaca    420
gacagactga tgcatctaac agacagactg atgcatctaa cagacagact gaggcatcta    480
gcagacagac agaggcatct agcagacaga cagaggcatc tagcagacag actgaggcat    540
ctagcagaca aattgaggca tcagctgcag ctg                                 573

<210> SEQ ID NO 105
<211> LENGTH: 213
<212> TYPE: DNA
<213> ORGANISM: Mus musculus

<400> SEQUENCE: 105
attgaggcat ctaacagaca gattggggca tctaacagac aaactgaggc atctaacaga     60
cagattgggc atctaacaga cagactgagg catctaacag acagattggg gcatctaaca    120

```
gacagactga tgcatctaac agacagactg atgcatctaa cagacagact gaggcatcta    180
gcagacagac agaggcatct agcagacaga ctg                                 213

<210> SEQ ID NO 106
<211> LENGTH: 165
<212> TYPE: DNA
<213> ORGANISM: Mus musculus

<400> SEQUENCE: 106
gacaaactga ggcatctaac agacagattg gggcatctaa cagacagact gaggcatcta     60
acagacagat tggggcatct aacagacaga ctgatgcatc taacagacag actgatgcat    120
ctaacagaca gactgaggca tctagcagac agacagaggc acgac                    165

<210> SEQ ID NO 107
<211> LENGTH: 135
<212> TYPE: DNA
<213> ORGANISM: Mus musculus

<400> SEQUENCE: 107
gacagattgg ggcatctaac agacagactg aggcatctaa cagacagatt ggggcatcta     60
acagacagac tgatgcatct aacagacaga ctgatgcatc taacagacag actgaggcat    120
ctagcagtca gacag                                                     135

<210> SEQ ID NO 108
<211> LENGTH: 135
<212> TYPE: DNA
<213> ORGANISM: Mus musculus

<400> SEQUENCE: 108
gacagattgg ggcatctaac agacagactg aggcatctaa cagacagatt gggacatcta     60
acagacagac tgatgcatct aacagacaga ctgatgcatc taacagacag actgaggcat    120
ctagcagtca gacag                                                     135

<210> SEQ ID NO 109
<211> LENGTH: 135
<212> TYPE: DNA
<213> ORGANISM: Mus musculus

<400> SEQUENCE: 109
gacagattgg ggcatctaac agacagactg aggcatctaa cagacagatt ggggcatcta     60
acagacagac tgatgcatct aacagacaga ctgatgcatc taacagatag actgaggcat    120
ctagcagtca gacag                                                     135

<210> SEQ ID NO 110
<211> LENGTH: 135
<212> TYPE: DNA
<213> ORGANISM: Mus musculus

<400> SEQUENCE: 110
gacagattgg ggcatctaac agacagactg aggcatctaa cagacagatt ggggcatcta     60
acggacagac tgatgcatct aacagacaga ctgatgcatc taacagacag actgaggcat    120
ctagcagtca gacag                                                     135

<210> SEQ ID NO 111
<211> LENGTH: 135
<212> TYPE: DNA
<213> ORGANISM: Mus musculus
```

```
<400> SEQUENCE: 111
gacagattgg ggcatctaac agacagactg aggcatctaa cagacagatt ggggcatcta      60
acagacagac tgatgcatct aacagacaga ctgatgcatc taacagacag actgagacat     120
ctagcagtca gacag                                                     135

<210> SEQ ID NO 112
<211> LENGTH: 135
<212> TYPE: DNA
<213> ORGANISM: Mus musculus

<400> SEQUENCE: 112
gacagattgg ggcgtctaac agacagactg aggcatctaa cagacagatt ggggcatcta      60
acagacagac tgatgcatct aacagacaga ctgatgcatc taacagacag actgaggcat     120
ctagcagtca gacag                                                     135

<210> SEQ ID NO 113
<211> LENGTH: 135
<212> TYPE: DNA
<213> ORGANISM: Mus musculus

<400> SEQUENCE: 113
gacagattgg ggcgtctaac agacagactg aggcatctaa cagacagatt ggggcatcta      60
acagacaggc tgatgcatct aacagacaga ctgatgcatc taacagacag actgaggcat     120
ctagcagtca gacag                                                     135

<210> SEQ ID NO 114
<211> LENGTH: 135
<212> TYPE: DNA
<213> ORGANISM: Mus musculus

<400> SEQUENCE: 114
gacagattgg ggcatctaac agacagactg aggtatctaa cagacagatt ggggcatcta      60
acagacagac tgatgcatct aacagacaga ctgatgcatc taacagacag actgaggcat     120
ctagcagtca gacag                                                     135

<210> SEQ ID NO 115
<211> LENGTH: 135
<212> TYPE: DNA
<213> ORGANISM: Mus musculus

<400> SEQUENCE: 115
gacagattgg ggcatctaac agacagactg aggcatctaa cagacagatt ggggcatcta      60
acagacagac tgatgcatct aacagacaga ctgacgcatc taacagacag actgaggcat     120
ctagcagtca gacag                                                     135

<210> SEQ ID NO 116
<211> LENGTH: 135
<212> TYPE: DNA
<213> ORGANISM: Mus musculus

<400> SEQUENCE: 116
gacagattgg ggcatctaac agacagactg aagcatctaa cagacagatt ggggcatcta      60
acagacagac tgatccatct aacagacaga ctgatgcatc taacagacag actgaggcat     120
ctagcagtca gacag                                                     135
```

```
<210> SEQ ID NO 117
<211> LENGTH: 135
<212> TYPE: DNA
<213> ORGANISM: Mus musculus

<400> SEQUENCE: 117
ggcagattgg ggcatctaac agacagactg aggcatctaa cagacagatt ggggcatcta      60
acagacagac tgatgcatct aacagacaga ctgatgcatc taacagacag actgaggcat     120
ctagcggtca gacag                                                      135

<210> SEQ ID NO 118
<211> LENGTH: 114
<212> TYPE: DNA
<213> ORGANISM: Mus musculus

<400> SEQUENCE: 118
gacagattga ggcatctagc agacagactg aggcatctaa ccgacagact gaggcatcta      60
gcagacagac tgaagcatct agcagacaga ctgaaacatc taacaaacag aaag           114

<210> SEQ ID NO 119
<211> LENGTH: 552
<212> TYPE: DNA
<213> ORGANISM: Mus musculus

<400> SEQUENCE: 119
atgccattga ggcatctagc agacagattg gggcatctgg cagacagact gaggcatcta      60
acagacagat tgaggcatct agcagacaga ctgaggcatc taacagacag actgaggcat     120
ctagcagaca gactgaggca tctagcagac agactgaaac atctaacaga cagattgggg     180
catctaacag acagatcatg gcatctaaca gacagattgg ggcatctaac agacagattg     240
aggcatctaa cagacagatt ggggcatcta acagacagac agaggtatct agcagacaga     300
ttgaggcatc taacagacag attggggcat ctaacagaca gactgaggca tctaacagac     360
agattggggc atctaacaga cagactgagg catctaacag acagattggg gcatctaaca     420
gacagactga tgcatctaac agacagactg aggcatctag cagacagaca gaggcatcta     480
gcagacagac agaggcatct agcagacaga ctgaggcatc tagcagacaa attgaggcat     540
cagctgcagc tg                                                         552

<210> SEQ ID NO 120
<211> LENGTH: 237
<212> TYPE: DNA
<213> ORGANISM: Mus musculus

<400> SEQUENCE: 120
gaaaaagtga aaaccttgaa agcgcaaaac tccgagctgg catccacggc caacacgctc      60
agggaacagg tggcactgct taagcagaaa gtcatgaacc acgttaacag tgggtgccaa     120
ctcatgctaa cgcagcagtt gcaaacgttt tgggaacaga ctgtcagggc tgaggggcaa     180
tggaagaaaa aaaataacag agacaaactt gagaacttga ctggttgcga cagagaa       237

<210> SEQ ID NO 121
<211> LENGTH: 228
<212> TYPE: DNA
<213> ORGANISM: Mus musculus

<400> SEQUENCE: 121
cggatcaagg cagagaggaa gcgcatgagg aaccgcattg ccgcctccga gtgccggaaa      60
```

```
aggaagctgg agcggatcgc tcggctagag gaaaaagtga aaaccttgaa agcgcaaaac    120
tccgagctgg catccacggc caacatgctc agggaacagg tggcacagct taagcagaaa    180
gtcatgaacc acgttaacag tgggtgccaa ctcatgctaa cacagcag                 228

<210> SEQ ID NO 122
<211> LENGTH: 149
<212> TYPE: DNA
<213> ORGANISM: Mus musculus

<400> SEQUENCE: 122
gggcatctgg cagacagact gaggcatcta acagacagat tgaggcatct agcagacaga     60
ctgaggcatc taacagacag actgaggcat ctagcagaca gactgaggca tctagcagac    120
agactgaaac atctaacaga cagatatgg                                      149

<210> SEQ ID NO 123
<211> LENGTH: 168
<212> TYPE: DNA
<213> ORGANISM: Mus musculus

<400> SEQUENCE: 123
catctaacag acagactgag gcatctaaca gacagattgg ggcatctaac agacagactg     60
aggcatctaa cagacagatt gaggcatcta acagacagac tgatgcatct aacagacaga    120
ctggggcatc tagcagacag acagaggcat ctagcagaca gacagaga                 168

<210> SEQ ID NO 124
<211> LENGTH: 132
<212> TYPE: DNA
<213> ORGANISM: Mus musculus

<400> SEQUENCE: 124
gcagacagat tggggcatct ggcagacaga ctgaggcatc taacagacag attgaggcat     60
ctagcagaca gactgaggca tctaacagac agactgaggc atttagcaga cagactgagg    120
catctagcag ac                                                        132

<210> SEQ ID NO 125
<211> LENGTH: 132
<212> TYPE: DNA
<213> ORGANISM: Mus musculus

<400> SEQUENCE: 125
gcagacagat tggggcatct ggcagacaga ctgaggcatc taacagacag attgaggcat     60
ctagcagaca gactgagaca tctaacagac agactgaggc atttagcaga cagactgagg    120
catctagcag ac                                                        132

<210> SEQ ID NO 126
<211> LENGTH: 81
<212> TYPE: DNA
<213> ORGANISM: Mus musculus

<400> SEQUENCE: 126
gcagacagac tgaggcatct aacagacaga ttgaggcatc tagcagacag actgaggcat     60
ctaacagaca gactgaggca c                                               81

<210> SEQ ID NO 127
<211> LENGTH: 159
<212> TYPE: DNA
```

<213> ORGANISM: Mus musculus

<400> SEQUENCE: 127

| acagacagat tgggcatct aacagacaga ctgaggcatc taacagacag attggggcat | 60 |
| ctaacagaca gactgaggca tctaacagac agattggggc atctaacaga cagactgatg | 120 |
| catctaacag acagactgag gcatctagca gacagaccg | 159 |

<210> SEQ ID NO 128
<211> LENGTH: 138
<212> TYPE: DNA
<213> ORGANISM: Mus musculus

<400> SEQUENCE: 128

| agacagaggc atctaacaga cagactgagg catctaacag acagattggg gcatctaaca | 60 |
| gacagactga ggcatctaac agacagattg ggcatctaa cagacagact gatgcatcta | 120 |
| acagacagac tgaggccc | 138 |

<210> SEQ ID NO 129
<211> LENGTH: 117
<212> TYPE: DNA
<213> ORGANISM: Mus musculus

<400> SEQUENCE: 129

| gacagattga gccatctagc agacagactg aggcatctaa cagacagact gaggcatcta | 60 |
| acagacagat tggggcatct aacagacaga ctgaggcatc tagcagacag acagagg | 117 |

<210> SEQ ID NO 130
<211> LENGTH: 117
<212> TYPE: DNA
<213> ORGANISM: Mus musculus

<400> SEQUENCE: 130

| gacagattga ggcatctagc agacagactg aggcatctaa cagacagact gaggcatcta | 60 |
| acagacagat tggggcatct aacagacaga ctgaggcatc tagcagacag acagagg | 117 |

<210> SEQ ID NO 131
<211> LENGTH: 117
<212> TYPE: DNA
<213> ORGANISM: Mus musculus

<400> SEQUENCE: 131

| ggcagattga ggcatctagc agacagactg aggcatctaa cagacagact gaggcatcta | 60 |
| acagacagat tggggcatct aacagacaga ctgaggcatc tagcagacag acagagg | 117 |

<210> SEQ ID NO 132
<211> LENGTH: 129
<212> TYPE: DNA
<213> ORGANISM: Mus musculus

<400> SEQUENCE: 132

| tatctagcag acagattgag gcatctaaca gacagattgg ggcatctgac agacaggctg | 60 |
| aggcatctaa cagacagatt ggggcatcta acagacagac tgaggcatct aacagacaga | 120 |
| ttggggcaa | 129 |

<210> SEQ ID NO 133
<211> LENGTH: 129
<212> TYPE: DNA
<213> ORGANISM: Mus musculus

```
<400> SEQUENCE: 133
tatctagcag acagattgag gcatctaaca gacagattga ggcatctaac agacaggctg    60
aggcatctaa cagacagatt ggggcatcta acagacagac tgaggcatct aacagacaga   120
ttggggcaa                                                          129

<210> SEQ ID NO 134
<211> LENGTH: 228
<212> TYPE: DNA
<213> ORGANISM: Mus musculus

<400> SEQUENCE: 134
cggatcaagg cagagaggaa gcgcatgagg aaccgcattg ccgcctccaa gtgccggaaa    60
aggaagctgg agcggatcgc tcggctagag gaaaaagtga aaaccttgaa agcgcaaaac   120
tccgagctgg catccacggc caacatgctc agggaacagg tggcacagct taagcagaaa   180
gtcatgaacc acgttaacag tgggtgccaa ctcatgctaa cacagcag                228

<210> SEQ ID NO 135
<211> LENGTH: 132
<212> TYPE: DNA
<213> ORGANISM: Mus musculus

<400> SEQUENCE: 135
ttggggcatc taacagacag actgaggcat ctaacagaca gattggggca tctaacagac    60
agactgatgc atctaacaga cagactgagg catctagcag acagacagag gcatctagca   120
gacagacaga aa                                                      132

<210> SEQ ID NO 136
<211> LENGTH: 108
<212> TYPE: DNA
<213> ORGANISM: Mus musculus

<400> SEQUENCE: 136
ttggggcatc taacagacag actgaggcat ctaacagaca gattggggca tctaacagac    60
agactgatgc atctaacaga cagactgagg catctagcag acacccag               108

<210> SEQ ID NO 137
<211> LENGTH: 132
<212> TYPE: DNA
<213> ORGANISM: Mus musculus

<400> SEQUENCE: 137
gggcatctaa cagacagact gaggcatcta acggacagat tggggcatct aacagacaga    60
ctgaggcatc taacagacag attggggcat ctaacagaca gactgatgca tctaacagac   120
agactgaggc ac                                                      132

<210> SEQ ID NO 138
<211> LENGTH: 132
<212> TYPE: DNA
<213> ORGANISM: Mus musculus

<400> SEQUENCE: 138
gggcatctaa cagacagact gaggcatcta acagacagat tggggcatct aacagacaga    60
ctgaggcatc taacagacag attggggcat ctaacagaca gactgatgca tctaacagac   120
agactgaggc ac                                                      132
```

<210> SEQ ID NO 139
<211> LENGTH: 153
<212> TYPE: DNA
<213> ORGANISM: Mus musculus

<400> SEQUENCE: 139

| | | | | | |
|---|---|---|---|---|---|
| aggcatctaa | cagacagatt | ggggcatcta | acagacagac | tgaggcatct | aacagacaga | 60 |
| ttggggcatc | taacagacag | actgatgcat | ctaacagaca | gactgaggca | tctagcagac | 120 |
| agacagaggc | atctagcaga | caggcagagg | cac | | | 153 |

<210> SEQ ID NO 140
<211> LENGTH: 153
<212> TYPE: DNA
<213> ORGANISM: Mus musculus

<400> SEQUENCE: 140

| | | | | | |
|---|---|---|---|---|---|
| aggcatctaa | cagacagatt | ggggcatcta | acagacagac | tgaggcatct | aacagacaga | 60 |
| ttggggcgtc | taacagacag | actgatgcat | ctaacagaca | gactgaggca | tctagcagac | 120 |
| agacagaggc | atctagcaga | cagacagagg | cac | | | 153 |

<210> SEQ ID NO 141
<211> LENGTH: 1752
<212> TYPE: DNA
<213> ORGANISM: Mus musculus

<400> SEQUENCE: 141

| | | | | | |
|---|---|---|---|---|---|
| atgtcccatc | aacctctgag | ctgcctgact | gagaagggggg | acagcccttg | tgagacccca | 60 |
| ggaaatggac | cctccaatat | ggttcacccc | agcctggaca | cattcacccc | tgaggagctg | 120 |
| ctgcagcaaa | tgaaggaact | cctggttgag | aaccaccagc | tgaaagaagc | catgaagcta | 180 |
| aataatcaag | ctatgaaagg | gcgatttgag | gagctgtccg | cctggacaga | gaagcagaag | 240 |
| gaagagcgcc | tgttgtttga | gatgcaaagc | aaagaggtta | aggagcgcct | taaggccctg | 300 |
| actcatgaaa | atgagaggct | gaaggaagag | cttggaaaat | tcaaagagaa | atcagaaaag | 360 |
| ccattggaag | acctcacagg | tggctacagg | tatcccagag | ccttggagga | ggaagtggag | 420 |
| aagctgaaga | cccaggtgga | gcaggaagtg | gagcatctga | agatccaggt | gatgcgcctt | 480 |
| cgggctgaaa | aggcagacct | gctgggcatc | gtctcagaac | tgcagctcaa | actcaactcc | 540 |
| ggcggctcct | cggaagactc | cttcgttgag | atcaggatga | ccgaaggaga | gactgaaggg | 600 |
| gcaatgaagg | agatgaagaa | ctgccctaca | cccacaagaa | cagaccccat | cagcttgagc | 660 |
| aactgtacag | aggatgccag | gagttgtgcg | gagtttgaag | aactgactgt | gagccagctt | 720 |
| ctgctttgcc | taagggaagg | aaaccaaaag | gtggagagac | ttgaagtcgc | cctcagagaa | 780 |
| gccaaagaaa | gaatttcaga | ttttgaaaag | aaagcaaatg | ccattcttc | tactgagaag | 840 |
| cagacagcga | ggagagcaga | cagagagaag | gaggacaaag | gccaagagag | tgttggaagc | 900 |
| gaagtggaaa | cactgagcat | tcaagtgacc | tctctgttta | aggagcttca | agaggcacac | 960 |
| acaaaactca | gtgaggctga | gctgatgaag | aagagacttc | aagaaaagtg | tcaggctctg | 1020 |
| gagaggaaga | actctgcaac | accatcagag | ctgaatgaaa | agcaagagct | cgtttacagt | 1080 |
| aacaagaagt | tagagctgca | ggtggagagc | atgcgctccg | aaatcaagat | ggagcaggcc | 1140 |
| aagacagagg | aggagaagtc | caggttagcc | actctgcagg | caactcacaa | caagctcctt | 1200 |
| caagaacata | taaggcact | gaaaacaatt | gaagaactaa | ccaagcaaca | ggcagaaaag | 1260 |
| gtggacaaga | tgttgctgca | ggagctcagc | gagaagctgg | agctggcaga | gcaggctctg | 1320 |

-continued

```
gcatccaaac agctccagat ggatgagatg aagcagacgc tcgctaagca ggaggaagac    1380
ctggagacca tggccgtcct cagggctcag atggaggtgt actgctcaga ttttcacgct    1440
gagagagcag caagagagaa gattcatgaa gaaaaggagc agctggcctt gcagctcgcg    1500
attttgctga agagaacaa tgacattgaa gagggaggca gtagacagtc cctgatggaa     1560
atgcagtgcc gacacggggc aagaaccagt gactctgacc agcagactta cctgtttcaa    1620
agaggagccg aggacaggag ctggcagcac gggcagcagc ctcgcagtat tccgattcac    1680
tcctgcccca gtgcggggga ggtcctgccg gacatcgaca cgcttcagat ccatgtgatg    1740
gactgcatca tt                                                       1752
```

<210> SEQ ID NO 142
<211> LENGTH: 324
<212> TYPE: DNA
<213> ORGANISM: Mus musculus

<400> SEQUENCE: 142

```
ctgaagaccc aggtggagca ggaagtggag catctgaaga tccaggtgat gcgccttcgg    60
gctgaaaagg cagacctgct gggcatcgtc tcagaactgc agctcaaact caactccggc    120
ggctcctcgg aagactcctt cgttgagatc aggatgaccg aaggagagac tgaaggggca    180
atgaaggaga tgaagagctg ccctacaccc acaagaacag accccatcag cttgagcaac    240
tgtacagagg atgccaggag ttgtgcggag tttgaagaac tgactgtgag ccagcttctg    300
ctttgcctaa gggaaggaaa ccaa                                          324
```

<210> SEQ ID NO 143
<211> LENGTH: 186
<212> TYPE: DNA
<213> ORGANISM: Mus musculus

<400> SEQUENCE: 143

```
catctgaaga tccaggtgat gcgccttcgg gctgaaaagg cagacctgct gggcatcgtc    60
tcagaactgc agctcaaact caactccggc ggctcctcgg aagactcctt cgttgagatc    120
aggatgaccg aaggagagac tgaaggggca atgaaggaga tgaagaactg ccctacaccc    180
acaaga                                                              186
```

<210> SEQ ID NO 144
<211> LENGTH: 186
<212> TYPE: DNA
<213> ORGANISM: Mus musculus

<400> SEQUENCE: 144

```
catctgaaga tccaggtgat gcgccttcgg gctgaaaagg cagacctgct gggcatcgtc    60
tcagaactgc agctcaaact caactccggc ggctcctcgg aagactcctt cgttgagatc    120
aggatgaccg aaggagagac tgaaggggca atgaaggaga tgaagaactg ccctgcaccc    180
acaaga                                                              186
```

<210> SEQ ID NO 145
<211> LENGTH: 186
<212> TYPE: DNA
<213> ORGANISM: Mus musculus

<400> SEQUENCE: 145

```
catctgaaga tccaggtgat gcgccttcgg gctgaaaagg cagacctgct gggcatcgtc    60
```

```
tcagaactgc ggctcaaact caactccggc ggctcctcgg aagactcctt cgttgagatc    120
aggatgaccg aaggagagac tgaaggggca atgaaggaga tgaagaactg ccctacaccc    180
acaaga                                                              186
```

<210> SEQ ID NO 146
<211> LENGTH: 306
<212> TYPE: DNA
<213> ORGANISM: Mus musculus

<400> SEQUENCE: 146

```
atgttgagtc gactgcagga gctccgcaag gaggaggaaa ccctgctgcg tctaaaggcg    60
gctctacacg accaactgaa ccgcctcaag gttgaagaat tagcccttca atccatgata   120
aattctcgag gaaggaccga gacactgtct tctcagcctg cacctgaaca gttatgtgat   180
atgtccctac atgtagacaa cgaagtgaca ataaatcaga ctacactgaa gctgagcaca   240
aggagcccta tggaagaaga ggaggaggaa gaggaggagg aagaggagga ggaagaatct   300
gattcg                                                              306
```

<210> SEQ ID NO 147
<211> LENGTH: 249
<212> TYPE: DNA
<213> ORGANISM: Mus musculus

<400> SEQUENCE: 147

```
gccctaagga agtggaaggg gatgttgagt cgactgcagg agctccgcaa ggaggtggaa    60
accctgctgc gtctaaaggc ggctctacac gaccaactga accgcctcaa ggttgaagaa   120
ttagcccttc aatccatgat aaattctcga ggaaggaccg agacactgtc ttctcagcct   180
gcacctgaac agttatgtga tatgtcccta catgtagaca acgaagtgac aataaatcag   240
actaggccg                                                           249
```

<210> SEQ ID NO 148
<211> LENGTH: 237
<212> TYPE: DNA
<213> ORGANISM: Mus musculus

<400> SEQUENCE: 148

```
aggaagtgga agggacgtt gagtcgactg caggagctcc gcaaggaggt ggaaaccccg    60
ctgcgtctaa aggcggctct acacgaccaa ctgaaccgcc tcaaggttga agaattagcc   120
cttcaatcca tgataaattc tcgaggaagg accgagacac tgtcttctca gcctgcacct   180
gaacagttat gtgatatgtc cctacatgta gacaacgaag tgacaataaa tcagact     237
```

<210> SEQ ID NO 149
<211> LENGTH: 1239
<212> TYPE: DNA
<213> ORGANISM: Mus musculus

<400> SEQUENCE: 149

```
atgggagacg acagaccgtt tgtgtgcagt gccccgggct gtggacagag atttacaaat    60
gaggaccacc tggcagttca taaacataag catgagatga cactgaaatt ggcccagcc   120 cgaacggact cagtcatcat tgcagatcaa acgcctactc caactagatt cctgaagaac   180
tgtgaggaag tggggctctt caatgaacta gctagctcct ttgaacatga atttaagaaa   240
gcttctgatg acgatgagaa aaagggtgct gctgggcctc ttgacatgtc tctgccttct   300
acaccagaca tcaaaatcaa ggaagaagag ccagtggaag tagactcatc gcccctgac   360
```

```
agtcctgctt ctagcccctg ttccccacca ctgaaggaga aggaagttac cacaaaaccg      420
gttgtgatct ctacccctac acctaccatt gtacgtcctg gctccctgcc tctccactta      480
ggttatgatc cacttcatcc aactcttcct tccccaacct ctgtcatcac acaggctcca      540
ccatccaaca ggcaaatagg atctcctact ggctccctcc ctctcgtcat gcatcttgct      600
aatggacaga ccatgcctat gttgccaggg cctccagtac agatgccttc tgttatttcg      660
ctggccagac ctgtgtccat ggtgcccaac attcctggta tacctggccc accggttaac      720
aacagtggct ccatttctcc ctctggccac cctatgccgt cagaagccaa aatgagacta      780
aaagccacgc tgacccatca gtttcttca atcaatggag gttgtggaat ggtggtgggt       840
actgcaagca ccatggtgac tgcccgtcca gagcaaaacc agatcctcat ccagcaccca      900
gatgccccat cccctgccca gccacaggtc tctccagctc agcccacccc tagcactggg      960
ggacggcgac ggcgtacagt ggatgaagat ccagatgagc ggcggcagcg gtttttagag     1020
cgaaacagag ctgcagcctc tcgatgccgg caaaagcgga actgtgggt gtcctccctg      1080 gaaaagaagg cagaagaact tacttctcag aacattcagc tgagtaatga agtcacatta     1140
ctacgcaatg aggtggctca gctgaagcag ctactgttag ctcataaaga ttgcccagtc     1200
actgcactac agaaaaagac tcaaggctac ctaggtaag                            1239

<210> SEQ ID NO 150
<211> LENGTH: 168
<212> TYPE: DNA
<213> ORGANISM: Mus musculus

<400> SEQUENCE: 150
cgatgccggc aaaagcggaa actgtgggtg tcctccctgg aaaagaaggc agaagaactt       60
acttctcaga acattcagct gagtaatgaa gtcacattac tacgcaatga ggtggctcag      120
ctgaagcagc tactgttagc tcataaagat tgtccagtca ccgcacaa                   168

<210> SEQ ID NO 151
<211> LENGTH: 3093
<212> TYPE: DNA
<213> ORGANISM: Mus musculus

<400> SEQUENCE: 151
atgacaaacc caaaggaaa gaggagaggt actcagtcta tgttctctag gccttttagg        60
aaacatggag ttgtttcttt ggccacatac atgcgaatct acaagaagcg tgatattgta      120
gacatcaagg gaatgggcac tgttcaaaaa ggaatgccct gtaagtgtta ccacggcaaa      180 accggaaagag tctacaatgt cacccagcat gccatgggca tcattgtaaa caagcaagtt     240
aaaggcaaga ttctggccaa gaggatcaat gtgcagattg agcacatcaa gcactcgaag      300
agcagagacg gcttcctgaa gcagggagag ccgcccatt tcgaatacct gctgtaccca       360
cttcactcag cgtccatcac gggcctggcc acctgcatcc gaaaacccct cattgccacc      420
tgctccctgg atcgctccgt tcgcatctgg aattacgagt cgaattcctc ctgctgcaag      480
gctctcagag aagacctttg ctcctcctc cttttccaca tcactgcccc ggccacccttt      540 agctccccac cagtgatatt cttctgcaca ctggagctat ataaggaata ccaagaagag      600
gcctacacgg tcagccttca cccctccgga cactacattg tggtgggggtt tgctgacaaa     660 cttcgcctta tgaacctgct cattgatgac atccgttctt tcaaagaata ttctgtcaga      720
ggatgcaaag agtgtgcctt tagcaatgga ggtcacctgt ttgctgccgt caatggtaat      780
```

```
gtgattcaca tcttcaccac cacgaacctg gagaatatca acaacctgaa aggccacaca    840
gggaagaggg agacagagtg tgtactcaag gtctgtagtt acaactcggt cactatctcc    900
cctgacggca agttatctt cgctgttgga tcagaccaga ctcttaagga gatcgccgat     960
tctttgatcc ttcgagagat accagcattt gatgtcgtct acacggccat caccatctca   1020
cattccggac gcatgatatt cgtgggcact tcagtgggga ctatccgtgc catgaagtac   1080
ccgctgcctc tgcagagaga attcaatgag taccaggctc acgctggccc cgtcacgaag   1140
atactgctca ccttcgatga ccagttcctg ctgacggtct ctgaggatgg ctgcctgttc   1200
acctggaaag tctttgataa ggagggtcgg ggaatcaaac gagagaggga ggtgggcttt   1260
gctgaagagg tactcgtgac taagacagac atggaggaga agatactcca caggaactta   1320
gcaacggaat tcagaaggcc aatgagcaag caccttgagt gtcccacatc ggaaactggg   1380
ccactcacaa caataaatat ctccccggtc cagcccaggc cttggggcca tgtactcacc   1440
tgcagaacac ccgtcagcac tgacagtgct gttgcgtcta caagaggctc tgtggacagc   1500
gcagtgaagc cagataggtc aactccaacc caggaagtcc gcatcccacc aaagccagcc   1560
tcgggagtcc acaccaggtg ccagttagga gtacagaaac agatggaaca cgtttctgtt   1620
gtcatggagg tacgagaaac aaaccggcag agacagggtg ggggtgcgcg gaatgtaatc   1680
aaggctcaga tcatgctgga gctgaagacg cgtgtagagg aactgaaaat ggagaacgag   1740
tatcagctcc ggctgaagga catgaactac tcagagaaga tcaaggagct gacagacaag   1800
ttcatccagg agatggagtc cttgaagacg aagaaccagg ttttaaaaac agagaaagaa   1860
aaacaggaca tcagtcaccg agagcactta gaagacctca tagaaagaca gagccgggag   1920
ctgcaagacc tggaatgttg taacaaccag aagctgctcc ttgaatacga gaagtaccag   1980
gagctgcagc tcaagtccca gaggatgcag gaggagtacg aaaaacagct ccgagacaat   2040
gatgagacca agagccaagc actgaggag ctgaccgagt tctacgaggc caaactccag   2100
gagaaaaccg gccttctgga agaggccctc agcacagcag cctcaccacc ccttccctca   2160
gcacacgttc tctctccctt ccccactctg agccaggcac aggaagatgt ccgacagcag   2220
ctccgggaat tcgaggaaac caagaagcag attgaagaag atgaggacag ggagatccaa   2280
gacatcaaaa ccaagtatga gagaaagctt cgagatgaaa aggagtccaa ccttcggctt   2340
aagggagaaa caggaatcat gaggaagaag ttcagcagcc tgcagaagga gatcgaagag   2400
cgcaccaatg acatcgagct cctcaaaacg gagcaggtga agctgcaggg ggtcatcagg   2460
tccctagaga aggacatcca aggactcaag agagagatcc aggagaggga tgagaccatt   2520
caagacaagg agaagcgaat ttatgatctg aagaagaaga accaagagtt agagaaattc   2580
aaatttgtcc ttgactacaa aataaaggaa ctgaagaagc aaatagaacc aagggagaac   2640
gagatcaaag tgatgaagga gcagatccag gagaaccctg tcaatcactg gctcagaagc   2700
agggagagag aatgtgtcac acagccaagg catctgcggc ttccagctcc ccagaacaag   2760
ttagatggga atttagcttg tggaccggta agaggtcggt tgtgccactc agacgcgacc   2820
tcaggggccc tgaatgttca gggcatcctt tgtctcttcc acctgccatt tccctgtgat   2880
aggacgccat ctttcttccc cggagaagct tgtctcctgg ttttctctct tctgatagat   2940
gttctatgta gacccacctc tgacgtacca gtcgctgctg gcgattttct tccgtgtggc   3000
ggacctctgc acttgcctcc agagctgcac caccttacag tcatccggac caatgccagc   3060
ccacagaaat gctacccacc caccagtcct ctg                                3093
```

<210> SEQ ID NO 152
<211> LENGTH: 210
<212> TYPE: DNA
<213> ORGANISM: Mus musculus

<400> SEQUENCE: 152
aagaagttca gcagcctgca gaaggagatc gaagagcgca ccaacgacat cgagctcctc    60
aagtcggagc ggatgaagct gcagggcatc atcagatccc tggagaaaga catccaaggg   120
ctcaagagag agatccagga gagggacgag accattcaag acatggagaa gcttgactac   180
aaggacgatt ataattcaaa cctagagatc                                    210

<210> SEQ ID NO 153
<211> LENGTH: 168
<212> TYPE: DNA
<213> ORGANISM: Mus musculus

<400> SEQUENCE: 153
aagaagttca gcagcctgca gaaggagatc gaagagcgca ccaacgacat cgagctcctc    60
aagtcggagc ggatgaagct gcagggcatc atcagatccc tggagaaaga catccaaggg   120
ctcaagagag agatccagga gagggacgag accattcaag acatggag               168

<210> SEQ ID NO 154
<211> LENGTH: 651
<212> TYPE: DNA
<213> ORGANISM: Mus musculus

<400> SEQUENCE: 154
atggaagtag aaaacgaagc ccactgctgc cctggcagct catcaggcgg gtccagagag    60
tacaaggtgg taatgctggg cgcaggggggc gttggtaaaa gcgcagtcac aatgcagttt   120
ataagccacc agttcccgga ctatcacgac cccacaatcg aagatgctta taaaacccag   180
gtgaggattg ataatgagcc tgcttactta gacatcttgg acactgctgg tcaggcagag   240
ttcacggcca tgcgggagca gtacatgcgt gggggagagg gcttcatcat ctgctattct   300
gtcactgacc gccagtcatt ccaggaggct gccaagttca aggagcttat tttccaggtc   360
cgtcacacct atgaaattcc ccttgtgcta gtgggtaaca aaattgactt ggagcagttc   420
cgtcaggtat ctacagaaga aggcatgaat cttgctcgag actacaactg tgccttcttt   480
gagacatctg cagccctgcg attcggtatc gatgatgctt ttcaaggctt agtgagagaa   540
attcgcagga aggaatccat gctgtccttg gtggaaagga aattgaagag aaggacagc    600 ctgtggaaga agataaaagc ctccctgaag aagaagagag aaaacatgtt g            651

<210> SEQ ID NO 155
<211> LENGTH: 150
<212> TYPE: DNA
<213> ORGANISM: Mus musculus

<400> SEQUENCE: 155
gcagccctgc gattcggtat cgatgatgct cttcaaggct tagtgagaga aattcgcagg    60
aaggaatcca tgctgcccct tggtggaaagg aaattgaaga ggaaggacag cctgtggaag   120
aagataaaag cctcccctgaa gaagaagagg                                  150

<210> SEQ ID NO 156
<211> LENGTH: 420
<212> TYPE: DNA
<213> ORGANISM: Mus musculus

<400> SEQUENCE: 156

| ggtgccacag ttattacaaa cctcctatca gccatcccat atattggaac aaccctagtc | 60 |
| gaatgaattt gagggggctt ctcagtagac aaagccacct tgacccgatt cttcgctttc | 120 |
| cacttcatct taccatttat tatcgcggcc ctagcaatcg ttcacctcct cttcctccac | 180 |
| gaaacaggat caaacaaccc aacaggatta aactcagatg cagataaaat tccatttcac | 240 |
| ccctactata caatcaaaga tatcctaggt atcctaatca tattcttaat tctcataacc | 300 |
| ctagtattat ttttcccaga catactagga gacccagaca actacatacc agctaatcca | 360 |
| ctaaacaccc cacccccatat taaacccgaa tgatatttcc tatttgcata cgccattcta | 420 |

<210> SEQ ID NO 157
<211> LENGTH: 123
<212> TYPE: DNA
<213> ORGANISM: Mus musculus

<400> SEQUENCE: 157

| tcagatgcag ataaaattcc atttcacccc tactatacaa tcaaaaatat cctaggtatc | 60 |
| ctaatcatat tcttaattct cataacccta gtattatttt tcccagacat actaggagac | 120 |
| cca | 123 |

<210> SEQ ID NO 158
<211> LENGTH: 933
<212> TYPE: DNA
<213> ORGANISM: Mus musculus

<400> SEQUENCE: 158

| atgaaggctc tgtgggccgt gctgttggtc acattgctga caggatgcct agccgaggga | 60 |
| gagccggagg tgacagatca gctcgagtgg caaagcaacc aaccctggga gcaggccctg | 120 |
| aaccgcttct gggattacct gcgctggtgt cagacgctgt ctgaccaggt ccaggaagag | 180 |
| ctgcagagct cccaagtcac acaagaactg acggcactga tggaggacac tatgacggaa | 240 |
| gtaaaggctt acaaaaagga gctggaggaa cagctgggtc cagtggcgga ggagacacgg | 300 |
| gccaggctgg gcaaagaggt gcaggcggca caggcccgac tcggagccga catggaggat | 360 |
| ctacgcaacc gactcgggca gtaccgcaac gaggtgcaca ccatgctggg ccagagcaca | 420 |
| gaggagatac gggcgcggct ctccacacac ctgcgcaaga tgcgcaagcg cttgatgcgg | 480 |
| gatgccgatg atctgcagaa gcgcctagct gtgtacaagg caggggcacg cgagggcgcc | 540 |
| gagcgcggtg tgagtgccat ccgtgagcgc ctggggcctc tggtggagca aggtcgccag | 600 |
| cgcactgcca acctaggcgc tggggccgcc cagcctctgc gcgatcgcgc ccaggctttt | 660 |
| ggtgaccgca tccgagggcg gctggaggaa gtgggcaacc aggcccgtga ccgcctagag | 720 |
| gaggtgcgtg agcacatgga ggaggtgcgc tccaagatgg aggaacagac ccagcaaata | 780 |
| cgcctgcagg cggagatctt ccaggcccgc ctcaagggct ggttcgagcc aatagtggaa | 840 |
| gacatgcatc gccagtgggc aaacctgatg gagaagatac aggcctctgt ggctaccaac | 900 |
| cccatcatca ccccagtggc ccaggagaat caa | 933 |

<210> SEQ ID NO 159
<211> LENGTH: 90
<212> TYPE: DNA
<213> ORGANISM: Mus musculus

<400> SEQUENCE: 159

| acggaagtaa aggcttacaa aaaggagctg gaggaacagc tgggtccagt ggcggaggag | 60 |

```
acacgggcca ggctgggcaa agaggagcag                                    90

<210> SEQ ID NO 160
<211> LENGTH: 2085
<212> TYPE: DNA
<213> ORGANISM: Mus musculus

<400> SEQUENCE: 160
atgctgccca gcttggcact gctcctgctg ccgcctgga cggttcgggc tctggaggta     60
cccactgatg caacgccgg gctgctggca gaacccaga tcgccatgtt ctgtggtaaa    120
ctcaacatgc acatgaatgt gcagaatgga aagtgggagt cagacccgtc agggaccaaa    180
acctgcattg gcaccaagga gggcatcttg cagtactgcc aagaggtcta ccctgaactg    240
cagatcacaa acgtggtgga agccaaccag ccagtgacca tccagaactg gtgcaagcgg    300
ggccgcaagc agtgcaagac acacccac atcgtgattc cttaccgttg cctagttggt    360
gagtttgtga gcgacgccct tctcgtgccc gacaagtgca agttcctaca ccaggagcgg    420
atggatgttt gtgagaccca tcttcactgg cacaccgtcg ccaaagagac atgcagcgag    480
aagagcacta acttgcacga ctatggcatg ctgctgccct gcggcatcga caagttccga    540
ggggtagagt ttgtatgctg cccgttggcc gaggaaagcg acagcgtgga ttctgcggat    600
gcagaggagg atgactctga tgtctggtgg gttggagcgg acacagacta cgctgatggc    660
ggtgaagaca agtagtaga agtcgccgaa gaggaggaag tggctgatgt tgaggaagag    720
gaagctgatg atgatgagga tgtggaggat ggggacgagg tggaggagga ggccgaggag    780
ccctacgaag aggccaccga gagaacaacc agcactgcca ccaccaccac aaccaccact    840
gagtccgtgg aggaggtggt ccgagttccc acgacagcag ccagcacccc cgacgccgtc    900
gacaagtacc tggagacacc cggggacgag aacgagcatg cccatttcca gaaagccaaa    960
gagaggctgg aagccaagca ccgagagaga atgtcccagg tcatgagaga atgggaagag   1020
gcagagcgtc aagccaagaa cttgcccaaa gctgacaaga aggccgttat ccagcatttc   1080
caggagaaag tggaatctct ggaacaggaa gcagccaatg agagacagca gcttgtagag   1140
acacacatgg ccagagttga agccatgctc aatgaccgcc gccgcctgga cctcgagaat   1200
tacatcatcg cactgcaggc ggtgccccca aggcctcatc atgtgttcaa catgctgaag   1260
aagtacgtcc gtgcggagca gaagacagac cagcacaccc taaagcattt tgaacatgtg   1320
cgcatggtgg accccaagaa agctactcag atccggtccc aggttatgac acacctccgt   1380
gtgatctacg agcgcatgaa ccagtctctg tccctgctct acaatgtccc tgcggtggct   1440
gaggagattc aagatgaagt cgatgagctg cttcagaagg agcagaacta ctccgacgat   1500
gtcttggcca acatgatcag tgagcccaga atcagctacg aaacgacgc tctcatgcct   1560 tcgctgacgg aaaccaagac caccgtggag ctccttcccg tgaatgggga attcagcctg   1620
gatgacctcc agccgtggca cccttttggg gtggactctg tgccagccaa taccgaaaat   1680
gaagtcgagc tgttgacgc ccgccccgct gctgaccgag gactgaccac tcgaccaggt   1740
tctgggctga caaacatcaa gacggaagag atctcggaag tgaagatgga tgcagaattc   1800
ggacatgatt caggatttga agtccgccat caaaaactgg tgttctttgc tgaagatgtg   1860
ggttcgaaca aaggcgccat catcggactc atggtgggcg cgttgtcat agcaaccgtg   1920 attgtcatca ccctggtgat gttgaagaag aaacagtaca catccatcca tcatggcgtg   1980
gtggaggtcg acgccgccgt gaccccagag gagcgccatc tctccaagat gcagcagaac   2040
```

```
ggatatgaga atccaactta caagttcttt gagcaaatgc agaac         2085

<210> SEQ ID NO 161
<211> LENGTH: 201
<212> TYPE: DNA
<213> ORGANISM: Mus musculus

<400> SEQUENCE: 161
agtgagccca gaatcagcta cggaaacgac gctctcatgc cttcgctgac ggaaaccaag    60
accaccgtgg agctccttcc cgtgaatggg gaattcagcc tggatgacct ccagccgtgg   120 caccttctg gggtggactc tgtgccagcc aataccgaaa atgaggtcga gcctgttgac   180
gcccgccccg ctgctgaccg a                                            201

<210> SEQ ID NO 162
<211> LENGTH: 1236
<212> TYPE: DNA
<213> ORGANISM: Mus musculus

<400> SEQUENCE: 162
atggcgaacg tggccgacac gaagctgtac gacatcctgg gcgtccctcc cggcgctagc    60
gagaacgagc tgaagaaggc ataccgaaag ttagccaaag aataccaccc tgataagaat   120
ccaaatgctg gagacaaatt taagaaaata agttttgcat atgaagtatt gtcaaatcca   180
gagaagcgag agctgtatga cagatatgga gaacaaggcc tacgggaagg cagcggcgga   240
ggcggtggaa tggatgatat cttctcacat attttggtg gaggattgtt tggctttatg   300
ggcaatcaga gtagaagtcg aaatggcaga agaagaggcg aggacatgat gcatccacta   360
aaagtatctt tagaagacct gtacaatggc aagacaacca actacaact tagcaagaat   420 gtgctctgta gtgcatgcag tggccaaggt gggaagtctg gagctgttca gaaatgcagc   480
gcttgtcggg gtcgaggtgt gcgcattatg atcagacagc tggctccagg aatggtgcag   540
cagatgcagt ccgtgtgctc cgactgtaat ggagaagggg aggtcatcaa tgaaaaagac   600
cgctgtaaaa aatgtgaagg gaagaaggta atcaaagaag tcaagattct ggaagtccat   660
gtagacaaag gcatgaaaca tggacagagg attacgttca ctggggaagc agaccaggct   720
ccaggagtgg aacctggaga tattgttctt ttgctacagg aaaaagaaca tgaggtgttc   780
cagagagatg ggaatgattt gcatatgaca tataagatag acttgttga agctttatgt   840 ggatttcagt tcacatttaa acatcttgat gctcgtcaga ttgtggtgaa atacccccct   900
ggcaaagtaa ttgaaccagg atgtgttcgt gttgttcgag gtgaaggaat gccacagtat   960
cgtaatccct ttgaaaaggg tgatctttac ataaagtttg atgtacagtt tcctgagaat  1020
aactggatca acccagacaa actttctgaa ttagaagatc tcctgccatc tagaccagaa  1080
gttcctaatg ttattggaga cagaagaa gtggagcttc aggaatttga tagcactcga  1140
ggctctggcg tggtcagag acgtgaagcc tataatgata gctctgatga agaaagtagc  1200
agccatcatg gacctggagt gcagtgtgcc catcag                            1236

<210> SEQ ID NO 163
<211> LENGTH: 75
<212> TYPE: DNA
<213> ORGANISM: Mus musculus

<400> SEQUENCE: 163
ttgtcaaatc cagagaagcg agagctgtat gacagatatg gagaacaagg cctacgggaa    60
ggcagcggag gaggc                                                    75
```

<210> SEQ ID NO 164
<211> LENGTH: 2949
<212> TYPE: DNA
<213> ORGANISM: Mus musculus

<400> SEQUENCE: 164

| | | | | | |
|---|---|---|---|---|---|
| atgaaggctc | agcaggccat | ggacaaatat | gaaggagata | gcaaggcgag | ggagacccgg | 60 |
| agcacagcgg | ccatggtagg | ctggagaagt | gacagaggcc | tggtgacttg | caccaggctt | 120 |
| aggatgcaga | atggtagctc | actaaaagct | tttcggagca | gggtggggaa | gtggggagaa | 180 |
| ccttcctcga | gatcacacaa | agtgttgaag | accagcgaaa | cttcacaaga | tatccagaag | 240 |
| gtttctagag | aggaaagccc | ttcccagctg | acttctgccg | tgcctgccca | gaggaactgc | 300 |
| cagcccggca | gcgctgccgt | tatcaatatg | cttcgcgggg | gaggcggtgt | tagaagccca | 360 |
| tggacagatc | accacatcag | gcagcggacg | gatcaccaca | tccggcagcc | cttgttttcca | 420 |
| agccgccggt | ctccacagga | gaatgaggac | gatgacgacg | attaccagat | gttcgtcccg | 480 |
| tcctttttctt | cctcggatct | caactccacc | aggttgtgtg | aagagaacgc | ttcaagtcgc | 540 |
| ccttgcagct | ggcatctggg | cctcatcgaa | cccacagaga | tctccagctc | tggtcacagg | 600 |
| atagtccgac | gggccagtag | tgcaggtgaa | agcaacgcat | gccctcctga | agtaagaatt | 660 |
| agagactgtg | atgactctca | gtactgtccc | gggagacagc | tgcagaacag | tcctcgacca | 720 |
| ggaggagaga | gggggatgac | tccctatggg | tcgtctgtag | agttgaccat | tgatgatata | 780 |
| gaccatgtct | atgataacat | aagttttgaa | gacttaaagt | taatggttgc | taagcgggat | 840 |
| gaaactgaat | gttctttctc | caaaccatcc | agagactctg | ttcgccccaa | gagtacccca | 900 |
| gagttagcct | tctcaaagag | acaggttagc | cacagtacaa | gctctctcca | ctcaaggaaa | 960 |
| gaggcaggcc | tcggtggtca | agaggcatcc | acccaaagcg | tacatgaaca | ccaggaagtg | 1020 |
| gaagaaaaca | tctatgacac | catagggctt | ccagacccac | catcgatgaa | cttgaaccac | 1080 |
| agcagccttc | atcagcccaa | aaggagcacc | ttcctgggtc | tggaagctga | ttttgcatgc | 1140 |
| tgtgacagcc | tgagaccatt | tgtctcccag | gatagcctcc | agttcagtga | ggatgacata | 1200 |
| tcttaccacc | agggaccctc | cgatactgaa | tatttgagtt | tgttatatga | ctctccccgc | 1260 |
| tgtaatctgc | ctattgcaga | taaggctctg | tccgacaaat | tgtctgaaga | agtagatgaa | 1320 |
| atctggaatg | atctggaaaa | ttacatcaag | aaaaatgaag | acaaatcaag | agaccgcctc | 1380 |
| cttgcggcct | ttcctgtgag | caaagacgat | gcaccagaga | ggctatatgt | tgacagcacc | 1440 |
| catgagctgg | gcagggatac | aggacatgcc | acatctatgc | tggcccttcc | tacaagccag | 1500 |
| actttcctcc | tgcctgggaa | gagcagagtt | gtcagagcta | gcagggccaa | ctgctccctg | 1560 |
| gataatgaca | ttatttcaac | agaaggttcc | ttcctgagtc | ttaaccaact | ctctctggcc | 1620 |
| agtgatgggc | ctcctgtgga | caatccctat | gacctggcca | actgcagcct | gcccagaca | 1680 |
| gacccagaaa | accctgaccc | cgggatggag | gtcacagaca | agactaagag | cagggtcttt | 1740 |
| atgatggcca | ggcagtatag | tcaaaagatc | aagaaggtaa | atcagatttt | gaaagtgaaa | 1800 |
| agcccagagt | tggagcaacc | accgtccagt | cagcataggc | ccagtcacaa | agacctggtg | 1860 |
| gccatcttgg | aagagaagag | gcaaggaggg | cccgccattg | tgccaggat | cgctgaatat | 1920 |
| tcccaactgt | atgaccagat | tgtgttcaga | gagacacccc | ttaaagctca | gaaggatggc | 1980 |
| tgggccagcc | cccaaggacc | caccctccac | aggcctgtgt | cacctcccca | ggcccagggc | 2040 |
| gctggtgagg | actggctctg | gcattcgccc | tacagtaacg | gagagttggc | agatttctct | 2100 |

```
cccagacag aacaagactc aaaatcaaaa tacccccatca cattagagag caccacaaaa    2160
attaggccca ggcagttgtc gggtgcttgt tcggtgccgt ctctccaagt gtcggaccct    2220
ctgctgggct ctgtgcagca gagatgcagc gtggtggtca gccagcccca caaagagaac    2280
tcaggtcaga gtcctctta caactcgctg ggtcgcaaag caatcagcgc taaacccag     2340 ccttatagca ggcctcagtc atcttcctca atcttgataa acaaatctct ggactctatc    2400
aactacccca gtgagacaga gacgaagcaa ctactctctt cacagaaaag tcccagaggc    2460
gcgagccagc aggatttgcc gtcagggcta gcaaactcat gtcaacagga caggggcaaa    2520
cggtccgatc tcacgctcca agactcgcag aaggttctcg tggtaaatag aaatttaccc    2580
ttaagcgctc aaatagcgac gcagaactac ttttgtaatt tcaaagatcc cgagggagat    2640
gaagatgact atgtggaaat caagtcagaa gaggacgaag tgcgtctgga tctctctcca    2700
aggcggggca ggaagtctga cccacagacc ccggaccctg actgttcgga tagcatctgt    2760
agccacagca caccttactc tttgaaggag ccagtgagtg gcaggcttgg gcttcctcct    2820
tacctgacag catgtaagga ctctgataaa ctgaatgatt atctgtggag ggggccctca    2880
cccaatcagc aaaacattgt ccaatctctg agggagaaat tcagtgtct tagctcaagc    2940 agctttgcc                                                           2949

<210> SEQ ID NO 165
<211> LENGTH: 138
<212> TYPE: DNA
<213> ORGANISM: Mus musculus

<400> SEQUENCE: 165
tttatgatgg ccaggcagta tagtcaaaag atcaagaagg taaatcagat tttgaaagtg     60
aaaagcccag agttggagca accaccgtcc agtcagcata ggcccagtca caaagacctg    120
gcggccatct tggaaaag                                                   138

<210> SEQ ID NO 166
<211> LENGTH: 87
<212> TYPE: DNA
<213> ORGANISM: Mus musculus

<400> SEQUENCE: 166
gcacactcat tctccgtttt cagactcccg agttggtgga ttgtgggctg gtggagcaaa     60
ggtggagtag gctctgattt agaaatg                                          87

<210> SEQ ID NO 167
<211> LENGTH: 105
<212> TYPE: DNA
<213> ORGANISM: Mus musculus

<400> SEQUENCE: 167
cctgatataa aacatccagg aaatctggaa cactatataa aaagagtaaa cctaagaata     60
atagcaatag aagaaggaga aaaatcccag ctcaaaggcc cgaaa                     105

<210> SEQ ID NO 168
<211> LENGTH: 5172
<212> TYPE: DNA
<213> ORGANISM: Artificial Sequence
<220> FEATURE:
<223> OTHER INFORMATION: vector CMV-FosCBPzz

<400> SEQUENCE: 168
atgcattagt tattaatagt aatcaattac ggggtcatta gttcatagcc catatatgga     60
```

```
gttccgcgtt acataactta cggtaaatgg cccgcctggc tgaccgccca acgaccccg    120
cccattgacg tcaataatga cgtatgttcc catagtaacg ccaataggga cttnccattg    180
acgtcaatgg gtggagtatt tacggtaaac tgcccacttg gcagtacatc aagtgtatca    240
tatgccaagt acgcccccta ttgacgtcaa tgacggtaaa tggcccgcct ggcattatgc    300
ccagtacatg accttatggg actttcctac ttggcagtac atctacgtat tagtcatcgc    360
tattaccatg gtgatgcggt tttggcagta catcaatggg cgtggatagc ggtttgactc    420
acggggattt ccaagtctcc accccattga cgtcaatggg agtttgtttt ggcaccaaaa    480
tcaacgggac tttccaaaat gtcgtaacaa ctccgcccca ttgacgcaaa tgggcggtag    540
gcgtgtacgg tgggaggtct atataagcag agctggttta gtgaaccgtc agatccgcta    600
gcgattacgc caagctcgaa attaaccctc actaaggga acaaaagctg agctccacc    660
gcggtggcgg ccgctctagc ccgggcggat cacgatcccg cgaaattaat acgactcact    720
ataggggaat tgtgagcgga taacaattcc cctctagaaa taattttgtt taacttt aag    780
aaggagatat accatggcta gcatgactgg tggacagcaa atgggtcgcg gatccggcag    840
agcgcagagc atcggcagaa ggggcaaagt agagcagcta tctcctgaag aggaagagaa    900
acggagaatc gaagggaac ggaataagat ggctgcagcc aagtgccgga tcggaggag    960
ggagctgaca gatacactcc aagcggagac agatcaactt gaagatgaga agtctgcgtt   1020
gcagactgag attgccaatc tgctgaaaga gaaggaaaaa ctggagttta ttttggcagc   1080
ccaccgacct gcctgcaaga tccccgatga ccttggcctc gagctcaaga gaagatggaa   1140
aaagaatttc atagccgtct cagcagccaa ccgcttaag aaatctcat cctccggggc   1200
acttggatca gattatgata ttccaactac tgctagcgag aatttgtatt ttcagggtgg   1260
taccaaaacc gcggctcttg cgcaacacga tgaagccgta gacaacaaat tcaacaaaga   1320
acaacaaac gcgttctatg agatcttaca tttacctaac ttaaacgaag aacaacgaaa   1380
cgccttcatc caaagtttaa aagatgaccc aagccaaagc gctaaccttt tagcagaagc   1440
taaaaagcta atgatgctc aggcgccgaa agtagacaac aaattcaaca agaacaaca   1500
aaacgcgttc tatgagatct acatttacc taacttaaac gaagaacaac gaaacgcctt   1560
catccaaagt ttaaaagatg acccaagcca aagcgctaac cttttagcag aagctaaaaa   1620
gctaaatgat gctcaggcgc cgaaagtaga cgcgaattct agctctgtac cccatcacca   1680
tcaccatcac taagtcgact tcgatcgccc ttcccaacag ttgcgcagcc tgaatggcga   1740
atggagatcc aattttaag tgtataatgt gttaaactac tgattctaat tgtttgtgta   1800
ttttagattc acagtcccaa ggctcatttc aggccctca gtcctcacag tctgttcatg   1860
atcataatca gccataccac atttgtagag gttttacttg ctttaaaaaa cctcccacac   1920
ctccccctga acctgaaaca taaatgaat gcaattgttg ttgttaactt gtttattgca   1980
gcttataatg gttacaaata agcaatagc atcacaaatt tcacaaataa agcatttttt   2040
tcactgcatt ctagttgtgg tttgtccaaa ctcatcaatg tatcttaacg cgtaaattgt   2100
aagcgttaat attttgttaa aattcgcgtt aaattttgt taaatcagct cattttttaa   2160
ccaataggcc gaaatcggca aaatcccctta taaatcaaaa gaatagaccg agataggtt   2220
gagtgttgtt ccagtttgga acaagagtcc actattaaag aacgtggact ccaacgtcaa   2280
agggcgaaaa accgtctatc agggcgatgg cccactacgt gaaccatcac cctaatcaag   2340
ttttttgggg tcgaggtgcc gtaaagcact aaatcggaac cctaaaggga gcccccgatt   2400
```

```
tagagcttga cggggaaagc cggcgaacgt ggcgagaaag gaagggaaga aagcgaaagg    2460
agcgggcgct agggcgctgg caagtgtagc ggtcacgctg cgcgtaacca ccacacccgc    2520
cgcgcttaat gcgccgctac agggcgcgtc aggtggcact tttcggggaa atgtgcgcgg    2580 aaccccctatt tgtttatttt tctaaataca ttcaaatatg tatccgctca tgagacaata    2640
accctgataa atgcttcaat aatattgaaa aaggaagaat cctgaggcgg aaagaaccag    2700
ctgtggaatg tgtgtcagtt agggtgtgga aagtccccag gctcccagc aggcagaagt     2760 atgcaaagca tgcatctcaa ttagtcagca accaggtgtg gaaagtcccc aggctcccca    2820
gcaggcagaa gtatgcaaag catgcatctc aattagtcag caaccatagt cccgccccta    2880
actccgccca tcccgcccct aactccgccc agttccgccc attctccgcc ccatggctga    2940 ctaattttttt ttatttatgc agaggccgag gccgcctcgg cctctgagct attccagaag   3000
tagtgaggag gcttttttgg aggcctaggc ttttgcaaag atcgatcaag acacaggatg    3060
aggatcgttt cgcatgattg aacaagatgg attgcacgca ggttctccgg ccgcttgggt    3120
ggagaggcta ttcggctatg actgggcaca acagacaatc ggctgctctg atgccgccgt    3180
gttccggctg tcagcgcagg ggcgcccggt tctttttgtc aagaccgacc tgtccggtgc    3240
cctgaatgaa ctgcaagacg aggcagcgcg gctatcgtgg ctggccacga cgggcgttcc    3300
ttgcgcagct gtgctcgacg ttgtcactga agcgggaagg gactggctgc tattgggcga    3360
agtgccgggg caggatctcc tgtcatctca ccttgctcct gccgagaaag tatccatcat    3420
ggctgatgca atgcggcggc tgcatacgct tgatccggct acctgcccat tcgaccacca    3480
agcgaaacat cgcatcgagc gagcacgtac tcggatggaa gccggtcttg tcgatcagga    3540
tgatctggac gaagaacatc aggggctcgc gccagccgaa ctgttcgcca ggctcaaggc    3600
gagcatgccc gacggcgagg atctcgtcgt gacccatggc gatgcctgct tgccgaatat    3660
catggtggaa aatggccgct tttctggatt catcgactgt ggccggctgg gtgtggcgga    3720
ccgctatcag gacatagcgt tggctacccg tgatattgct gaagaacttg gcggcgaatg    3780
ggctgaccgc ttcctcgtgc tttacggtat cgccgctccc gattcgcagc gcatcgcctt    3840
ctatcgcctt cttgacgagt tcttctgagc gggactctgg ggttcgaaat gaccgaccaa    3900
gcgacgccca acctgccatc acgagatttc gattccaccg ccgccttcta tgaaaggttg    3960
ggcttcggaa tcgttttccg gacgccggc tggatgatcc tccagcgcgg ggatctcatg     4020
ctggagttct cgcccacccc tagggggagg ctaactgaaa cacggaagga acaataccg     4080 gaaggaaccc gcgctatgac ggcaataaaa agacagaata aaacgcacgg tgttgggtcg    4140
tttgttcata acgcggggt tcggtcccag ggctggcact ctgtcgatac cccaccgaga     4200
ccccattggg gccaatacgc ccgcgtttct tccttttccc caccccaccc cccaagttcg    4260
ggtgaaggcc cagggctcgc agccaacgtc ggggcggcag gccctgccat agcctcaggt    4320
tactcatata tactttagat tgatttaaaa cttcattttt aatttaaaag gatctaggtg    4380
aagatccttt ttgataatct catgaccaaa atcccttaac gtgagttttc gttccactga    4440
gcgtcagacc ccgtagaaaa gatcaaagga tcttcttgag atcctttttt tctgcgcgta    4500
atctgctgct tgcaaacaaa aaaccaccg ctaccagcgg tggtttgttt gccggatcaa     4560
gagctaccaa ctctttttcc gaaggtaact ggcttcagca gagcgcagat accaaatact    4620
gtccttctag tgtagccgta gttaggccac cacttcaaga actctgtagc accgcctaca    4680
tacctcgctc tgctaatcct gttaccagtg ctgctgccag tggcgataag tcgtgtctt     4740 accgggttgg actcaagacg atagttaccg gataaggcgc agcggtcggg ctgaacgggg    4800
```

```
ggttcgtgca cacagcccag cttggagcga acgacctaca ccgaactgag atacctacag   4860
cgtgagctat gagaaagcgc cacgcttccc gaagggagaa aggcggacag gtatccggta   4920
agcggcaggg tcggaacagg agagcgcacg agggagcttc caggggggaaa cgcctggtat   4980 ctttatagtc ctgtcgggtt tcgccacctc tgacttgagc gtcgattttt gtgatgctcg   5040 tcagggggc ggagcctatg gaaaaacgcc agcaacgcgg ccttttttacg gttcctggcc    5100 ttttgctggc cttttgctca catgttcttt cctgcgttat ccctgattc tgtggataac     5160 cgtattaccg cc                                                        5172
```

<210> SEQ ID NO 169
<211> LENGTH: 70
<212> TYPE: DNA
<213> ORGANISM: Artificial Sequence
<220> FEATURE:
<223> OTHER INFORMATION: PCR primer 5'SP6(O29)T7-FosCBPzz

<400> SEQUENCE: 169

```
gaatttaggt gacactatag aacaacaaca acaacaaaca acaacaaaat ggctagcatg    60
actggtggac                                                            70
```

<210> SEQ ID NO 170
<211> LENGTH: 20
<212> TYPE: DNA
<213> ORGANISM: Artificial Sequence
<220> FEATURE:
<223> OTHER INFORMATION: PCR primer 3'FosCBPzz

<400> SEQUENCE: 170

```
ggatctccat tcgccattca                                                 20
```

<210> SEQ ID NO 171
<211> LENGTH: 89
<212> TYPE: DNA
<213> ORGANISM: Artificial Sequence
<220> FEATURE:
<223> OTHER INFORMATION: DNA beit template DNA-Fos/Jun

<400> SEQUENCE: 171

```
cgactctgac ggcagtttac gtgactcatg agtcatgact catgagtcat gactcatgag    60
tcacgttaga acgcggctac aattaatac                                       89
```

<210> SEQ ID NO 172
<211> LENGTH: 21
<212> TYPE: DNA
<213> ORGANISM: Artificial Sequence
<220> FEATURE:
<223> OTHER INFORMATION: PCR primer 5'DNA

<400> SEQUENCE: 172

```
cgactctgac ggcagtttac g                                               21
```

<210> SEQ ID NO 173
<211> LENGTH: 26
<212> TYPE: DNA
<213> ORGANISM: Artificial Sequence
<220> FEATURE:
<223> OTHER INFORMATION: PCR primer 3'DNA

<400> SEQUENCE: 173

```
gtattaattg tagccgcgtt ctaacg                                          26
```

<210> SEQ ID NO 174
<211> LENGTH: 67
<212> TYPE: DNA
<213> ORGANISM: Artificial Sequence
<220> FEATURE:
<223> OTHER INFORMATION: main chain of adaptor (O29)

<400> SEQUENCE: 174
gaacaacaac aacaacaaac aacaacaaaa tgactggtgg acagcaaatg ggtgcggccg    60
cgaattc    67

<210> SEQ ID NO 175
<211> LENGTH: 68
<212> TYPE: DNA
<213> ORGANISM: Artificial Sequence
<220> FEATURE:
<223> OTHER INFORMATION: main chain of adaptor (O29-2)

<400> SEQUENCE: 175
gaacaacaac aacaacaaac aacaacaaaa tggctagcat gactggtgga cagcaaatgg    60
cgaattcc    68

<210> SEQ ID NO 176
<211> LENGTH: 32
<212> TYPE: DNA
<213> ORGANISM: Artificial Sequence
<220> FEATURE:
<223> OTHER INFORMATION: random primer for reverse transcription
<220> FEATURE:
<221> NAME/KEY: misc_feature
<222> LOCATION: (24)..(32)
<223> OTHER INFORMATION: n = a, t, g or c

<400> SEQUENCE: 176
tcatcgtcct tgtagtcaag cttnnnnnnn nn    32

<210> SEQ ID NO 177
<211> LENGTH: 58
<212> TYPE: DNA
<213> ORGANISM: Artificial Sequence
<220> FEATURE:
<223> OTHER INFORMATION: PCR 5' primer (O29)

<400> SEQUENCE: 177
ggaagatcta tttaggtgac actatagaac aacaacaaca caaacaaca acaaaatg    58

<210> SEQ ID NO 178
<211> LENGTH: 36
<212> TYPE: DNA
<213> ORGANISM: Artificial Sequence
<220> FEATURE:
<223> OTHER INFORMATION: PCR 3' primer

<400> SEQUENCE: 178 tttttttct tgtcgtcatc gtccttgtag tcaagc    36

<210> SEQ ID NO 179
<211> LENGTH: 3851
<212> TYPE: DNA
<213> ORGANISM: Artificial Sequence
<220> FEATURE:
<223> OTHER INFORMATION: pDrive vector

<400> SEQUENCE: 179
gcgcccaata cgcaaaccgc ctctccccgc gcgttggccg attcattaat gcagctggca    60

```
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcgga taacaatttc acacaggaaa cagctatgac catgattacg ccaagctcta    240
atacgactca ctatagggaa agctcggtac cacgcatgct gcagacgcgt tacgtatcgg    300
atccagaatt cgtgatatct gaattcgtcg acaagcttct cgagcctagg ctagctctag    360
accacacgtg tggggcccg agctcgcggc cgctgtattc tatagtgtca cctaaatggc    420
cgcacaattc actggccgtc gttttacaac gtcgtgactg ggaaaaccct ggcgttaccc    480
aacttaatcg ccttgcagca catccccctt cgccagctg gcgtaatagc gaagaggccc    540
gcaccgatcg cccttcccaa cagttgcgca gcctgaatgg cgaatggaaa ttgtaagcgt    600
taatattttg ttaaaattcg cgttaaattt ttgttaaatc agctcatttt ttaaccaata    660
ggccgaaatc ggcaaaatcc cttataaatc aaaagaatag accgagatag ggttgagtgt    720
tgttccagtt tggaacaaga gtccactatt aaagaacgtg gactccaacg tcaaagggcg    780
aaaaaccgtc tatcagggcg atggcccact acgtgaacca tcaccctaat caagttttt    840
ggggtcgagg tgccgtaaag cactaaatcg aaccctaaa gggagccccc gatttagagc    900
ttgacgggga agccggcga acgtggcgag aaaggaaggg aagaaagcga aggagcggg    960
cgctagggcg ctggcaagtg tagcggtcac gctgcgcgta accaccacac ccgccgcgct   1020
taatgcgccg ctacagggcg cgtcaggtgg cacttttcgg ggaaatgtgc gcggaacccc   1080
tatttgttta ttttctaaa tacattcaaa tatgtatccg ctcatgagac aataaccctg   1140
ataaatgctt caataatatt gaaaaggaa gagtatgagt attcaacatt tccgtgtcgc   1200
ccttattccc ttttttgcgg catttgcct tcctgttttt gctcacccag aaacgctggt   1260
gaaagtaaaa gatgctgaag atcagttggg tgcacgagtg ggttacatcg aactggatct   1320
caacagcggt aagatccttg agagttttcg ccccgaagaa cgttttccaa tgatgagcac   1380
ttttaaagtt ctgctatgtg gcgcggtatt atcccgtatt gacgccgggc aagagcaact   1440
cggtcgccgc atacactatt ctcagaatga cttggttgag tactcaccag tcacagaaaa   1500
gcatcttacg gatggcatga cagtaagaga attatgcagt gctgccataa ccatgagtga   1560
taacactgcg gccaacttac ttctgacaac gatcggagga ccgaaggagc taaccgcttt   1620
tttgcacaac atgggggatc atgtaactcg ccttgatcgt tgggaaccgg agctgaatga   1680
agccatacca aacgacgagc gtgacaccac gatgcctgta gcaatggcaa caacgttgcg   1740
caaactatta actggcgaac tacttactct agcttcccgg caacaattaa tagactggat   1800
ggaggcggat aaagttgcag gaccacttct gcgctcggcc cttccggctg gctggtttat   1860
tgctgataaa tctggagccg gtgagcgtgg gtctcgcggt atcattgcag cactggggcc   1920
agatggtaag ccctcccgta tcgtagttat ctacacgacg gggagtcagg caactatgga   1980
tgaacgaaat agacagatcg ctgagatagg tgcctcactg attaagcatt ggtaactgtc   2040
agaccaagtt tactcatata ctttagat tgatttaaaa cttcattttt aatttaaaag   2100
gatctaggtg aagatccttt ttgataatct catgaacaat aaaactgtct gcttacataa   2160
acagtaatac aagggtgtt atgagccata ttcaacggga acgtcttgc tctaggccgc   2220
gattaaattc caacatggat gctgatttat atgggtataa atgggctcgc gataatgtcg   2280
ggcaatcagg tgcgacaatc tatcgattgt atgggaagcc cgatgcgcca gagttgtttc   2340
tgaaacatgg caaaggtagc gttgccaatg atgttacaga tgagatggtc agactaaact   2400
```

-continued

```
ggctgacgga atttatgcct cttccgacca tcaagcattt tatccgtact cctgatgatg      2460
catggttact caccactgcg atccccggga aaacagcatt ccaggtatta gaagaatatc      2520
ctgattcagg tgaaaatatt gttgatgcgc tggcagtgtt cctgcgccgg ttgcattcga      2580
ttcctgtttg taattgtcct tttaacagcg atcgcgtatt tcgtctcgct caggcgcaat      2640
cacgaatgaa taacggtttg gttgatgcga gtgattttga tgacgagcgt aatggctggc      2700
ctgttgaaca agtctggaaa gaaatgcata aacttttgcc attctcaccg gattcagtcg      2760
tcactcatgg tgatttctca cttgataacc ttatttttga cgaggggaaa ttaataggtt      2820
gtattgatgt tggacgagtc ggaatcgcag accgatacca ggatcttgcc atcctatgga      2880
actgcctcgg tgagttttct ccttcattac agaaacggct ttttcaaaaa tatggtattg      2940
ataatcctga tatgaataaa ttgcagtttc atttgatgct cgatgagttt ttctaagaat      3000
taattcatga ccaaaatccc ttaacgtgag ttttcgttcc actgagcgtc agaccccgta      3060
gaaaagatca aaggatcttc ttgagatcct ttttttctgc gcgtaatctg ctgcttgcaa      3120
acaaaaaaac caccgctacc agcggtggtt tgtttgccgg atcaagagct accaactctt      3180
tttccgaagg taactggctt cagcagagcg cagataccaa atactgtcct tctagtgtag      3240
ccgtagttag gccaccactt caagaactct gtagcaccgc ctacatacct cgctctgcta      3300
atcctgttac cagtggctgc tgccagtggc gataagtcgt gtcttaccgg gttggactca      3360
agacgatagt taccggataa ggcgcagcgg tcgggctgaa cggggggttc gtgcacacag      3420
cccagcttgg agcgaacgac ctacaccgaa ctgagatacc tacagcgtga gctatgagaa      3480
agcgccacgc ttcccgaagg gagaaaggcg gacaggtatc cggtaagcgg cagggtcgga      3540
acaggagagc gcacgaggga gcttccaggg ggaaacgcct ggtatcttta tagtcctgtc      3600
gggtttcgcc acctctgact tgagcgtcga ttttttgtgat gctcgtcagg ggggcggagc      3660
ctatggaaaa acgccagcaa cgcggccttt ttacggttcc tggccttttg ctggccttttt     3720 gctcacatgt tctttcctgc gttatcccct gattctgtgg ataaccgtat taccgccttt      3780
gagtgagctg ataccgctcg ccgcagccga acgaccgagc gcagcgagtc agtgagcgag      3840
gaagcggaag a                                                          3851
```

<210> SEQ ID NO 180
<211> LENGTH: 58
<212> TYPE: DNA
<213> ORGANISM: Artificial Sequence
<220> FEATURE:
<223> OTHER INFORMATION: primer 5'F3

<400> SEQUENCE: 180

```
ggaagatcta tttaggtgac actatagaac aacaacaaca caaacaaca acaaaatg        58
```

<210> SEQ ID NO 181
<211> LENGTH: 27
<212> TYPE: DNA
<213> ORGANISM: Artificial Sequence
<220> FEATURE:
<223> OTHER INFORMATION: primer 3'R3

<400> SEQUENCE: 181

```
ttttttttct cgagcttgtc gtcatcg                                          27
```

<210> SEQ ID NO 182
<211> LENGTH: 18
<212> TYPE: DNA
<213> ORGANISM: Artificial Sequence

```
<220> FEATURE:
<223> OTHER INFORMATION: primer Optn_F

<400> SEQUENCE: 182
tgggcatcgt ctcagaac                                                 18

<210> SEQ ID NO 183
<211> LENGTH: 18
<212> TYPE: DNA
<213> ORGANISM: Artificial Sequence
<220> FEATURE:
<223> OTHER INFORMATION: primer Optn_R

<400> SEQUENCE: 183
tgtgggtgta gggcagtt                                                 18

<210> SEQ ID NO 184
<211> LENGTH: 18
<212> TYPE: DNA
<213> ORGANISM: Artificial Sequence
<220> FEATURE:
<223> OTHER INFORMATION: primer SNAP19_F

<400> SEQUENCE: 184
aaaccctgct gcgtctaa                                                 18

<210> SEQ ID NO 185
<211> LENGTH: 19
<212> TYPE: DNA
<213> ORGANISM: Artificial Sequence
<220> FEATURE:
<223> OTHER INFORMATION: primer SNAP19_R

<400> SEQUENCE: 185
atcatggatt gaagggcta                                                19

<210> SEQ ID NO 186
<211> LENGTH: 17
<212> TYPE: DNA
<213> ORGANISM: Artificial Sequence
<220> FEATURE:
<223> OTHER INFORMATION: primer C130020M04RIK_F

<400> SEQUENCE: 186
ggtgtcctcc ctggaaa                                                  17

<210> SEQ ID NO 187
<211> LENGTH: 20
<212> TYPE: DNA
<213> ORGANISM: Artificial Sequence
<220> FEATURE:
<223> OTHER INFORMATION: primer C130020M04RIK_R

<400> SEQUENCE: 187
tgggcaatct ttatgagcta                                               20

<210> SEQ ID NO 188
<211> LENGTH: 18
<212> TYPE: DNA
<213> ORGANISM: Artificial Sequence
<220> FEATURE:
<223> OTHER INFORMATION: primer Rattus FLJ32000_F

<400> SEQUENCE: 188
aagagcgcac caatgaca                                                 18
```

```
<210> SEQ ID NO 189
<211> LENGTH: 20
<212> TYPE: DNA
<213> ORGANISM: Artificial Sequence
<220> FEATURE:
<223> OTHER INFORMATION: primer Rattus FLJ32000_R

<400> SEQUENCE: 189
tcttgaatgg tctcatccct                                           20

<210> SEQ ID NO 190
<211> LENGTH: 21
<212> TYPE: DNA
<213> ORGANISM: Artificial Sequence
<220> FEATURE:
<223> OTHER INFORMATION: primer 5'M13_F

<400> SEQUENCE: 190
gttttcccag tcacgacgtt g                                         21

<210> SEQ ID NO 191
<211> LENGTH: 24
<212> TYPE: DNA
<213> ORGANISM: Artificial Sequence
<220> FEATURE:
<223> OTHER INFORMATION: primer 3'M13_R

<400> SEQUENCE: 191
gaaacagcta tgaccatgat tacg                                      24
```